US005313532A

United States Patent [19]

Harvey et al.

[11] Patent Number: 5,313,532

[45] Date of Patent: May 17, 1994

[54] RECOGNITION OF PATTERNS IN IMAGES

[75] Inventors: Robert L. Harvey, Lexington; Paul N. DiCaprio, Belmont; Karl G. Heinemann, Cambridge, all of Mass.

[73] Assignee: Massachusetts Institute of Technology, Cambridge, Mass.

[21] Appl. No.: 784,634

[22] Filed: Oct. 28, 1991

Related U.S. Application Data

[63] Continuation of Ser. No. 489,470, Mar. 6, 1990, abandoned, which is a continuation-in-part of Ser. No. 468,681, Jan. 23, 1990, abandoned.

[51] Int. Cl.[5] .......... G06K 9/62

[52] U.S. Cl. .......... 382/15; 382/6; 382/22; 382/48

[58] Field of Search .......... 382/21, 22, 6, 36, 48, 382/14, 15; 964/413.1

[56] References Cited

U.S. PATENT DOCUMENTS

| | | | |
|---|---|---|---|
| 3,643,215 | 2/1972 | Ingham et al. | 340/146.3 |
| 4,125,828 | 11/1978 | Resnick et al. | 340/146.3 |
| 4,232,970 | 11/1980 | Sawamura et al. | 356/432 |
| 4,242,662 | 12/1980 | Tsujiyama et al. | 340/146.3 |
| 4,523,278 | 6/1985 | Reinhardt et al. | 364/413 |
| 4,685,143 | 8/1987 | Choate | 382/25 |
| 4,803,736 | 2/1989 | Grossberg et al. | 382/22 |
| 4,805,225 | 2/1989 | Clark | 382/15 |
| 4,876,731 | 10/1989 | Lorris et al. | 382/40 |
| 4,881,178 | 11/1989 | Holland et al. | 364/513 |
| 4,881,270 | 11/1989 | Knecht | 382/17 |
| 4,914,708 | 4/1990 | Carpenter et al. | 382/14 |
| 4,965,725 | 10/1990 | Rutenberg | 364/413.1 |
| 4,972,499 | 11/1990 | Kurosawa | 382/38 |
| 4,996,593 | 2/1991 | Hopkins | 358/101 |

FOREIGN PATENT DOCUMENTS

| | | |
|---|---|---|
| 0336608 | 3/1989 | European Pat. Off. . |
| WO8909969 | 3/1989 | PCT Int'l Appl. . |

OTHER PUBLICATIONS

Carpenter, Gail, et al., "Self-Organization of Stabel Category Recognition Codes for Analog Input Patterns," Applied Optics, pp. 1-23, 1987.

Watanabe, S. et al., "A pap Smear Prescreening System: Cybest," Digital Processing of Biomedical Images, pp. 227-241, 1976.

Watanabe, S. et al. "The Development of a New Model Cyto-Prescreener for Cervical Cancer," Real-Time Medical Image Processing, pp. 221-229.

Mukawa, A. et al., "Progress Report on Experimental Use of CYBEST Model 2 for Practical Gynecologic Mass Screening." pp. 31-34, Mar. 1983.

Rennie, J., "Cancer Catcher," Scientific America, p. 84, May 1990.

Grossberg, S. "Nonlinear Neural Networks: Principles, Mechanism, and Architectures," Neural Networks, vol. 1, pp. 17-61, 1988.

(List continued on next page.)

*Primary Examiner*—Michael T. Razavi

*Assistant Examiner*—Steven P. Klocinski

*Attorney, Agent, or Firm*—Fish & Richardson

[57] ABSTRACT

A pattern (e.g., the normal or abnormal characteristics of a biological cell) within an image is recognized based on visual characteristics of the pattern, the image being represented by signals whose values correspond to the visual characteristics, using a location channel which determines the location of the pattern within the image based on the signal values, and a classification channel which categorizes the pattern based on the signal values, the location channel and the classification channel operating in parallel and cooperatively to recognize the pattern. In other aspects, there the orientations of edges of the pattern within subwindows of the image are analyzed as are the strengths of edges of the pattern near the periphery of portions of the image; an unsupervised classifier defines internal representation classes of objects, and a supervised classifier maps the classes to user-specified categories; and there is a feedback path from the classification channel to the location channel to cause the location channel to adapt to classification results generated by the classification channel.

34 Claims, 16 Drawing Sheets

OTHER PUBLICATIONS

Williams, T. "Object recognition opens the eyes of machine-vision systems," Computer Design, pp. 69-83, May 1988.
Cantoni, V. et al., "Multiprocess Computer for Images," Proceedings of the IEEE, vol. 76, No. 8 pp. 959-969, Aug. 1988.
Aloimonos, J. "Visual Shape Computation," Proceedings of the IEEE, vol. 76, pp. 899-916, Aug. 1988.
Rosenfield, A. "Computer Vision: Basic Principles," Proceedings of the IEEE vol. 76, pp. 863-868, Aug. 1988.
Besl, P. "Geometric Modling and Computer Vision," Proceedings of the IEEE, vol. 76, pp. 936-958, Aug. 1988.
Burt, P. "Smart Sensing within a Pyramid Vision Machine", Proceedings of the IEEE, vol. 76, pp. 1006-1015, Aug. 1988.
Hubel, D. "Eye, Brain, and Vision," Scientific American Library, book No. 22, 1988.

EXAMPLE VISAREA 2 OUTPUTS

| Example Input from AVERAGE module, 49 | Network Outputs | | | |
|---|---|---|---|---|
| | NORTH | SOUTH | EAST | WEST |
|  | HIGH | HIGH | HIGH | HIGH |
|  | LOW | HIGH | HIGH | LOW |

PRELIMINARY CYTOLOGY RESULTS
USING SIMPLE THRESHOLD CLASSIFICATION (28 Image Training Set-33 Image Test Set)

| CELL TYPE | THRESHOLD | SYSTEM CLASSIFICATION NORMAL | ABNORMAL | TOTAL |
|---|---|---|---|---|
| NORMAL | HIGH | 10 | 7 | 17 |
| | LOW | 7 | 10 | 17 |
| ABNORMAL | HIGH | 10 | 6 | 16 |
| | LOW | 3 | 13 | 16 |

FALSE POSITIVES

FALSE NEGATIVES

FIG. 15

RECOGNITION OF PATTERNS IN IMAGES

The Government has rights in this invention pursuant to contract Number F19628-85-C-0002 awarded by the Department of the Air Force.

This is a continuation of copending application Ser. No. 07/489,470 filed on Mar. 6, 1990 now abandoned, which is a continuation-in-part of U.S. patent application Ser. No. 07/468,681, filed Jan. 23, 1990 now abandoned.

BACKGROUND OF THE INVENTION

This invention relates to recognition by machines of patterns in images.

The mechanisms by which patterns representing objects are recognized by animals has been studied extensively. A summary of studies of the human visual system is given in D. H. Hubel, "Eye, Brain, and Vision," New York, N.Y.: W. H. Freeman and Company, 1988. Machine based visual recognition schemes typically use combinations of opto-electronic devices and computer data processing techniques to recognize objects.

In general, recognizing an object requires determining Whether a certain pattern (corresponding to the object) appears within a field-of-view (FOV) of an input image. The pattern generally is defined by spatial gradients and discontinuities in luminance across the input image. Other types of gradients and discontinuities may also produce perceivable patterns. Perceivable patterns may occur in the presence of: statistical differences in textural qualities (such as orientation, shape, density, or color), binocular matching of elements of differing disparities, accretion and deletion of textural elements in moving displays, and classical 'subjective contours'. An input image is here meant to include any two-dimensional, spatially ordered array of signal intensities. The signals may be of any frequency within the entire electromagnetic spectrum, such as infrared radiation signals and radar ranging signals. Thus visual recognition here denotes recognition of an object based on electromagnetic radiation received from the object.

Humans easily recognize spatial gray-scale object patterns regardless of the patterns' location or rotational orientation within a FOV. In perceiving these patterns, the human visual recognition system operates in two stages, first locating patterns of interest within the FOV, and then classifying the patterns according to known categories of objects.

Biological vision systems can rapidly segment an input image in a manner described as "preattentive." It has been found experimentally that segmentation is context-sensitive, i.e., what is perceived as a pattern at a given location can depend on patterns at nearby locations.

Contemporary image-processing techniques based on artificial intelligence (AI) systems use geometric concepts such as surface normal, curvature, and the Laplacian. These approaches were originally developed to analyze the local properties of physical processes.

SUMMARY OF THE INVENTION

In general, in one aspect, the invention features apparatus for recognizing a pattern within an input image based on visual characteristics of the pattern, the image being represented by signals whose values correspond to the visual characteristics. The apparatus includes a location channel which determines the location of the pattern within the image based on the signal values, and a classification channel which categorizes the object based on the signal values, the location channel and the classification channel operating in parallel and cooperatively to recognize the pattern.

Preferred embodiments of the invention include the following features. The location channel includes a coarse locator which makes a coarse determination of the existence and location of the pattern within the image, and a fine locator, responsive to the coarse locator, which makes a fine determination of the location of the pattern within the image. The coarse locator includes a neural network which compares the image with traces corresponding to general shapes of interest. The coarse locator operates with respect to a field of view within the image and a feedback path from the classification channel to the locator channel controls the position of the field of view within the image. The fine locator includes circuitry for responding to feedback from the classification channel in order to adjust the position of a field of view within the image in order to determine the fine location of the pattern within the image. The coarse locator provides a feedforward signal to the fine locator which also affects the fine position of the field of view.

The classification channel includes a signal processer for preprocessing the signal values, a signal analyzer responsive to the signal processor for generating measures of the visual characteristics, and a classifier for classifying the pattern in accordance with the measures. The signal analyzer includes edge detectors for detecting information about edges of the pattern. Some edge detectors are adapted to generate measures of the strengths of edges in predetermined orientations within portions of the image. The predetermined orientations include vertical, horizontal, and 45 degrees. Other edge detectors are adapted to generate measures of the existence of edges at the periphery of a portion of the image. The edges are detected at the top, bottom, and each side of the portion of the image. The signal analyzer also includes a gross size detector for detecting the gross size of a pattern within a portion of the image.

The measures of the visual characteristics are arrayed as a spectrum for delivery to the classifier. Measures which correspond to coarser features appear in the lower end of the spectrum and measures which correspond to finer features appear in the upper end of the spectrum. The signal analyzer includes a feedback path for providing the measures of the visual characteristics to the location channel.

In general, in another aspect, the invention features apparatus including an orientation analyzer adapted to analyze the orientations of edges of the pattern within subwindows of the image, and a strength analyzer adapted to analyze the strengths of edges of the pattern near the periphery of a portion of a window of the image.

Preferred embodiments include the following features. The orientation analyzer includes detectors for detecting the strengths of orientation of edges in four different Possible orientations: 0, 45, 90, and 135 degrees, respectively. The apparatus also includes a classifier for processing the outputs of the orientation and strength analyzers as part of a spectrum. A mapper causes outputs corresponding to subwindows of the image to be treated in the spectrum in an order such that outputs of subwindows nearer to the center of the image are treated as appearing lower on the spectrum than outputs of subwindows nearer the periphery of the image. Each analyzer includes neural networks. The strength analyzer includes an averaging module for averaging elements of the window to derive an averaged window, and four neural networks for processing the averaged window to determine the strength of edges at the north, south, east, and west peripheries of the window.

In general, in another aspect, the invention features apparatus for categorizing, among a set of user-specified categories, a pattern which appears in an image based on visual characteristics of the pattern, the image being represented by signals whose values correspond to the visual characteristics. The apparatus includes an unsupervised classifier adapted to define classes of patterns and to categorize the patterns based on the visual features and the classes, and a supervised classifier adapted to map the classes to the set of user-specified categories. In preferred embodiments, the unsupervised classifier is an ART2 classifier.

In general, in another aspect, the invention features apparatus including a location channel which determines the location of the pattern within the image based on the signal values, a classification channel which categorizes the pattern based on the signal values, and a feedback path from the classification channel to the location channel to cause the location channel to adapt to classification results generated by the classification channel.

In general, in other aspects, the abnormal or normal state of a biological cell within an image is determined based on visual characteristics of the cell, and the cell is categorized, among a set of user-specified categories, based on visual characteristics of the cell.

The invention provides a highly effective, efficient scheme for recognizing patterns. Computer processing power is devoted more heavily to portions of the image which contain possible patterns. The spectrum is arranged to place relatively gross features at the lower end and relatively detailed features at the upper end which aids analysis of the relationship between features and the resulting classification.

Biological cells, in particular cervical cells in a Pap smear, can be quickly and automatically analyzed to determine their normal or abnormal state.

Other advantages and features will become apparent from the following description of the preferred embodiment and from the claims.

DESCRIPTION OF THE PREFERRED EMBODIMENT

We first briefly describe the drawings.

Figure 13A:
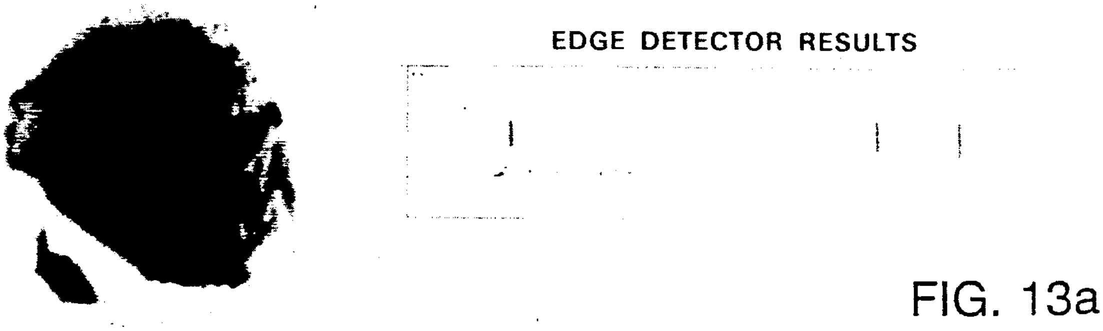

FIGS. 13A and B are photographs of NORMAL and ABNORMAL cells and related spectra.

Figure 14:
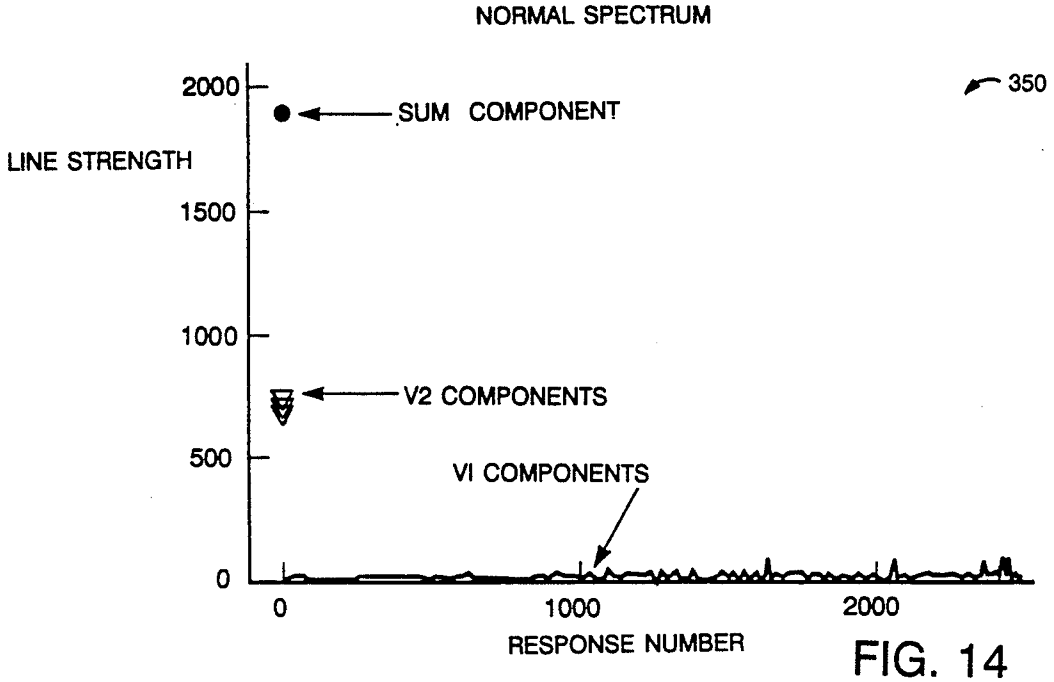

FIG. 14 is a spectrum for a NORMAL cell.

FIG. 15 is a chart of results in a simple threshold classification scheme.

Figure 16:
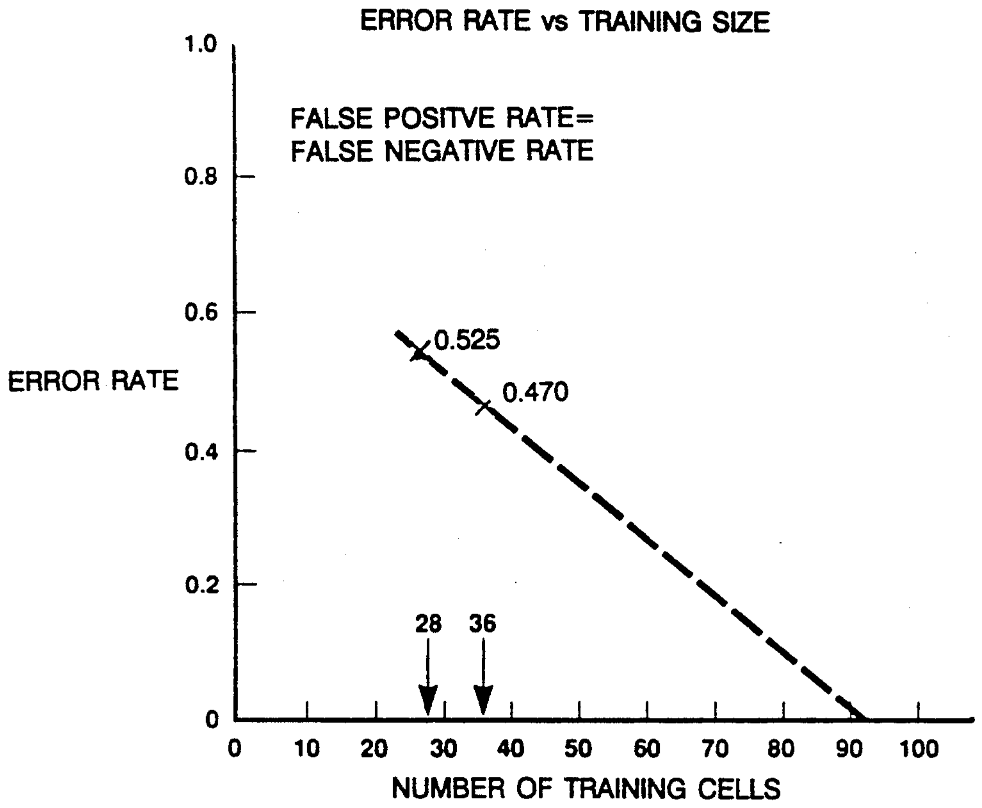
Figure 17:
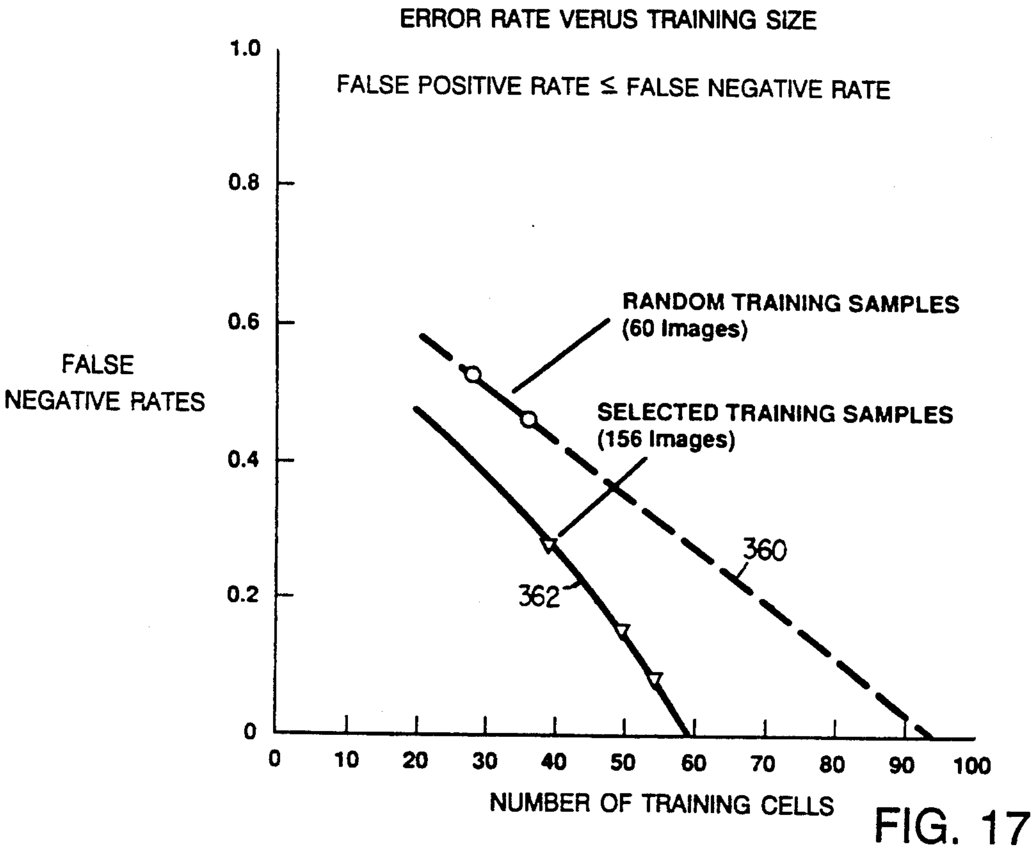

FIGS. 16 and 17 are graphs of error rate versus training size.

STRUCTURE

Figure 1:
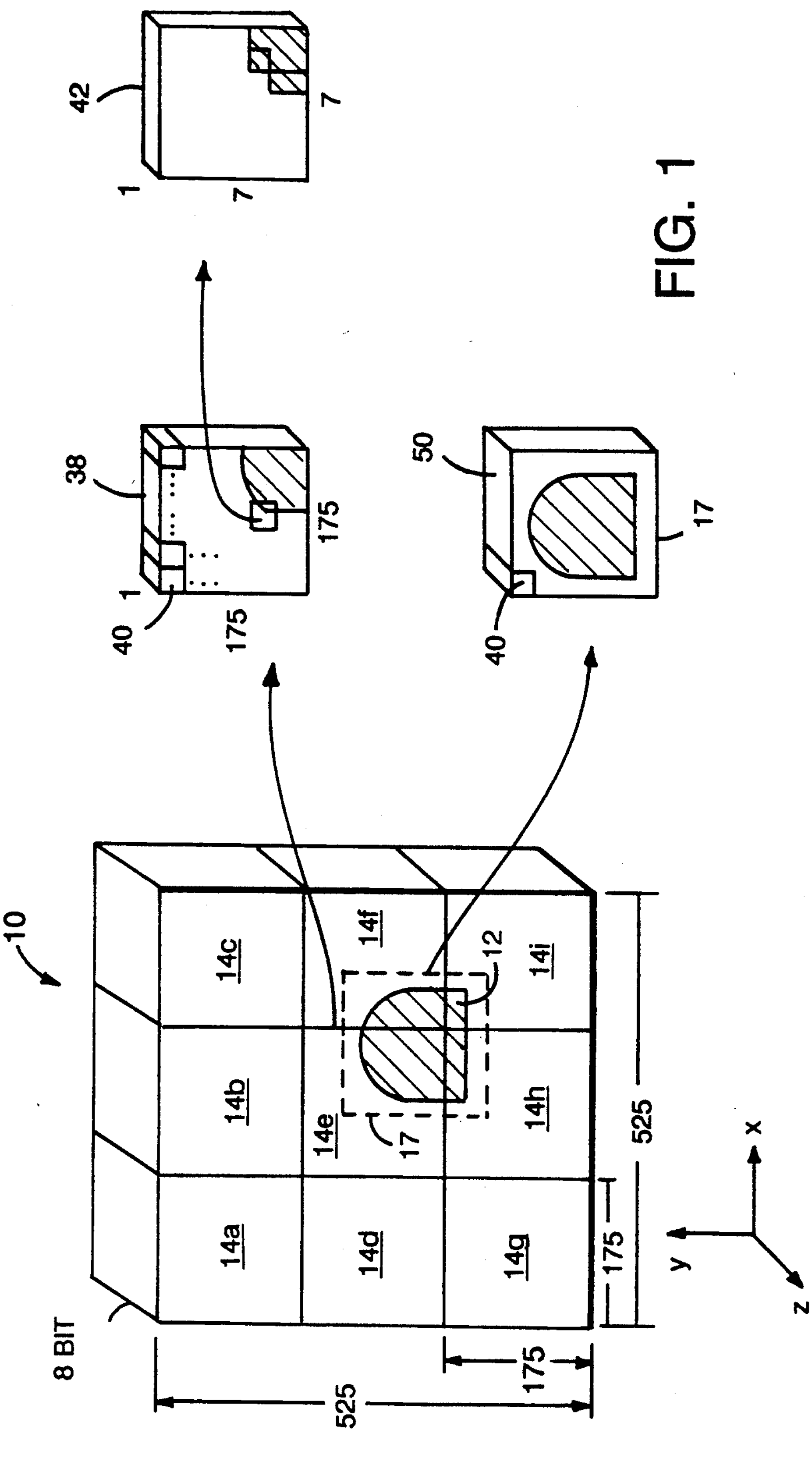
FIG. 1 is a diagram of an image pattern and windows and a subwindow of the image.

Referring to FIG. 1, consider, by way of example, an image 10 consisting of a 525 by 525 array of 8-bit pixel values. The pixels are arrayed along the x and y axes and the z axis represents an 8-bit luminance value of each pixel. A pattern 12 representing an object to be recognized within the image is defined by a collection of 8-bit pixels. The goal is to be able to recognize quickly and accurately the existence, location, and category of pattern 12 within image 10.

Figures 1, 2:
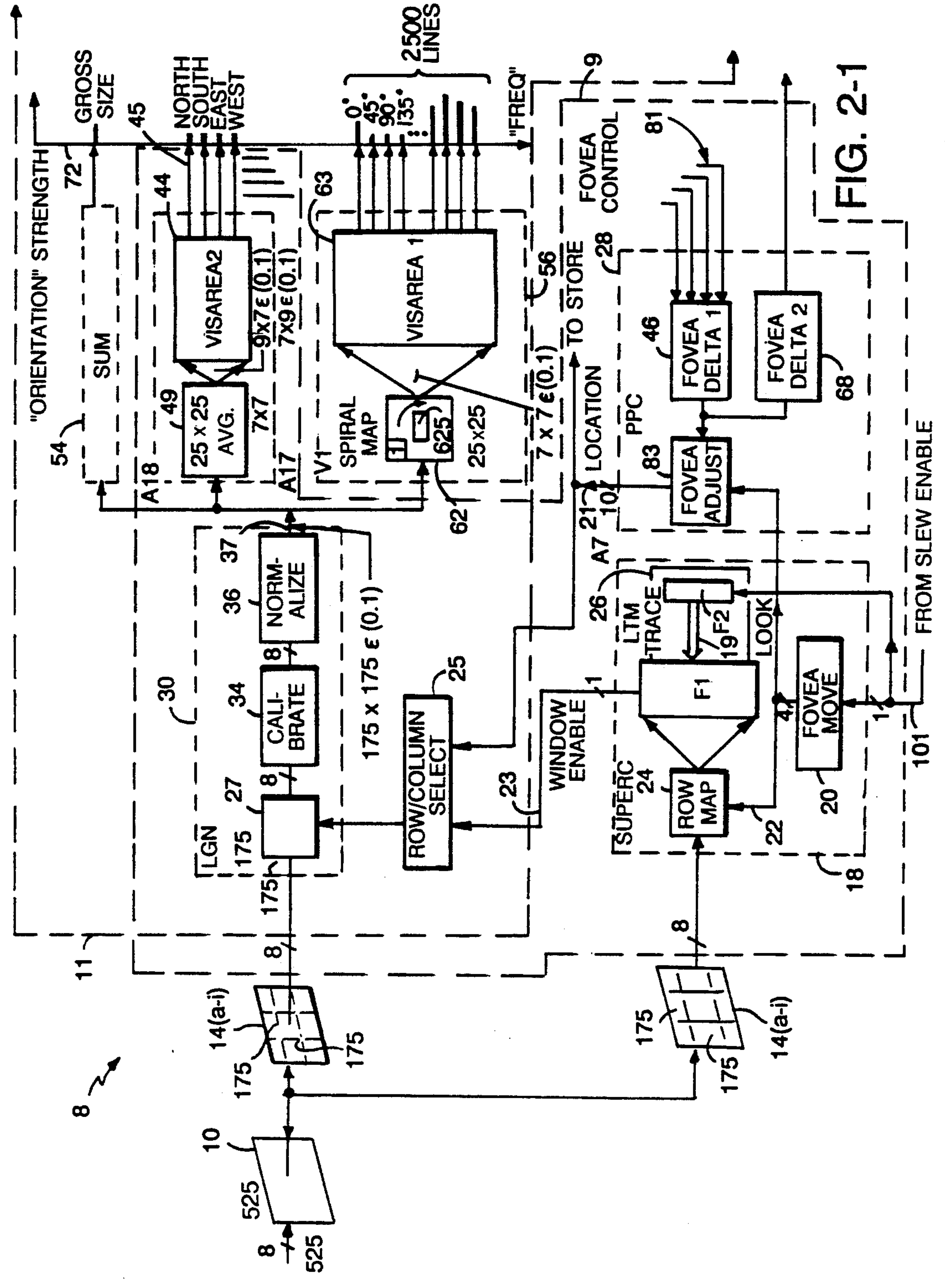
FIG. 2 is a functional block diagram of an object recognition system.
Figure 2:
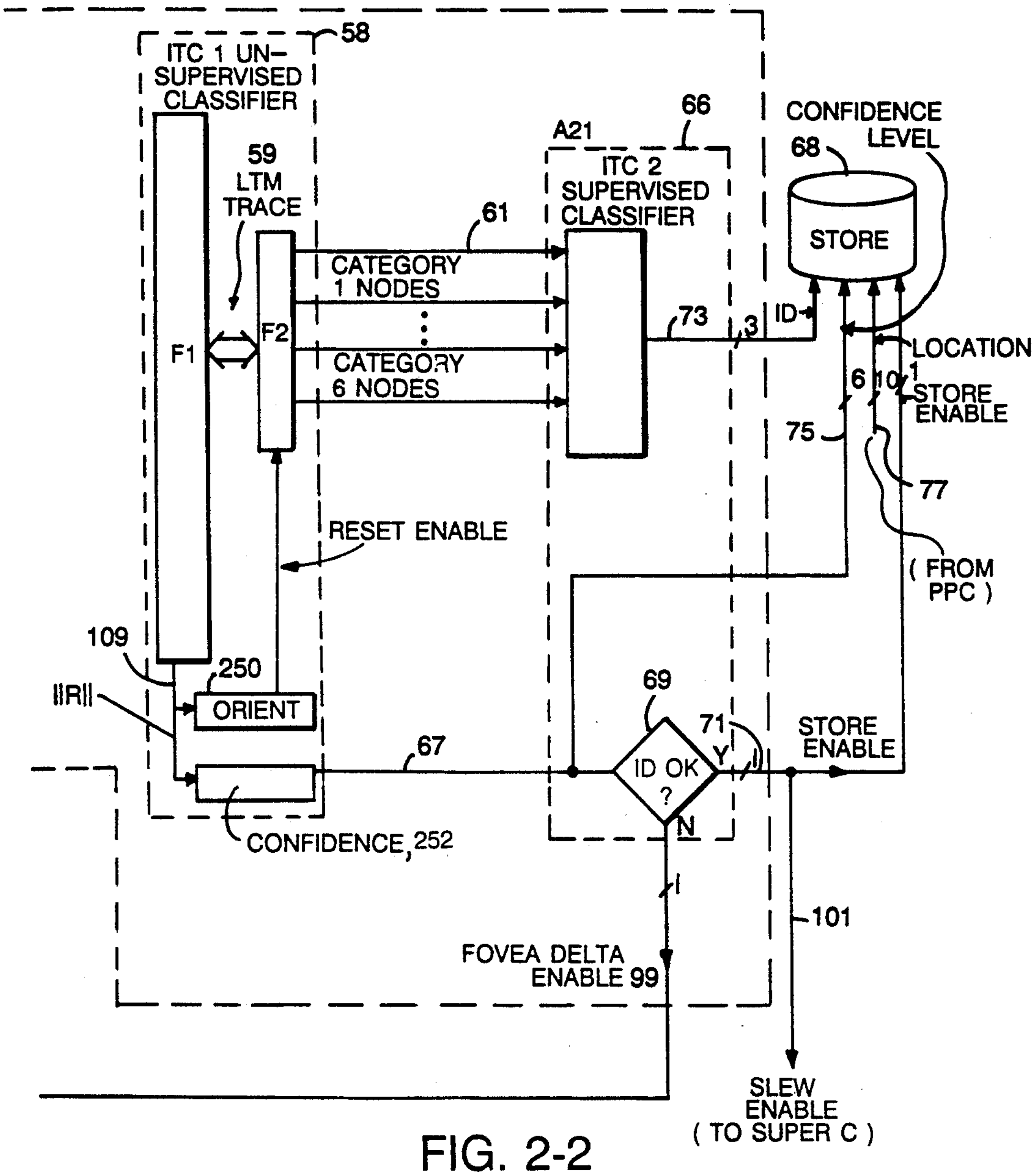

Referring to FIG. 2, the recognition task is performed by a visual recognition system 8 which includes a collection of modules which roughly achieve the functions of their biological counterparts in recognizing, in a selected FOV within the image, gray-scale patterns having arbitrary shifts and rotations.

System 8 includes a location channel 9 which locates patterns of interest in the selected FOV and a classification channel 11 which classifies patterns (i.e., associates a name with each pattern) located in the FOV according to known classes of objects. For example, the location channel may detect the existence of a pattern in the lower left corner of the FOV and the classifier may identify the pattern as that of the class of objects known as an automobile.

THE CLASSIFICATION CHANNEL

The classification channel consists of a Lateral Geniculate Nucleus (LGN) module 30 which receives the input image pixel values and performs initial processing of the image. Module 30 feeds three other modules: a visual area 1 (V1) module 56, a visual area 2 (V2) module 32, and a sum module 54. These three modules perform further detailed processing and generate pattern size, orientation, and location information about the image which is conceptually arrayed along a "frequency" spectrum 72. The information in the spectrum is passed to an Inferior Temporal Cortex 1 (ITC1) module 58 and then to an Inferior Temporal Cortex 2 (ITC2) module 66 which classify the pattern and provide the classification results to a store 68. The modules of the classification channel are also assigned numbers on FIG. 2 (such as A17, A18) which correspond to well-known Brodmann areas of the human brain with similar functions. The classification channel uses a feedforward architecture so that the signal flows in a forward direction from the input image to the classification module 66.

LGN MODULE

Referring again to FIG. 1, for purposes of identifying the location of a pattern within the image, the array of image pixels is organized into 9 windows 14*a* . . . 14*i*, each containing a 175 by 175 array of pixels. Processing proceeds window by window and each window represents a FOV within the image. The location channel operates on one window at a time.

Returning to FIG. 2, by a mechanism to be described below, the location channel 9 determines the location within the window presently being processed (the active window).at which any pattern lies and conveys this location to the classification channel by a location value 21. The location value provides a row index and a column index for positioning the 175 by 175 bit window within the 525 by 525 input image.

When a pattern has been located, the location value and a 1-bit window enable signal 23 cause a row and column select unit 25 to indicate to LGN 30 that a pattern has been found and is located in a window whose position is specified by the value. The active window 27 (i.e., the FOV) is then shifted to a revised location within the image (note, for example, the shifted window 17 in FIG. 1). The pixels within the shifted window are then processed by a calibrate unit 34 and a normalize unit 36 to distribute their intensities across a gray-scale. The resulting preprocessed window 37 is then sent to the later modules.

The calibrate unit calculates a histogram of the pixel values of the pattern within the selected (active) window. For the 8-bit pixels in the example, the histogram is typically concentrated in a sub-band within the total possible range of 0 to 255. The calibration unit spreads the histogram over the entire 0 to 255 range by linearly mapping the histogram values in the sub-band to the values 0 to 255, with the lowest value in the sub-band being mapped to 0 and the highest value in the sub-band being mapped to 255. The lowest value of the histogram sub-band is defined as the value where the number of pixels falls to 1% of the cumulative number. The highest value of the histogram is defined as the value where the number of pixels first exceeds 99.25% of the cumulative number. The normalize unit then rescales the pixel values by dividing each of them by 255 so that all pixel values leaving the LGN module are in the range from 0 to 1. In FIG. 2, the [0,1] indicates that the values lie between 0 and 1.

(V1) MODULE

Referring again to FIG. 1, in the V1 module, the active window is further subdivided into 625 subwindows 42 each having an array of 7 by 7 pixels (the subwindow 42 in FIG. 1 is shown at a much larger scale than the window 38 from which it came, for clarity). Returning to FIG. 2, in the V1 module, the window is first fed to a spiral map module 62 which performs a spiral mapping of the 625 subwindows, taking the upper left hand subwindow first (i.e., subwindow 40 of FIG. 1), then the other subwindows in the top row from left to right, then the subwindows in the right column from top to bottom, then the bottom row, left column, second row, and so on, finally ending with the center subwindow. The subwindows are then delivered one by one in the spiral order to the visarea 1 unit 63.

In visarea 1 each 7 by 7 pixel subwindow is processed to generate measures of the visual strengths of the edges of the patterns in the horizontal, vertical, and two 45 degree diagonal directions. For gray-scale images visarea 1 generates measures of the magnitude of the luminance gradient in the four directions. For binary (1-bit pixel) images measures of the edge orientation in the four directions are generated.

Figure 4:
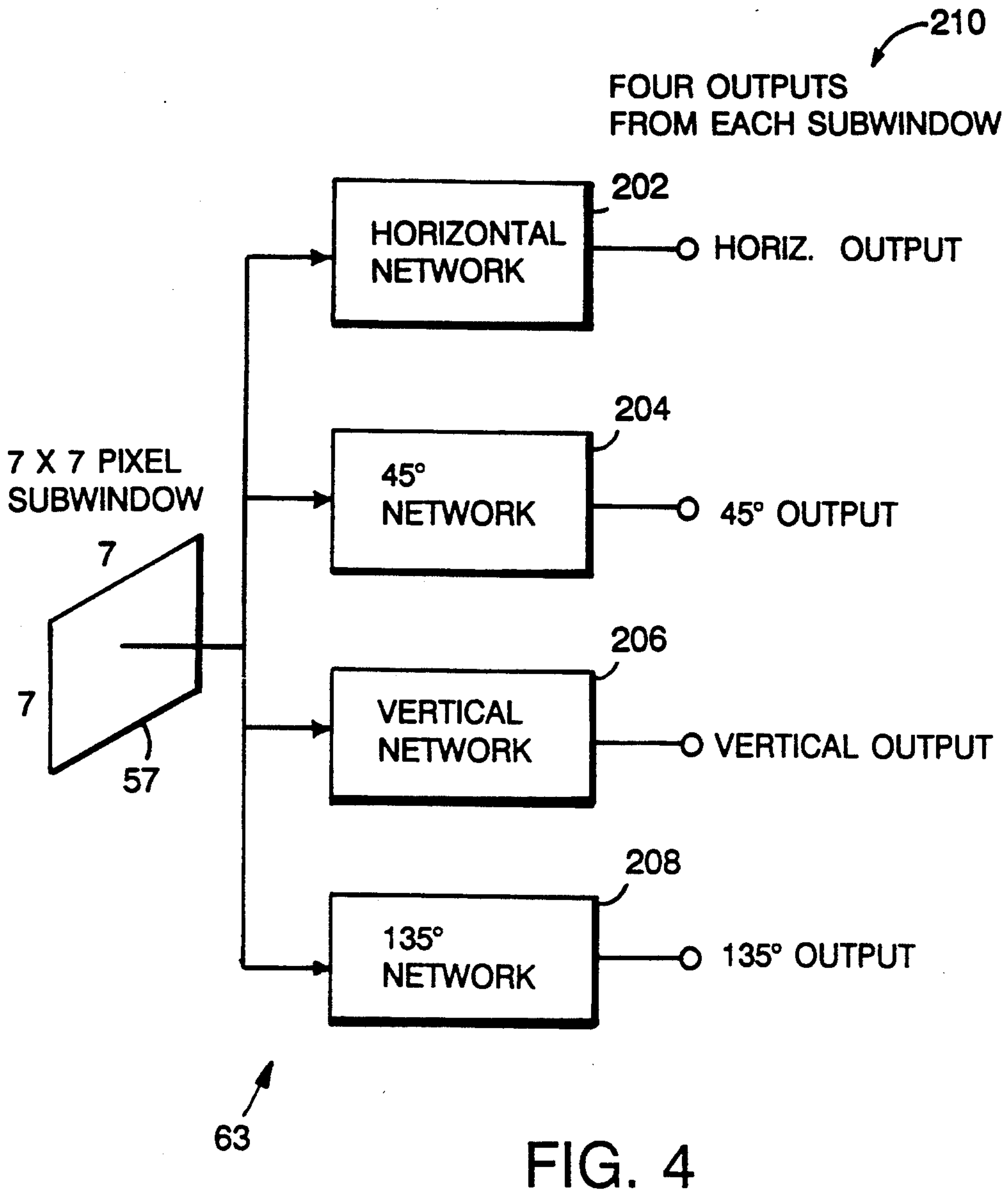
FIG. 4 is a diagram of edge recognition networks.

Referring to FIG. 4, each edge measurement is performed for each 7 by 7 subwindow by a cooperative-competitive neural network which has 25 hidden neurons and one output neuron. Visarea 1 thus includes four neural networks 202, 204, 206, 208, each of which receives the pixels of each subwindow 57 and generates one of the outputs 210. As in biological systems, each neuron can be either an excitatory-type or an inhibitory-type, but not both simultaneously. There are 1924 fixed interconnection weights for each network.

A set of actual interconnection weights useful for the four networks for the example are set forth in Appendix A. Each of the detectors is a three layer neural network having an input layer, a hidden layer, and a single output neuron. Appendix A includes two sets of four matrices each. One set of four matrices (marked horizontal) is used for the horizontal and vertical detectors; the other set of four matrices (marked diagonal) is used for the 45 and 135 degree detectors. In each set, the four matrices A, 3, C, and D contain interconnection weight values respectively for interconnections within-the hidden layer, interconnections from the input layer to the hidden layer, interconnections from the hidden layer to the output neuron, and interconnections from the input layer to the output neuron. Each row in a matrix represents all of the interconnections from a given neuron, and each column represents all of the interconnections to a given neuron. The diagonal of the A matrix thus represents all of the interconnections of hidden layer neurons with themselves. The matrices labelled horizontal may be used as the vertical edge detector simply by flipping the input 7 by 7 subwindow about its diagonal axis. The matrices labeled 45 degrees similarly may be used to detect 135 degree edges simply by flipping the input 7 by 7 subwindow about its horizontal axis.

For the general case of detecting gradients of luminance (instead of simple binary edges), detectors are designed using the genetic algorithm in the manner described in the copending patent application cited below, for a particular orientation and gradient direction. The responses to orientations of 90 degrees or larger and/or gradients in the opposite sense can use the same detector weights if the input 7 by 7 subwindow are properly rotated first. The rotations are performed in visarea 1.

The interconnection weights between neurons remains fixed. The orientation measurements of luminance lines and gradient magnitudes model similar processing that occurs in biological visual systems. A technique for determining the interconnection weights for the neural network is set forth in copending U.S. patent application Ser. No. 468,857, filed on the same day as the parent of this application, and incorporated by reference.

Figure 5:
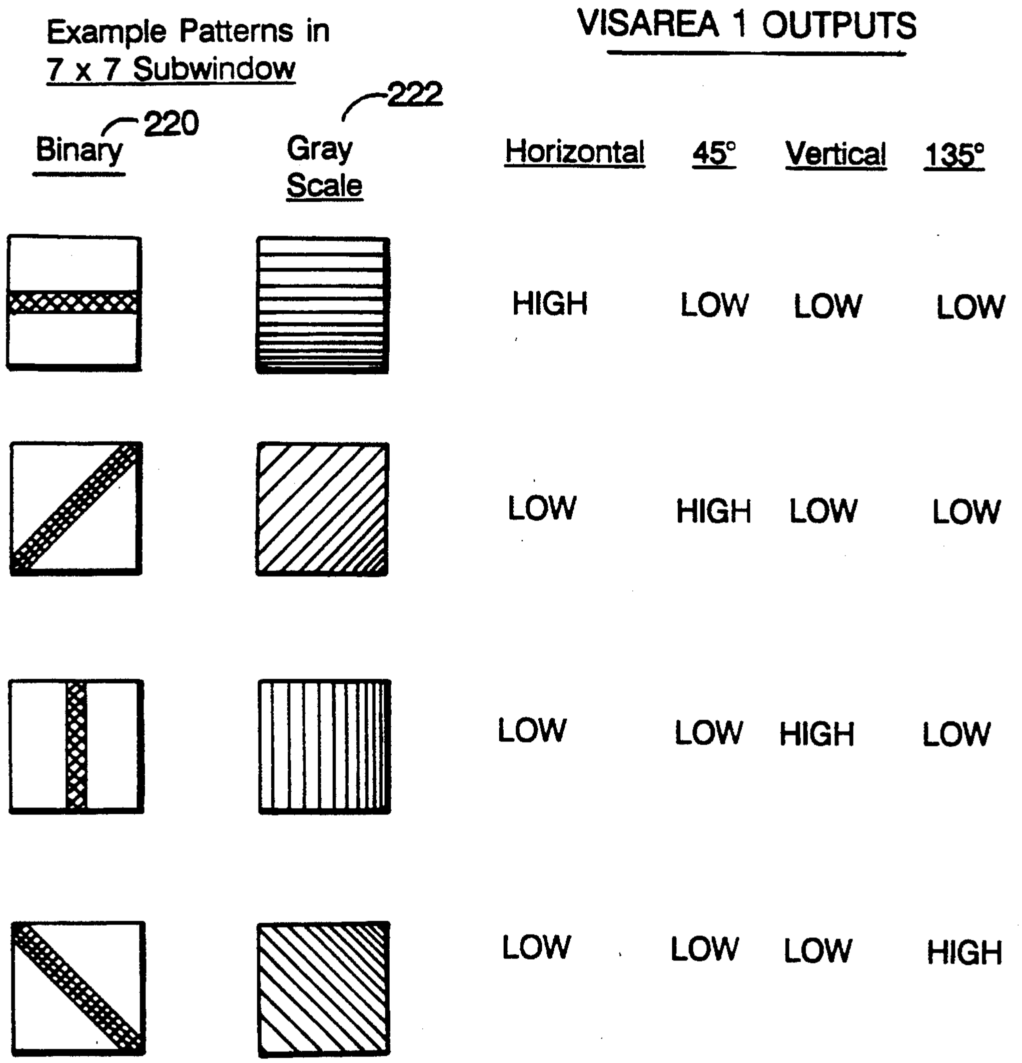
FIG. 5 is a table of possible outputs for example input edge patterns.

Referring to FIG. 5, binary edge patterns of the kinds shown in column 220 and gray-scale patterns of the kinds shown in column 222 would produce visarea 1 outputs as shown. In the gray-scale patterns each line represents pixels of constant value. The indicated gradient in the pattern can be reversed without affecting the visarea 1 outputs.

As explained below, object classification is done in part on the basis of these orientation strengths over a set of subwindows. In the preferred embodiment, there are no 'corner,' 'circle,' 'face,' or 'matched' filter detectors of the kind commonly used in other machine vision approaches-to recognize features of a pattern.

In the example, the four orientation signals generated by visarea 1 for each of the 625 7 by 7 pixel subwindows yields a total of 2500 orientation values for the entire window.

Figure 3:
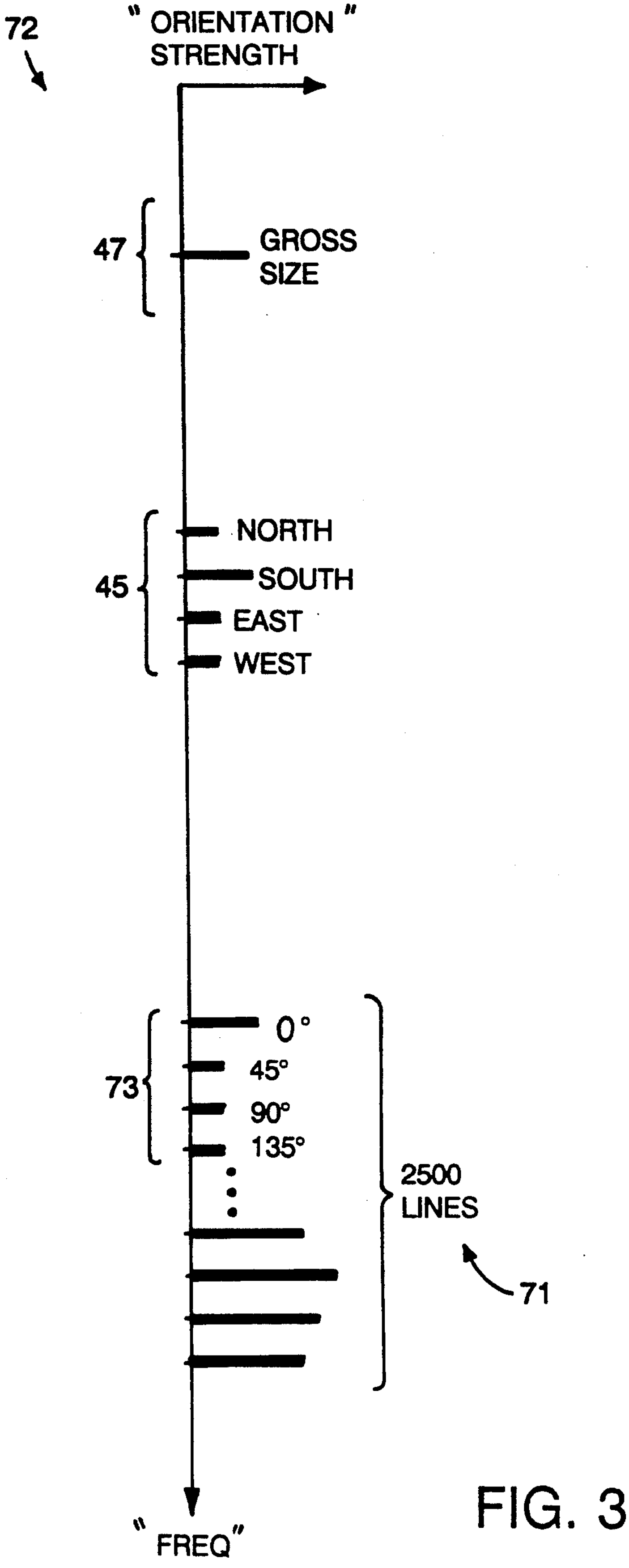
FIG. 3 is a diagram of a spectrum of pattern information.

Referring again to FIG. 3, the 2500 orientation signal values 71 generated by visarea 1 can be arrayed as lines on a spectrum 72 in which the length of each horizontal line represents the magnitude of the signal. The positions along the spectrum may be thought of as corresponding to different "frequencies". The orientation signal lines for each window are arranged in order as shown, and the successive subwindows in the spiral order are arranged in order along the spectrum so that the first subwindow's lines appear first. Thus, the outer subwindows of the windowed image are nearer the top of the spectrum (lower frequency) and the inner subwindows are nearer the bottom. Hence, information about the general shape of the pattern occurs at the top or low frequency part of the output spectrum, and information about the interior of the pattern occurs at the bottom or high frequency part of the spectrum.

VISAREA 2 MODULE

Figure 6:
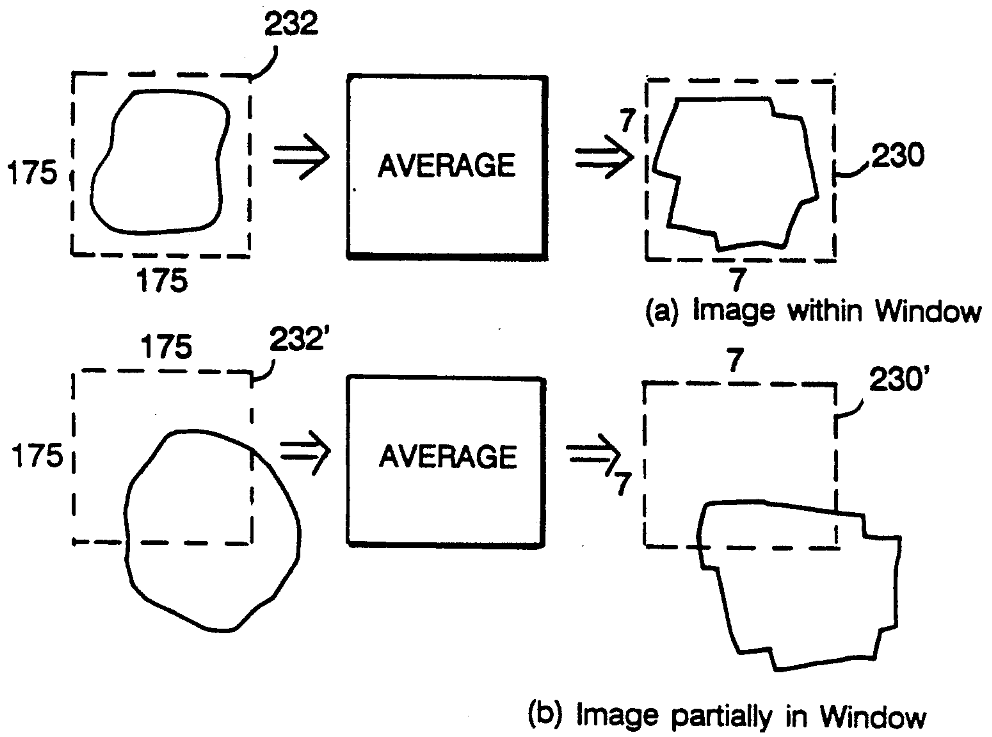
FIG. 6 is a diagram of the effect of window averaging.

Referring again to FIG. 2, the second feature-generating module in the classification channel is visarea 2 module 32. The function of this module is to detect edges near the perimeter of the 175 by 175 pixel window. Since only the outside edges of the pattern are of interest in this step, the window image is first defocused by a 25 by 25 average unit 49. Referring to FIG. 6, this averaging smears details of the pattern (the detail is captured by visarea 1), but retains the necessary outside edge information. The averaging produces a single smeared 7 by 7 pixel image 230, 230′ of the pattern in the 175 by 175 window 232, 232′. As shown, the averaging simplifies the pattern edges to enable them to be easily detected.

Figure 7:
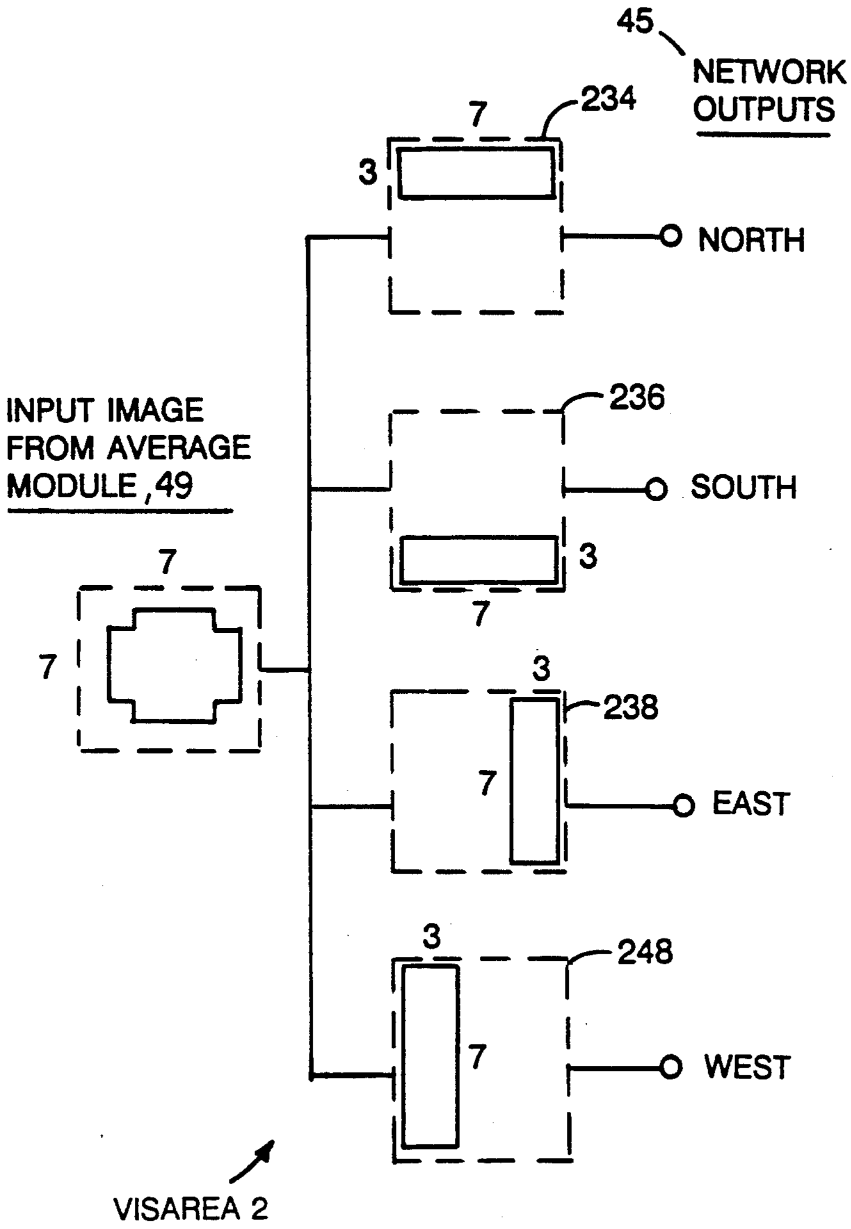
FIG. 7 is a diagram of edge recognition functions.

Referring to FIG. 7, visarea 2 includes four neural networks, 234, 236, 238, 240, each of which detects the presence or absence of an edge. Two 3 by 7 pixel detectors 234, 236 detect the presence of nearly horizontal edges respectively at the top and bottom of the window image. Two 7 by 3 pixel detectors 238, 240 detect the presence of nearly vertical edges respectively at the left and right of the window image. These edge detectors are like the ones in visarea 1 except the input images are now 7 by 3 or 3 by 7 instead of 7 by 7. Each detector uses 25 neurons with fixed interconnection weights.

A set of actual interconnection weights for these four neural networks are set forth in Appendix B. Only one set of four matrices is provided; these may be used in all of the four different detectors simply by rotating the input 7 by 7 subwindow by 45, 90, or 135 degrees as the case may be.

For most objects of interest that fit in the 175 by 175 window, there will be edges on the top and bottom and on the right and left sides. The output of the visarea 2 unit is four spectrum lines 45 which measure the north, south, east, and west edge strengths. These four lines also comprise part of the spectrum 72 used by the classifier.

Figure 8:
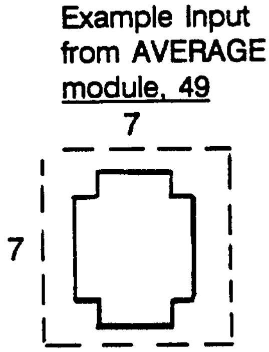
FIG. 8 is a table of edge recognition network outputs.
Figure 8:
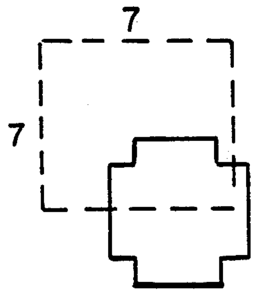

Referring to FIG. 8, for a pattern in the center of the output of the average module, the four network outputs of visarea 2 are all high, while for a pattern in the lower right corner, the north and west outputs are low while the south and east outputs are high.

SUM MODULE

The third feature-generating module is a sum module 54. This module sums the pixel values in the 175 by 175 pixel window. The computed sum is a measure of the gross size of the pattern in the window and it is used as one of the input spectrum values to the classifier (note reference numeral 47 on FIG. 3).

CLASSIFICATION SPECTRUM

Referring again to FIG. 3, classification is achieved by interpreting a combination of the visual feature measures discussed above. Note that these feature measures include some values which have been only slightly processed (the output of the sum module), some moderately processed (the output of the visarea 2 module), and some highly processed (the output of the visarea 1 module). Because the spectrum includes lines from visarea 1, from visarea 2, and from sum, the magnitudes of the lines are adjusted by each module to ensure appropriate comparative weighting of each module's output. In one example, the visarea 1 module outputs are adjusted by subtracting the minimum (usually negative) of all of the visarea 1 outputs from each of the visarea 1 outputs to ensure that the visarea 1 portion of the spectrum is entirely positive with a minimum value of zero. The visarea 2 and sum outputs are multiplied by scale factors which depend on the window size used in LGN 30 (FIG. 2). For a window size of 175 by 175, the scale factors are 0.1 for the visarea 2 outputs and 0.01 for the sum module output. For a window size of 42 by 42, the factors are 1.5 and 0.3 respectively. This weighting ensures that the classifier gives equal significance to information about size, edges, and detail structure.

ITC1 MODULE

Referring again to FIG. 2, classification is done, using the spectrum 72 of information, by an unsupervised classifier 58 followed by a supervised classifier 66. The unsupervised classifier ITC1 module uses the ART 2 classifier technique discussed in G. Carpenter and S. Grossberg, "ART 2: Self-organization of Stable Category Recognition Codes for Analog Input Patterns," Applied optics, Special Issue on Neural Networks, (1987), incorporated herein by reference.

In neural network theory terminology, the input spectrum is "impressed" on the bottom layer of the ART2. This classifier automatically selects characteristics of the input spectrum (or pattern) to define a category. Subsequent patterns are compared to patterns stored in the long-term memory (LTM) trace 59. ART2 is a two-slab neural network. One slab is called F1 and consists of 3 interacting layers which perform noise filtering and signal enhancement. The second slab is called F2 and consists of a single interacting layer. The F2 neurons are used to indicate by their activity the category of the input pattern. The input patterns, after processing by Fl are judged to be close or far from the LTM traces. If a new input spectrum is different from previous spectra, then a new category is defined for the input. If a new input spectrum is similar to a previous category class, then the existing category is updated with an additional example. The classifier is 'trained' by presenting to it a sequence of example patterns which are then categorized by ITC1. In principle, if the examples are sufficiently different, a distinct category will be defined for each example. If some of the examples are similar to one another, then a smaller number of categories are defined.

The definition of ART2 and its operating characteristics are well-known. It is selected over other classifiers such as Hopfield nets and perceptrons because of its feature enhancement, noise reduction, and stability properties.

Within ITC1, the orient unit 250 determines the closeness of the match between the input and a stored pattern based on a positive number $||R||$ generated by F1. If the match is not close then it causes a search of the F2 categories for a closer match. The confidence unit 252 associates the closeness measure $||R||$ with a confidence level as defined by the user. For example, if $||R||=1.0$, then the confidence level is 100% and if $||R||=0.7$, then the confidence level is 50%, with a linear interpolation for $||R||$ greater than 0.7 and less than 1.0.

ITC2 MODULE

After training the ITC1 module, its output nodes 61 correspond to examples of input patterns from particular categories or classes. For example, if the first ten examples are trucks, the first ten ITC1 output nodes are in a category (say category 1) that corresponds to trucks. The ITC2 module 66 then associates the activation of any of the first ten nodes with the name 'truck'. This is implemented by a simple logical OR operation. In similar fashion, other categories of objects are learned by ITC2 and associated with other names.

In practice, it is desirable to store the identification and locations of patterns found in the FOV for future reference. The decision to store a pattern is made by using the matching parameter 109 of ITC1 as a measure of confidence in the pattern identification. By setting the confidence level 67 equal to 50% when the match just passes a predetermined threshold for a category match and to 100% when the match with a LTM trace is perfect, a confidence measure is generated. ITC2 decides 69 whether the identification is accurate enough for a given application. If the confidence level is high enough 71, then the results are stored in store 68. The information stored is the class name 73, the confidence level 75, and the location 77 in the FOV. If the confidence level is not high enough, then the system tries to identify the pattern by evaluating the input image again, as explained below.

LOCATION CHANNEL

The function of the location channel is to isolate an individual pattern in the FOV so that the classification channel processing can be applied to that pattern. The location channel includes a Superior Colliculus (superc) module 18, and also includes the LGN, visarea 2, and Posterior Parietal Cortex (PPC) modules. The location channel supports both feedforward and feedback flows of signals.

SUPERC MODULE

Locating individual patterns within the FOV (active window) involves a two-stage process consisting of coarse location followed by fine location and pull-in. The superc module performs the coarse location procedure. In this module a modified ART2 neural network is used to grossly locate objects of interest within the FOV. The F2 slab of the ART2 is used to impress a stored LTM trace on the top layer of the F1 slab. LTM traces for the general shapes of interest are computed off-line and stored in the superc. In this F2-to-F1, the system is 'primed' to locate a particular class of objects.

A 175 by 175 pixel window is extracted from the input image and impressed on the bottom layer of the ART2. The pattern specified by the LTM trace 19 is compared to the windowed image. The LTM trace is designed so that an object of the correct general size will cause a match, even if off-center, to indicate its presence. A row map unit 24 is used to map the windowed input to the ART2 input. Because the input window is 175 by 175, there are 30,625 input pixels delivered to the ART2. If no match is found, than another non-overlapping window in the image is input as the active window and evaluated for the presence of an object. Thus, in the example, there are nine coarse location positions, each represented by one of the nine non-overlapping windows in the image. The degree of match between the image pattern and the LTM traces is used as an enable signal 23 to the LGN module. The selection of the coarse window position from among the nine possible windows is done by a fovea move unit 20. The coarse position 22 is sent to the row map unit, and to the PPC module for further adjustment.

PPC MODULE

The second stage of the location process is the fine adjustment and pull-in stage. This pull-in stage is done by a feedback path which includes the LGN, visarea 2, and PPC modules. The function of the LGN and visarea 2 modules was described above. In the PPC module 28, the center of attention, or fovea (i.e., the location of the center of the active window) is adjusted to center the window on the pattern of interest. Referring again to FIG. 1, for example, the object 12 is not centered in any of the nine original windows of the image. By shifting window 14e to location 17, the object pattern is made to lie in the center of the window as shown by reference numeral 50. The centering function evaluates the outputs of visarea 2, i.e., the strength of the four edges of the window, which are sent to PPC on lines 81.

When an object is centered, the strength of the edge measurements will be about equal. If the object is only partially in the window, then one or more of the edges will be missing and the corresponding edge strength will be small. The window is moved in a direction that will tend to equalize the edge strengths.

The fovea delta 1 unit 46 in the PPC implements the control law for moving the window. One possible control law is a standard bang-bang rule with a dead-zone for the vertical and horizontal directions. Under the bang-bang rule, for vertical movements, the difference in the north and south outputs from visarea 2 is computed. If the difference is larger than a positive threshold or smaller than a negative threshold, then the window is moved a fixed amount vertically, up or down depending on the sign of the difference. For example, if north—south is positive and larger than the positive threshold, then the window is moved vertically down a fixed amount; if the sign is negative and smaller than the negative threshold, then the window is moved vertically up the same fixed amount. The magnitude of the movement is constant regardless of the magnitude of the north—south difference, i.e., when movement occurs the maximum amount is used (bang-bang). When the difference is intermediate between the positive and negative threshold (dead zone), then no vertical movement of the window is made. For horizontal movements a similar rule is implemented using the east and west visarea 2 outputs.

The output of the fovea delta 1 box is the magnitude of adjustment for the location in the vertical and horizontal directions, and is fed to the fovea adjust unit 83. The fovea adjust unit adjusts the value provided by the fovea move unit 20 and delivers the current location values in the horizontal and vertical directions on line 21. Adjustments may be made one pixel at a time in either direction.

A second pull-in path includes the LGN, visarea 2, ITC1, ITC2, and PPC modules. This path is used to take additional looks at an object when the confidence in pattern identification is low. If the confidence level is judged to be insufficient, then an enable signal 99 from ITC2 activates a fovea delta2 unit 68 in PPC. This unit generates a random adjustment of the window in the vertical and horizontal directions. This random adjustment gives the system a second chance to achieve a better pattern classification. A counter in ITC2 (not shown) is used to limit the number of retries. After some preset number of retries, the system stores the object's conjectured identity together with the confidence level and location, and then goes on to search for other objects.

After processing the windowed image and storing the results, a slew enable signal 101 is used to activate the fovea move unit 20 to move to the next coarse position, i.e., to the next one of the nine windows in the original image.

The system has been implemented in a computer simulation written in the C language, and compiled and run on a combination SUN 4/110 and CONVEX 220 computing system (using SUN's version 4.03 C compiler or CONVEX's version 3.0 C compiler). Copies of the source code are attached as Appendix C. Appendix C is subject to copyright protection. The copyright owner has no objection to the reproduction of Appendix C as it appears in the United States Patent and Trademark Office, but otherwise reserves all copyright rights whatsoever.

SYSTEM DYNAMICS

In a computer simulation of the object recognition system, the system functions are executed in a sequential manner. First, the location channel finds and centers in a window an object of interest. When an object straddles evenly between two windows, the choice between which window will be used for the analysis depends on numerical runoff errors and appears random to the user. Then the classification channel identifies the object.

In a parallel implementation with custom hardware, the modules would run simultaneously. The sequencing of functions would be controlled by enable signals, as described above, and by properly selecting the neural network interconnection time constants. Time constants associated with the location channel's LTMs are short so that the channel will converge quickly to the location which is to be analyzed. The classification channel's LTM time constants are longer and the identification process is comparatively slow. This difference in the time constants ensures that classification is done on a centered object. Possible time constants would be such that the ratio of location time to classification time would be from 1:3 up to 1:10 or more. The exact time would depend on the nature of the application including the size of the input images, and grayness.

PAP SMEAR APPLICATION

The screening and interpretation of cervical exfoliative (Pap) smears is one application of the object recognition system. Manual analysis of such smears by a cytologist is time consuming. By applying the object recognition system to Pap smear analysis, automatic prescreening of smears should be possible, saving time and money.

Figure 9:
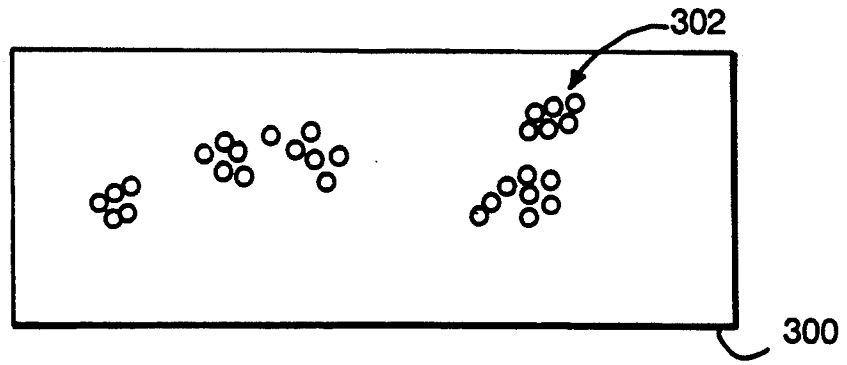
FIG. 9 is a top view of a slide of a Pap smear.

Referring to FIG. 9, in a typical Pap smear, a glass slide 300 is smeared with a sample of cervical cells 302 (only a small representative sample of cells is shown). The number of cells on the slide may be on the order of 20,000–100,000. The cytologist's task is to scan the cells on the slide using a microscope and to identify and analyze the condition of non-normal cells.

Figure 10:
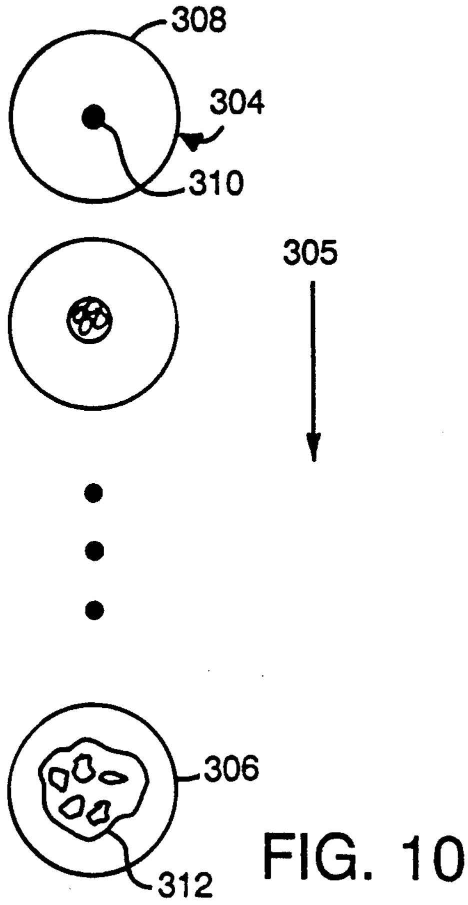
FIG. 10 is a chart of cervical cells.

Referring to FIG. 10, each cell can be categorized as lying at some position along a continuum 305 from a normal cell 304 to a malignant cell 306. In general, the cells hive generally the same size (bounded by a cell wall 308), regardless of their location along the continuum, but there are differences, among other things, in the size, configuration, and appearance of the cell nucleus 310 and in the roughness or smoothness of the outer cell boundaries, as well as Possibly other cytoplasmic features. In a normal cell, the nucleus 310 is small, has smooth, curved boundaries, and a uniform dark appearance. In a malignant cell 306, the nucleus 312 is much larger, has irregular boundaries, and is blotchy in appearance.

The cytologist is expected to be able to detect as few as two or three non-normal cells on the slide for purposes of diagnosing cervical cancer. Even highly accomplished cytologists cannot achieve a false negative analysis rate much lower than about 10% (i.e., 10% of the smears which contain abnormal cells are incorrectly found to be normal). It is expected that the use of the object recognition system can improve this rate significantly.

In general, to use the object recognition system for Pap smear analysis, one first trains the system by presenting it with some selection of known cells; then the system is used for analysis by presenting it with a Pap smear and allowing the system to scan the smear to detect cells and their normal or abnormal conditions.

Figure 11:
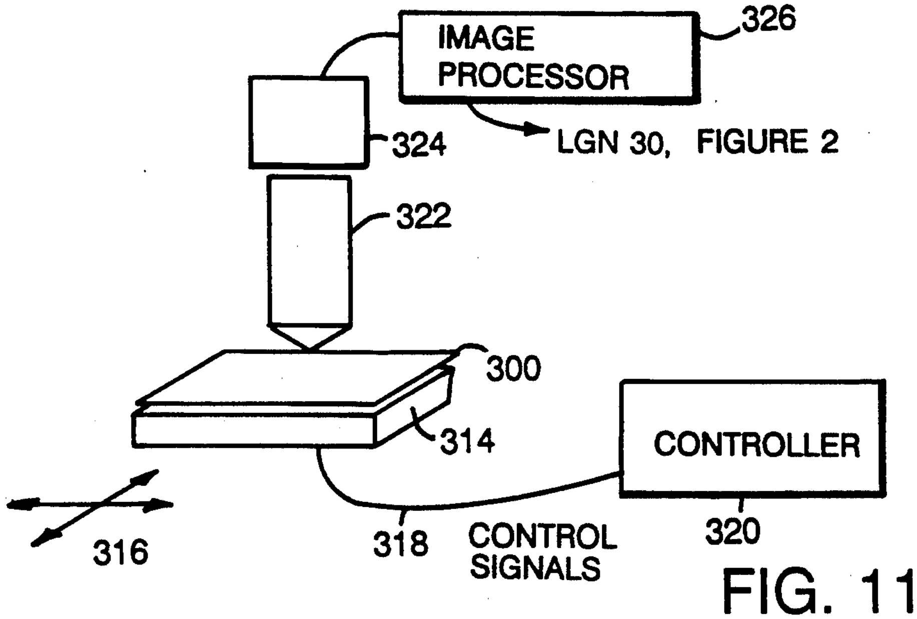
FIG. 11 is a schematic view of a microscope and stage and related electronics for examining the Pap smear.

Referring to FIG. 11, in order to acquire a digitized version of an image of cells in the smear, the slide 300 is mounted on a stage 314 which can be driven by motors (not shown) along two dimensions 316 under the control of signals 318 delivered from a controller 320. A microscope 322 focuses the image on a video camera 324 which feeds an analog signal to an image processor 326. The image processor forms a 525 by 525 pixel digitized image and delivers it to the LGN 30 (FIG. 2).

Figure 12:
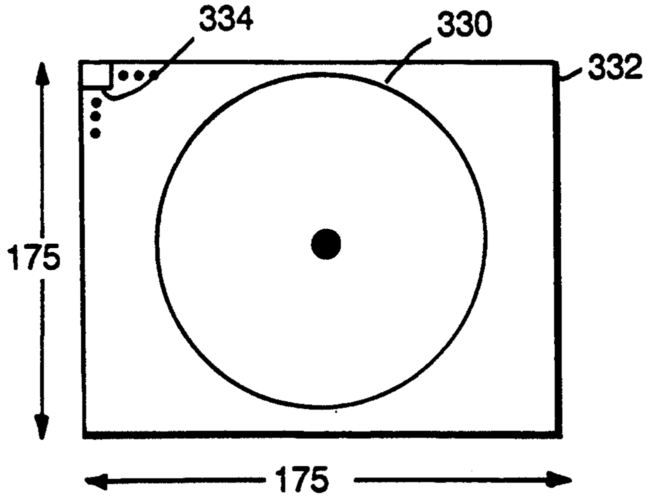
FIG. 12 is a diagram of a cell within a window.

Referring to FIG. 12, for training, the operator uses the microscope and the image processor to select a single cell 330 and enlarge the cell to a scale that fills an entire 175 by 175 pixel window 332 within the image. This image is presented to the system and results in a spectrum which is classified by classifier 58 as one node of a first category 61 (FIG. 2). The spectrum is based on the array of 625 subwindows 334, each 7 by 7 pixels, which tile the window. The 2500 output lines of block 63 in FIG. 2 are then arrayed along the spectrum such that the lines pertaining to the cell nucleus are at the higher "frequency" end and the lines pertaining to the cell boundary are at lower "frequencies".

The operator then indicates to classifier 66 the name to be associated with that category. For example, the first cell presented to the system for training may be a normal cell and becomes the first node of a NORMAL category 61 (FIG. 2). Additional normal cells could be presented and would form other nodes in that category. In a simple scheme, there would be only two categories, NORMAL and ABNORMAL, although several other intermediate categories could also be used.

Once the system is trained, the operator may load a slide of a smear to be analyzed onto the stage. The controller will move the stage to a starting position say at the upper left corner of the slide and the camera will deliver an image of that portion of the slide to the system via processor 326. The scale of the image will be such that the cells are each about the size of a 175 by 175 pixel window. Of course, the cells will not generally be found in the centers of the windows. As previously explained, the system has a location channel and a classification channel which operate in parallel so that the system can locate a cell within the window and then adjust the field of view to center the cell. Then the cell can be classified automatically based on the prior training. The results are stored in the store 68. For a given cell, the store will hold an indication of whether the cell is NORMAL or ABNORMAL, a confidence level of that determination, and the location of the cell in the image. In operation, the SUM module analyses the gross size of the cell, the V2 module analyzes the edges of the cell wall to determine its shape, and the V1 module analyses the detailed configuration of the parts of the cell and their appearance, especially of the nucleus.

Next the stage is moved to a new location and the process is repeated. The controller 320 can keep track of the positions of the slide so that a particular cell can be automatically relocated based on the stage position and the location of the cell within the image taken at that position (stored in store 68). Thus the cytologist can quickly find and analyse the cells which the system has indicated are abnormal. The system thus saves the cytologist a great deal of time by preprocessing the slide to identify abnormal cells.

Figure 13B:
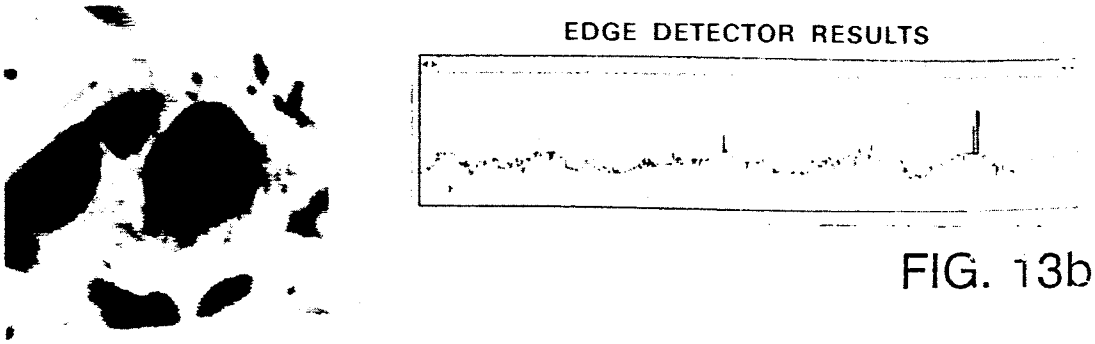

Referring to FIG. 13A, a normal cell produces an output of the edge detector which has sharp spikes representing the edges of the nucleus (note that the graph labeled Edge Detector Results represents only a small portion—about 25% of the highest "frequencies"—of the full spectrum of 2500 lines). The center subwindow of the image is represented by lines on the far right-hand side of the graph. A comparable figure for an abnormal cell is shown in FIG. 13B.

Referring to FIG. 14, in the full spectrum 350, the V2 components are given relatively greater strength than the V1 components and the SUM component is given relatively greater strength then the V2 components. The precise relative weights of the different components is achieved by applying to the raw SUM component a weighting factor of $10^{-1}$ and to the V2 components a weighting factor of 10. This weighting gives approximately equal value to the three types of information (gross size of the cell, general shape of the cell, and detailed features of the interior and exterior of the cell).

Training is done by exposing the system to a variety of known normal and abnormal cells. The classifier stores the pattern associated with each sample cell. When an unknown test cell is then shown to the system, its generated spectrum is passed to the classifier. The classifier will find the closest match to the known stored samples. The cell is then labeled to be of the same type as the closest stored sample.

Referring to FIG. 15, in one training technique, the system was shown a series of normal cells only (in this case 28 normal cells). Then the system was tested by showing it a sample of thirty-three test cells (17 normal and 16 abnormal). The system compared each test cell with known standards and made a yes/no decision based on a threshold of closeness to the normal standard cells. The chart illustrates that a tradeoiff can be obtained between the rate of false positives and the rate of false negatives, by adjusting the threshold from high to low.

FIG. 16 demonstrates that the false negative rate can be reduced by increasing the number of training cells.

Referring to FIG. 17, in yet another training technique, called selected training, one begins with a training set of both normal and abnormal cells. In a set of cells which are thereafter used for testing, those which produce false results are added to the training set in their proper categories. Curve 362 suggests that in this training regime, the addition of greater numbers of test cells causes a more rapid drop in the false negative rates. It is believed that using a set of test cells numbering say 1000 will be sufficient with a high level of confidence to reduce the false negative rate to an extremely small value.

Other embodiments are within the claims that follow the appendices.

Appendices A, B, C are attached.

APPENDIX A

HORIZONTAL

| | | | | | | | | | | | | | | | | | | | | | | | | |
|---|---|---|---|---|---|---|---|---|---|---|---|---|---|---|---|---|---|---|---|---|---|---|---|---|
| 0 | -6 | -10 | -1 | 0 | -2 | -1 | -3 | 0 | -2 | -1 | -7 | -9 | -5 | -7 | -6 | -3 | -2 | -6 | 0 | -1 | -8 | -1 | -1 | -7 |
| -2 | 0 | -7 | 0 | -1 | -6 | -3 | -6 | -2 | -6 | -7 | -3 | -6 | -8 | -5 | -2 | -7 | -3 | -8 | -5 | -5 | -1 | -1 | -10 | -3 |
| -9 | -7 | 0 | -4 | -9 | -7 | -8 | -8 | -9 | -7 | -4 | -10 | -3 | -8 | -7 | 0 | -6 | -10 | -2 | -2 | -8 | 0 | -10 | -1 | -10 |
| -10 | -3 | 0 | 0 | -7 | -7 | -5 | -3 | -2 | 0 | -9 | -1 | -9 | -8 | -5 | -1 | 0 | -6 | -10 | -4 | -5 | -5 | -8 | -10 | -6 |
| -9 | -1 | -9 | -9 | 0 | -4 | -4 | -10 | -6 | -2 | -9 | 0 | -4 | -6 | -4 | -3 | -6 | -3 | -1 | -7 | -3 | -6 | -8 | -10 | -5 |
| 0 | -7 | -6 | -6 | -7 | 0 | -4 | -6 | -8 | -1 | -5 | -2 | -7 | -2 | -7 | -6 | 0 | -8 | 0 | -2 | -10 | -5 | -8 | -7 | -2 |
| -10 | -10 | -7 | 0 | -8 | -4 | 0 | -1 | -8 | -10 | -1 | -3 | -6 | -5 | -8 | -4 | -8 | -10 | -10 | -4 | -9 | -4 | -2 | -4 | -2 |
| -2 | -2 | -3 | -10 | -6 | -6 | -7 | 0 | -6 | -8 | -7 | -7 | -5 | -3 | -7 | -10 | -3 | 0 | -5 | -3 | -9 | -1 | -6 | -6 | 0 |
| -9 | -4 | -6 | -4 | -9 | -7 | -4 | -6 | 0 | -6 | -9 | -9 | -1 | -4 | -1 | -8 | -4 | -8 | -4 | -5 | -8 | -8 | 0 | -3 | -3 |
| -5 | -1 | -1 | -7 | 0 | -10 | -7 | -2 | -4 | 0 | -5 | -7 | -2 | -4 | -8 | -10 | -7 | -1 | -8 | -4 | -4 | -2 | -7 | -4 | -6 |
| -8 | -10 | -5 | -2 | -5 | -9 | -7 | -5 | -1 | -9 | 0 | 0 | -3 | -7 | -1 | -6 | -9 | -4 | -8 | -4 | -2 | -3 | -10 | -3 | -9 |
| -2 | 0 | -5 | -3 | -5 | -4 | -2 | -5 | -5 | -4 | -9 | 0 | -4 | 0 | -8 | -10 | -6 | -5 | -7 | -4 | -6 | -7 | 0 | -10 | -2 |
| -2 | -8 | -10 | -5 | -7 | -4 | -9 | -2 | -10 | -3 | -10 | -9 | 0 | -3 | -1 | -10 | -1 | 0 | -4 | -8 | -2 | -7 | -7 | 0 | -5 |
| -2 | -7 | -9 | -6 | -2 | -2 | 0 | 0 | -7 | -3 | -8 | -4 | -10 | 0 | -3 | -6 | -5 | -2 | -4 | -9 | -5 | -3 | -1 | -2 | -8 |
| -2 | 0 | -9 | -5 | -9 | -5 | -10 | -10 | -10 | -1 | -5 | -4 | -5 | -3 | 0 | -3 | 0 | -7 | -8 | -5 | -5 | -9 | -3 | -2 | -4 |
| -10 | 0 | -3 | -4 | -3 | -4 | -5 | -3 | -9 | -2 | -6 | -4 | 0 | -10 | -7 | 0 | -3 | -9 | -5 | -5 | -9 | -3 | -10 | -3 | -9 |
| -5 | -4 | -3 | -5 | -8 | -8 | -9 | -10 | -9 | -6 | -4 | -7 | -2 | -1 | -4 | -5 | 0 | -9 | -10 | -2 | -8 | -4 | -1 | -5 | -9 |
| -1 | -2 | -3 | 0 | -4 | -2 | -9 | -10 | -6 | -4 | -10 | -8 | -6 | -9 | -4 | -9 | -7 | 0 | 0 | -10 | -5 | 0 | -10 | -3 | -2 |
| -10 | -7 | -6 | -3 | -4 | -7 | 0 | -2 | -3 | -1 | 0 | -3 | -8 | -5 | -6 | -9 | -3 | -2 | 0 | -8 | -1 | -7 | -4 | -8 | -7 |
| -6 | -6 | -4 | -6 | -9 | -1 | -3 | 0 | -8 | -9 | -7 | -2 | -8 | -3 | -1 | -9 | -6 | -5 | -8 | 0 | -8 | 0 | -4 | -4 | -5 |
| -9 | -10 | -5 | -6 | -3 | -8 | -1 | -7 | -3 | 0 | -3 | -6 | -2 | -5 | -5 | -8 | -1 | -6 | -1 | -9 | 0 | -2 | -5 | -5 | -7 |
| -5 | -6 | -2 | -3 | -9 | 0 | -7 | -6 | -2 | 0 | -1 | -4 | -10 | -10 | -4 | -5 | -6 | -5 | -7 | 0 | -9 | 0 | -5 | -5 | -2 |
| 0 | -4 | -3 | -10 | -5 | -1 | -5 | -1 | -6 | -8 | -2 | -4 | -8 | -4 | -10 | -10 | -1 | -7 | 0 | -8 | -3 | -10 | 0 | 0 | -7 |
| 0 | -2 | -7 | -8 | -7 | 0 | -10 | -10 | -8 | -7 | -1 | -9 | -1 | -4 | -10 | -4 | -10 | -8 | -8 | -10 | -4 | -3 | -7 | 0 | -4 |
| -6 | -3 | -2 | -8 | -10 | -1 | -1 | -10 | -9 | -6 | -5 | -2 | -7 | -10 | -3 | -8 | -5 | 0 | -4 | -8 | 0 | -7 | -8 | -7 | 0 |

Final A matrix Size = 25x25

HORIZONTAL

```
 40 70 50 70 10 70  0 50 10 80 80 60 50 10100 70 70  0 10100 90 10 80100 90
 60100 20 50  0 80 80 60100 70 70 90 70100 80 80 40  0 90 50  0 10 60 30 90
 10 90 50 70 20  0 20 80 40  0 60 70  0 70 60 50100 30 70 30 70 20 70 70 30
 60 60 40 70 70 20 40100 10 70 50 30  0 50 10 70100 30 20 20 30 50 50 40 50
  0 40 60 40 20100 90 50100 30 30 10 80 10 50 40 80 60  0 40 40  0 30 10 50
 30 60 10 60 30 60 30  0 10 80 40 10 20100 60 60 60 20 20 70  0 40 10 80 90
 40 60100 60 10 60 10100  0 40  0 80 50 10  0 10 90 80 10 90 80 90  0 30 60
 80 60 20 20 90 40 10 30 70 20 10 20 30100100 30 30 40  0 60  0 50 90 50 60
 10 80 70 50 80100100 10100 60 80 90100 70  0 70 80 40 30100 40 20  0 70 60
100 60100 70 80 20  0 50 80  0 50 80  0 60 80 20 70 70100 40 50 60  0  0  0
100 90 70 10100 50100  0 80 70 40 90 20 70 90 60 10 80 90 30 50 10 20  0 20
100 20 40 60 60 50 90 60 20 40 60 40100 80 70 10100 40  0 30 10 60 10100 70
 90 60 60 80  0 60 10 80 40 50 20 10 90100 70 80 60 90100100 80  0  0  0 30
 40 10100 60 60 30 60 50 20  0100 50 70 60 40100 80 40 30100 60 80 90 20 40
 60 40 30 40 50 40 70 20 40  0 60 20 90 10 70 90 80 10 40 20 20 20 40100 10
 80 20 80 40 90 90 60 20 50 80 20 70 70 60 60100100100 70 10 70 30  0 80 90
 40 70 60 80  0100 60 40100100 20 70 80 60 70 70 40 10 80 70 20100 90 40 20
 30 10 10100  0 90 60100 60 80 50100 10 40 70 50 50 40 20 10 70100 20  0 30
  0 50 60 60100 50 40 80 60 80100 50100 60 10 20 60 40 60 70 40 80 30 90100
 10 30  0 90  0100 30 30 70 50 10 80 80 80 80100 80 20  0  0 70 30 60100 20
 90 90 40 10 30 30100 60  0  0 20 60 80  0 40 60 70 60 60 30 30100 20 30 70
 10 70 70 60 70 20 50 10 30 90 90 70 60 40 80 10 10 50 30 60 40 80 90 80 60
 50 20 70 20 60 20 70 50 10 60 70 60 30 60 60 90100 20 30 70 40 40 80 10 20
 40 20 60 50 70 50 70 50 60 30  0 80 50100 70 40 50100 70 10 60 90 30 20100
 40 10  0  0 90100 80 30 60 10 40 60 80 60 90 90 90 90 20 50 90 10 40 40 40

  0 50  0100 40 30 90 70 70100 30 80 10 90 90 10  0  0 90 90  0 50100 50
 90 30 40100 50100 20  0 60 40 40 20 70 90 10100 80 60 20 70 40 20 70 60
 60100  0100 30 90 30 60 20 70  0 60 90 40 50 60 50 10100 40  0100 30 70
 50 70 10 10 20 80 30 40 80 40 10  0  0  0 40  0 90 70 50 30 20100 50 80
 40  0 10 40100 50 50 30  0 10100 50 10 90 10 20 60 40 70 50100 60 70100
 40 20 20 30 80 90 90 90 40 50 80 70 50 30 70 60 50 70 60 70 10  0100  0
 30 10 30 10 70  0 20 80 70100 50 90 80 40 90 80 30 50 40 60 20 20 10 50
 30  0 40  0 30 40 90 20 50 90 80 80 30 50100 40 90 40100  0 50 10 10 90
100 60 50 30  0 20 10 60 20 60 90 90 50 70 60 20 50 50100 10 20 70 80  0
 30 70 30 90 80 80 90 30 90 10 60  0 50 60100 20 60 70100 80  0 20 70 10
 90 80100 10 80 30 60 50 40 80 60 20 10 70 60 50 90 10 70 60 80  0 80  0
 90 60 60 20 20 70100100 80 30 90 60  0 20100 30 50 30 60 60 20 40100100
 80 40 90 60100 90 80 20 80 80 60 90 20 60 40 90100100 50100 60 90 80 70
100 50100 30 60 30 60100 30 90 60 50  0100 80 60 10 80 10 30100 10 70 30
 50 40 50100100 70 50 40 40 50 80 70 40 10 20 40 70 80 60 40 90 50 20 30
 20 30 90 30 60  0 50 40  0 30100 40 70 50 70 60  0 10100100 20 90 90 60
 20  0 70 70 50 40 60 40 40 30 40 10100 40 40 90 30 50  0 40 10 80 90 90
 80 60100 70 60  0 90 60 40 10 20 50 40 50 70 60100 70 80 90100 10 40100
 20 90 50  0 90 10 50 20 50 10 80 40  0 50 40 70 80 40 70100 30100100 30
  0 60  0  0  0 40 20 20 60 70 60 50 50 50 10 20 40100 40 70 40 60 60  0
 40 10 50 40 70 60 90 80 80 80 70 70 50 60 90 80 80 10 50  0 80  0 50 40
 20 10 10 80 30 60 30100 60 20 70 20100 90 90 90 20 10 80 30 80 80 10 90
 90 90 70 30 60100 60 60100 60 10 50 70 10 80 20 40 30 10 30 30 40 60 70
 70 30100100 10  0 20 40 30 40 60 40 10 50 20  0100 10 90 50 80 40  0100
 70100 40 40100 70 70 70 40 50 10 80 20  0 20 20 90 80  0 60 50  0 10 70
```

Final B matrix : Size = 25x49

HORIZONTAL

C:

```
-7 -9 -6-10 -9 -9 -5 -4 -7  0 -5 -9 -6 -9 -8 -9 -2 -6-10 -5 -1 -4 -9 -1 -5
```

D:

```
 0100 80 30 60 70 10 20 50 40 10 30 40 10  0 40 20 30 30 30 30 40 30 80 40

90 10 50 30 20  0 10 30  0 30 80 20 70 30 60  0 40  0 80  0  0 20 90 10
```

Final C matrix : Size = 1x25

Final D matrix : Size = 1x49

DIAGONAL

```
 0 -5 -2 -6 -1 -3 -2 -4 -5 -3 -3 -5 [illegible]-10 -5 -5 -5 -6-10-10 -8  0 -4 -2 -3
-9  0 -1 -2 -5  0 -1 -3 -1 -8 -1 -5 -5 -6 -5 -7 -9 -6 -6 -1 -6 -1 -5  0 -4
-2 -8  0 -5 -2  0-10 -1 -4 -5 -7 -2 -8 -5 -1 -6 -9 -4 -8  0 -9 -2 -3 -4 -6
-2 -1-10  0 -3 -3 -8  0  0 -5 -8 -5 -8-10 -4 -2 -9 -2 -5 -1 -3 -2 -5 -6 -3
 0 -4 -8 -5  0  0 -3 -7 -2 -8 -1-10 -6 -2 -7 -4 -8 -1 -2 -9 -8-10 -6 -3 -8
-7 -5 -9 -7  0  0-10-10-10 -3 -6-10 -5 -9 -2  0 -6 -2 -6  0 -7  0 -6 -8 -7
-4 -4 -8 -3-10 -7  0-10 -9 -4 -2 -9 -6 -5 -1 -5  0 -2 -8 -8 -2 -4 -1 -1 -9
-5 -6 -1 -3 -2 -5  0  0 -8 -9 -5 -4-10-10 -6-10 -5 -5  0 -7-10 -5 -6 -4 -5
-5 -5 -1 -3 -1 -8 -9 -9  0 -9  0 -8 -1 -6 -6-10 -3 -1 -8  0 -5 -7 -3 -9
-2 -4 -9 -4 -3 -7  0 -5 -9  0 -9 -4 -5 -1 -8-10 -7 -1 -6 -4 -3  0 -7 -4 -4
-2 -8 -7 -3 -8 -6  0 -2 -2 -1  0 -8 -5 -4 -3 -8 -1 -6 -7 -1 -9 -9 -6-10-10
-9 -3 -5 -4 -2 -3  0 -5 -7 -6 -8  0 -3 -1 -2 -6 -4 -5 -1 -9 -2 -1  0 -7 -7
-9 -9 -1 -5 -2 -4 -3 -2 -9 -4 -5 -3  0 -5 -5 -4 -4 -9 -6 -2 -5 -7 -2 -6  0
-5  0 -5 -8-10 -9 -9 -7-10 -4 -1  0 -3  0 -8 -8 -9 -8 -9 -5 -7 -2 -7 -4 -6
-6 -6 -1 -8 -7  0 -2 -8 -6 -5 -4-10 -5 -5  0-10 -6 -2 -8 -7 -2  0 -1-10 -1
-1 -3 -9 -7 -7 -6 -8  0 -3  0 -9-10 -9  0  0  0 -3 -2 -3-10 -5 -6  0 -5 -2
-1 -3 -3 -3 -1 -4 -7 -6 -8 -3  0 -5-10-10 -4 -1  0 -2 -5 -1 -3 -6 -4 -1 -5
-1 -6 -2 -8 -8 -3 -4 -8 -3 -2 -3-10 -1 -3  0 -5 -1  0  0 -8 -3 -9 -7  0  0
-8  0 -8 -3 -6 -4 -5 -7 -8 -8 -6 -4 -6 -5 -1 -6 -3 -9  0 -5 -1 -1  0 -9 -4
-3 -5 -6  0 -9 -7 -7 -4 -7 -5 -3 -6 -4 -8 -3 -6 -6  0 -8  0 -4 -7 -9 -1-10
-7 -8 -8 -5-10 -4 -9  0 -4 -7  0 -5 -4 -6 -2 -8 -2-10 -1  0 -7 -6 -9 -1
 0  0 -4 -2 -7-10 -2 -3  0 -9  0 -1-10  0 -1 -7 -6  0 -3 -4  0  0 -1 -3 -2
-2  0 -1 -9 -6  0 -2  0 -4 -1 -9 -5 -3 -6 -8 -6 -4 -1 -8 -1 -5  0  0 -9-10
-1 -5 -4-10 -9 -1 -7 -2-10 -3 -8 -5  0 -2 -7  0  0 -3 -5 -3 -1 -9 -3  0 -7
-5 -7 -7 -5-10 -4-10-10 -8 -2  0 -2 -3 -2 -2 -7 -7  0 -4 -4 -2 -6 -7 -9  0
```

Final A matrix Size = 25x25

DIAGONAL

```
100100 50 2u100 50 20 10100 40 60 30 90 60 10 50 80 90100 30 20 50 80 60 10
 10 80 40 60 20 20 40 40 30 20 70 60 20 60 90 50 20  0 90 10100 80 80 60 80
 30 90 80 50  0 80 80  0 70 40 10 40 40 40 30 40 30 40 20 20 30100100 80 10
 70 40 40 30  0 30 90 30 20 60  0 90 20  0 40 10 40 60 10 80 90 50 30 20 20
 10 40100 60  0100 70 10 30 70100 80100 60 50 10 70 50 90 20 30 40 70 40 60
 40 90100 90 90 60 30 70 60 80 40 30  0100 90 10  0 20 90 30 70 40 20 30 10
 10 90 50 90 10 40 40 60 30 30 40100 80 10100 80 90  0 30 20100 10 40100 90
100 70100 50 90 20 20 10 30 80 30 40 10 70 80 80 20  0 80100 60 70 50100  0
 80100 30 50100 90 40 70 90100 30 10 30 40100 90 80 40 60 20100 20100 90 40
100100 40  0  0 30100 10 60 20 50 70100100100  0 90 30100 70 10 70 60100 50
 70 10 70 30 40 50 10 40 20100 60 40 30 30100 10 90 40 50 70 50 90100 40 10
 50 70 40 70100 50 10100 80 20 50  0 70 50 50 80 10100 60 60 10 50 70100 80
 80  0 40 30 30 50 70 60 40100 70 20  0100 10 20 20 30 30 50 70 40 10100100
  0 40  0 80 80 90  0  0 70100 80 50 30 70 90 60 50 30 30100 30 50100 50 60
100 40100  0 40 50 10  0100 60 80100 40 90 40 40 70 80 10 40 40 30 70 20  0
 50 30100 80100 40 60 20 40 30 10  0 30 70 60  0100  0 10 60 50100100 30 20
 40  0 10 70 30 80100 60  0 40 80 20 50 20  0 30 90 60 30 10 50 70 50 70  0
  0100 70 60 60 10  0100 60 20100 90  0 90 60 50 60 90 50 40 60  0 70 50 90
 40 70 90 80 20  0 60 70 20 20 40 70 50100 50 90 30 40100100 90 50 80100 10
 70 50 60 90 20100 30 80 70 30 50  0 90 60 10 10 40 30 40 10 70 30 30 80 30
  0 40 70100 60100 30 90 40 90 20 60 60 60 20 30 30 50 70 80 20 70  0 50 20
 40 20 30 30 60  0 70 90  0 60 90 70 40  0 20 50 80 80 30 50 90100 70 70100
 90  0 20 30 40 20 40 60 20 90 20 70 60 70 30 10 50 60 70  0100 40 20 40 10
 50  0 80 20 50 50 50 40 60 40 50 90 30 60 90 20  0 40 10 50  0 80 30 50 10
 40 50  0100 40 50 20 10 60 80 30 50 20 90 50 80 80 80 20 30 60 30100 30 30
 90 30  0 10100 10 80 20 10 70 60 50 40  0 50 40 20100 10 90 60  0 10 10
 10 70 70100 90 10 60 40 80 70 60 70100 10 20 50 50  0 90 40 20 70 60 60
 40 50 30 30 40 40 10 90 90 40 40 70 10 80 20 10 60 50 70  0 20 30100  0
 80  0 90  0100 90100 90100 80 70 20 50100 40 20 10 90100 30 10  0 70 10
 60100 70 70 50100 70 40 30 80 70 10 50 10 50 80 90 70 90 60 90 40 30 10
 10  0 80 60 60 40100 40 20 10 40 30 90 60 20 60 10 30100 20 80100100  0
 10 20 20 80 60 10 40 70 90100 80 20 10 50 70  0 90 70 10 50 60 30 20 90
 90 40100 70 10 20 90 60 80 30  0 80  0100 20100 20  0 80100 10 10 40 60
 50 80 80 30 50 50 60 40100  0 70  0 80100 50 70 80 20 10 90100 40 40 30
 80100 70 20  0 70 10 80100 60  0 70 20 90 20 70 20 90 80 40  0 50 80 50
 60 90 50 70 70100 80 20 40 70 30  0 30 40 20 60100 70 60  0100 30 70 20
100 90 30 40 50100 60 70  0 40 20 20 50 30 70 40 90 90100 60 10  0 10 10
 30 40 20 40 40  0 70 30 10 20 90 50 80 80 80 10 70  0  0 10 90 90 80 80
 50  0 80 80  0 60 20 90 80 10 70 50 80 90 50 60 10 10 50 80100 10 80 80
 60 30 40 30 70  0  0100  0 70 90 70100 60100100 30 40 10 20 50 70 80 90
 10 90 90 50 90 20 60 40100 80100 60 60 10 50 70100 60 10 80 40 40 60 20
 50 80 20100 20100 70 10 70 80 90 40  0 30 50 10 60100 50  0 50  0 50 50
 40 10 50 70 10 70 40 50 70100  0 60 90 30 90 70 40 80 30 50  0 40 80 40
 50 10100  0 70 50 10 40 10 60 50 60 60 20 30 30 50 80 80 10  0100 40 40
 60 60 30 60 20 40 20 10 30 20 60  0 70 50 40 90 40 30 90 80 70 10100 90
 80  0  0 10100 60 40 20 20 10 50 80 20 90 50 50  0 80 70 60 60100  0 40
  0100 50 30 90 40 60  0 80 50 20 70 80 50 90 10 60 40100 90 10 20 40 80
 20 90 90 50 90 10 50 40100 90 90 90 90 50 10 70 30  0 80 60 20 10 70 50
 50 70 50 90 20 40100 90 50  0 20 60 70 70 30 50 20 80 80 20 30 10  0 10
100  0 60 30100 50 10  0 40  0 40 90100 90  0 70100 10 70100  0 90 10 80
```

Final B matrix Size = 25x49

DIAGONAL

C:

```
-2 -8 -3 -8 -6 -2 -4 -1 -2 -2 -1-10 -9 -5 -8 -1 -9 -6  0 -7 -9 -6 -8 -9 -2
```

D:

```
50 70  0  0 70  0 60  0 10 80  0 70 30 90  0 40  0 10100 20 50  0 50  0  0

10 10 60 80 70 80 40 30 80 20 80 60 40 40 70 30 50 50 90  0 40 90 80 10
```

Final C matrix Size = 1x25

Final D matrix Size = 1x49

APPENDIX B

COEFFICIENTS FOR V2

```
    3 08A
 0 -1 -1  0 -5  0 -9 -6-10  0 -8 -7 -4 -4 -4 -3 -9 -7-10  0 -5 -2 -3 -7 -4
-6  0 -2 -7 -1 -2 -3 -9 -3 -3 -6 -5 -7 -6 -6 -5 -6 -9  0  0 -2 -5 -6  0  0
-3  0  0  0 -2-10 -9 -1 -4 -8-10 -3 -1 -8  0 -2 -8 -7 -7  0 -5 -1 -9 -5  0
-9 -2  0  0 -9  0 -9 -7 -1 -5 -8 -1 -4  0 -9 -1 -6 -8-10 -1 -7 -6 -8 -1  0
-1 -9 -3 -4  0 -4 -1-10 -4 -3 -1 -3 -6 -3 -6 -7 -8 -1 -7 -5 -5 -2  0 -9 -7
 0 -8 -5 -6  0  0 -1 -3  0 -5 -8 -4 -2-10 -3 -2 -1 -1 -6 -1 -2 -3-10 -8 -6
-9 -5 -1 -6 -4 -5  0 -8 -3 -9-10 -2 -5 -9 -8 -6 -1-10 -8 -4 -3 -5 -2 -2 -6
-7 -1 -1 -2 -4 -5 -3  0 -4-10 -1 -3 -2 -3-10 -8 -1 -7 -3 -4-10 -4 -6 -7 -1
-1 -5-10 -6 -3 -4 -1 -1  0 -5 -1 -9 -8 -7 -9 -2 -9 -3 -1 -7 -9 -2 -3  0 -9
-8 -4 -7 -5 -6-10 -5-10 -3  0 -2 -2 -1 -2 -3 -7 -6 -2  0 -9 -1 -1 -7 -1 -3
 0 -9 -4 -4 -3 -5-10 -1 -7 -5  0 -8 -3 -4  0 -7 -5 -9 -2 -7 -5  0 -6 -7 -4
10 -8 -4 -2 -3 -4-10 -5 -7 -8 -7  0 -5 -3 -6 -9 -5 -1 -1 -3 -2 -4 -3 -8 -7
-5 -6  0 -5 -1 -9 -8 -8 -7 -7 -8  0  0-10 -6 -3 -8 -6 -1 -6 -1 -9 -8 -9 -7
```

```
¯2 ¯3 ¯4 ¯9 ¯7 ¯3  0  0  0 ¯8 ¯7¯10 ¯9  0 ¯6 ¯4 ¯4 ¯1 ¯9 ¯8 ¯2 ¯3  0 ¯8 ¯4
¯4 ¯2 ¯3 ¯3 ¯9 ¯9 ¯9 ¯1 ¯5 ¯2 ¯4 ¯4 ¯2 ¯5  0 ¯5¯10 ¯9 ¯4¯10  0 ¯8 ¯1 ¯9 ¯4
¯6 ¯6 ¯2 ¯3 ¯6 ¯7 ¯7 ¯7¯10 ¯4  0 ¯4 ¯5 ¯7¯10  0 ¯8 ¯4¯10 ¯3 ¯6 ¯4 ¯8 ¯6  0
¯2 ¯1  0 ¯4 ¯5 ¯6¯10 ¯5 ¯7 ¯6 ¯6 ¯3 ¯8  0 ¯3 ¯2  0¯10 ¯7 ¯2 ¯3 ¯1 ¯4 ¯1¯10
10 ¯5 ¯4 ¯4 ¯1 ¯3  0 ¯9 ¯1¯10 ¯5 ¯9 ¯1 ¯7 ¯3 ¯9 ¯3  0  0 ¯3 ¯1  0 ¯4 ¯1¯10
¯9 ¯7 ¯6 ¯5 ¯7 ¯6 ¯1¯10 ¯8¯10 ¯7 ¯6 ¯2 ¯9¯10 ¯7 ¯6 ¯2  0 ¯5 ¯2 ¯4 ¯8 ¯3 ¯3
¯10 ¯1 ¯4 ¯7¯10  0 ¯6 ¯6 ¯6 ¯7¯10 ¯7 ¯8 ¯8 ¯8 ¯8 ¯2¯10 ¯2  0 ¯1 ¯7 ¯7 ¯3 ¯1
¯8 ¯3 ¯7  0 ¯6 ¯9 ¯6 ¯7 ¯5 ¯7 ¯4 ¯4 ¯3 ¯3¯10 ¯8 ¯3 ¯5 ¯1 ¯6  0 ¯8 ¯3 ¯7 ¯3
¯8 ¯5 ¯7 ¯7 ¯1 ¯8¯10¯10 ¯3 ¯4 ¯2 ¯3 ¯1 ¯6 ¯8 ¯9 ¯4¯10 ¯2 ¯4 ¯7  0 ¯3 ¯7¯10
¯4 ¯5 ¯9 ¯5 ¯2 ¯2 ¯6 ¯8 ¯1 ¯9 ¯6 ¯1 ¯2 ¯7 ¯4 ¯1 ¯4 ¯7 ¯8 ¯8 ¯7 ¯7  0¯10 ¯9 ...
¯10 ¯1 ¯9 ¯8 ¯1 ¯6  0¯10 ¯2 ¯2  0 ¯5 ¯2¯10 ¯2 ¯4 ¯8 ¯6 ¯7 ¯4 ¯6  0 ¯8  0 ¯2
¯7 ¯3 ¯5 ¯4 ¯8 ¯4¯10 ¯3 ¯8 ¯9 ¯8 ¯9 ¯7 ¯8 ¯2 ¯3 ¯9 ¯8 ¯1 ¯7 ¯9 ¯2  0 ¯9  0
      3 0#B
 0100 30  0 60 80 90 30 40 40 30 80 60 10 10 30 80  0  0 60 30
100100100 10 10 60 80 90 40 70 70 90 20 90 90 90 80 30 90  0 10
 0 20 20 60 10 70 60 90100 50 60 90 80 40 60 70  0 40 80 70 30
90 90 20 70100 50 70 20 70 20 30 80 70 20 40 60 70 40100 30 30
50  0 60 80 20 70 50 80100 10 60 10 70 90 80 40 60 60 60 90 20
40 20 40 90 10  0 50  0 50 10 40100 50 50 20 80  0 80 30 30 40
10 80 80 20 10 70 60 40 60 20  0 30 40 10 40  0100 90 70 70 80
30 70 40 70 70 30 80 20 30  0 30 30 10 10 70 80 80 20  0 60 80
40  0 80 60 30 60 20 10 70 10 90 50 20 20 30 90100 60 40 40 80
80 80 10 20 90  0  0 90100 90 50 80 60 60 40 20  0100100100100
20 40 50  0 50 30 70  0100 40 90 60 50 40 50  0 10 70100100 80
30 50 40  0 20100 80 30 30 90 50 30 90  0100 40 30 30  0 80 30
 0 80 10 60 10  0100 80 10 60 30  0 20 80 50 40100 10 10 70 10
60  0 60 20 30 90 80 80 20 10  0  0 80  0  0100  0 60 30 60 40
50 80 80 30 60 50100 30 70 30 40 80 40 20 10 60 80 50 10  0 90
40 60 80 10 60 90 40 40 50 20 10100  0 50 40 70 70 40 70 80 30
100 90 30 90 90100 30 80 50100 50 10 70 70 70 30 60 80 70  0 60
80 20100 80  0 40 20 80 90 50 50 40 10 80 80 10 10  0100 70 60
10 20  0 70  0100 50  0 40100  0 80 80 60 50 20 10 10 20 50 20
20100 20 50 80 80 90 10 40 40 20 70 50 50  0 80 90 50 30 40 90
10 30 60 20 90100 60 90 30 60 50 20 80100 90 10 80 70 80 50 80
10 30 80 50 10 50100 20 20 60 10 70 40 30 20 80 70 80100 80 10
50 30 90 80100 80 80 60 20 80 70 90 20 80 60 90 20 40  0 80 10
30 20 10 10  0100 40 70 70 10 10 10 80 40  0 90 70100  0  0 80
 0 80100 30 70 60 50  0100100 40 40 10 50 40 90  0 90 80 30 10
      3 0#C
¯7 ¯1¯10 ¯5 ¯4 ¯2 ¯7¯10¯10 ¯9 ¯1 ¯8 ¯5 ¯3 ¯9 ¯2 ¯3 ¯9  0 ¯9 ¯2 ¯7 ¯6 ¯5 ¯1
      3 0#D
20 60 30 60 10 70 20  0 30 40 20 10 30 40  0 20 30 90100 80 60
```

A25x25

B25x21

C1x25

D1x21

INPUT = 7x28

OUTPUT = 1x1

APPENDIX C

```
CFLAGS              = -g

OBJS                = image_util.o vfilter.o median.o IRP_histogram.o \
                      IRP_edge_detector.o IRP_visar2.o IRP_LGN.o ART2.o verrtool.o
ALL_OBJS            = $(OBJS)

LIBS                = -lm -lsuntool -lsunwindow -lpixrect -lstd
ALL_LIBS            = $(LIBS)

cellview:           cellview.o $(ALL_OBJS)
        cc -o cellview cellview.o $(ALL_OBJS) $(ALL_LIBS)

cellview.o:               cellview.c            cellview.h       netparam.h \
                          activation.h          image_io.h       LTM.h
image_util.o:             image_util.c          image_io.h
verrtool.o:               verrtool.c            cellview.h
vfilter.o:                vfilter.c             cellview.h       netparam.h \
                          image_io.h            activation.h
median.o:                 median.c
IRP_histogram.o:          IRP_histogram.c       cellview.h       image_io.h
IRP_edge_detector.o:      IRP_edge_detector.c   cellview.h       netparam.h \
                          activation.h          image_io.h
IRP_visar2.o:             IRP_visar2.c          cellview.h       netparam.h \
                          activation.h
IRP_LGN.o:                IRP_LGN.c             image_io.h       activation.h
ART2.o:                   ART2.c                activation.h     LTM.h
```

```
        /* cellview.h          Printed on 18-December-1989 */
/*
        Header File for RL Harvey's IRP Software Testbed
        Adapted from viewtool.h with additional coding by
                Paul Dicaprio and KG Heinemann
```

```
*/
                        /* Defines */

/* Parameters for plot of image histogram */
#define HST_HEIGHT              64  /* Plot amplitude for largest peak */
#define PLOT_BORDER_WIDTH       16  /* Width of blank border around plot */
#define HST_WIN_WIDTH           (VLT_SIZE   + (2 * PLOT_BORDER_WIDTH))
#define HST_PLOT_HEIGHT         (HST_HEIGHT + (2 * PLOT_BORDER_WIDTH))
#define N_HST_DISPLAY_PIXELS    HST_WIN_WIDTH * HST_PLOT_HEIGHT
#define HST_WIN_HEIGHT          120

/* Parameters for plot of edge detector spectrum */
#define EDF_SPECTRUM_SIZE       2500    /* Value for cytology discrimination */
/* #define EDF_SPECTRUM_SIZE    144     Value for ATR application */

#define EDF_DISPLAY_WIDTH       (2 * VLT_SIZE)
#define EDF_WIN_WIDTH           (EDF_DISPLAY_WIDTH + (2 * PLOT_BORDER_WIDTH))

#if (EDF_SPECTRUM_SIZE < EDF_DISPLAY_WIDTH)
#define EDF_PLOT_WIDTH          EDF_WIN_WIDTH
#else
#define EDF_PLOT_WIDTH          (EDF_SPECTRUM_SIZE + (2 * PLOT_BORDER_WIDTH))
#endif

#define N_EDF_PLOT_PIXELS       (EDF_PLOT_WIDTH * HST_PLOT_HEIGHT)

/* Number of signals generated by the offset detection module (V2) */
#define V2_SPECTRUM_SIZE        4

/* First location for offset (V2) signals in the spectrum array */
#define V2_SPECTRUM_OFFSET      1

/* First location fo edge detector (V1) signals in the spectrum array */
#define EDF_SPECTRUM_OFFSET     (V2_SPECTRUM_OFFSET + V2_SPECTRUM_SIZE)

/* Total number of input signals for ART2 in the classification channel */
#define TOT_SPECTRUM_SIZE       (EDF_SPECTRUM_OFFSET + EDF_SPECTRUM_SIZE)

                        /* -- SunView -- */

extern  Frame           message_frame;
extern  Canvas          hst_canvas, edf_canvas;
extern  Panel           message_panel, img_proc_panel;
extern  Panel_item      msg_item, out_item;
extern  Pixwin          *hst_pw, *edf_pw, *edf_hdr_pw;

        /* -- External procedures -- */

extern  void    slider_proc();
extern  void    roll_vlt_proc();
extern  void    mean_filter_proc();
extern  void    median_filter_proc();
extern  void    binary_filter_proc();
extern  void    set_binary_filter_proc();
extern  void    reset_mess_proc();
extern  void    batch_cwd_proc();
extern  void    batch_fil_proc();
extern  void    LGN_mult_proc();
extern  void    V2_mult_proc();
extern  void    old_LTM_proc();
extern  void    new_LTM_proc();
extern  void    read_LTM();
extern  void    write_LTM();

        /* -- More external routines -- */

extern  int     read_test();
extern  void    make_IRP_histogram();
extern  void    hst_equalize();
extern  void    spiral_map();
extern  void    detect_edges();
extern  void    display_edf_results();
extern  void    detect_offset();
extern  void    ITC1();
extern  int     IRP_auto_proc();
extern  void    IRP_batch_proc();
```

```
        /* External variables */

        /* Width and height of histogram display image */
extern  int     hist_width, hist_height;

        /* Width of display window for the edge detector spectrum */
extern int      edf_width;

extern  int     IRP_hist_data[]; /* Image histogram array */
extern  int     hstmax;          /* Maximum count in histogram */
extern  int     hmax_loc;        /* Intensity val corresponding to max count */

        /* Flag to Indicate Whether Histogram Array Contains
             Results that are Valid for the Current Image    */
extern u_char validhst_flag;

        /* Flag to Indicate Whether Edge Detector Spectrum
             (V1) Values are Valid for the Current Image    */
extern u_char valid_V1_flag;

        /* Flag to Indicate Whether Centering Signal (V2)
              Values are Valid for the Current Image        */
extern u_char valid_V2_flag;

    /* Flag to indicate whether the program is operating in a batch mode */
extern u_char batch_flg;

/* Parameter blocks for manipulation of "STD" files */
extern  int     std_ioblk[32], std_pblk[32];

extern  u_char  *hst_image;
extern  u_char  *edf_image;

extern  int     binary_thresh;

extern  FILE    *fp_vlt,        *fp_img,        *fp_out;
extern  int     vlt_format,     img_format,     out_format;
   /* Use information in SunView include files to define
      a structure for accessing the base frame's color map */
extern struct colormapseg bas_cms;

   /* String to hold name of base frame color map segment */
extern char bas_cmsname[CMS_NAMESIZE];

/* Current Working Directory and File Name for Batch Sequence Information */
extern char seq_cwd[], seq_fname[];

/* Structure to hold sequence control information for batch operations */
extern struct sequence *batch_seq;

/* Structure to hold pointers for ART 2 result information */
extern struct ART2_res_ptrs log_class_info;
        /* image_io.h            Printed on 18-December-1989 */

/* Global variables for display and manipulation of images in programs
   developed for Bob Harvey's IRP by KG Heinemann and and P.N. DiCaprio */

#define FNL             49      /* No. of characters allowed in file name */
#define VLT_SIZE        256     /* Total number of color map entries */

/* Number of color map entries to use for BW display of input image */
#define IMG_VLT_SIZE    128

/* Height of color bar display for Video Look-up Table */
#define VLT_HEIGHT      10

     /* Horizontal and vertical dimensions of canvas for image display */
                        /* Size of SUN Monitor Screen */
#define IMG_CANVAS_X_SIZE       1184
#define IMG_CANVAS_Y_SIZE        900

                        /*  Define Image Parameters  */
#define IMAGE_HEIGHT             512
#define IMAGE_WIDTH              512
```

```
        /* Code to indicate successful "std" file I/O */
#define IMG_FILE_OK                 1

/* Code to indicate error in reading data from a file */
#define DATA_RD_ERROR               -1

/* Code to indicate attempt to read from a file that has not been opened */
#define FIL_NOT_OPN_ERR            -10

/* Code to indicate that requested "std" pattern number is out of range */
#define BAD_STD_PAT_NUM            -15

extern  u_char  red[], green[], blue[];
extern  u_char  *image;

extern  char    cwd[];
extern  char    img_fname[];

/* ASCII representation of pattern index number within the image input file */
extern  char    imgnum_str[];

extern  char    vlt_fname[];

extern  char    header[];

/* Pointer to error message string generated by image I/O routines */
extern  char    *err_str;

/* Number of rows already specified in a given panel */
extern  int     npnl_rows;

/* Command parameters for "std" file I/O */
extern  int     std_ioblk[];

extern  int     ok_img_file;
extern  int     box_flg;                /* flag for defined image box */
extern  int     size_x, size_y;         /* input image width and height */
extern  int     zoom_x, zoom_y;         /* zoom magnification factors */

/* Horizontal and Vertical Offsets of Displayed Image within Image Canvas */
extern  int     img_x_offs, img_y_offs;

/* Thickness of a Default Scroll Bar for Proper Sizing of the Image Canvas */
extern  int     scroll_bar_thickness;

extern  FILE    *fp_vlt;
struct  BOX_STRUCT {int size_x, size_y, x0, y0, x1, y1, x, y;};

                    /* -- Objects for SunView -- */

extern  Frame       base_frame;
extern  Panel       control_panel;
extern  Panel_item  cwd_item, file_item, num_item, hdr_item, vlt_item;
extern  Panel_item  csr_item, zoom_item, img_box_item;
extern  Canvas      img_canvas, vlt_canvas;
extern  Menu        img_menu;
extern  Cursor      img_cursor;
extern  Pixwin      *bas_pw, *img_pw, *vlt_pw;
extern  struct      BOX_STRUCT img_box;

                    /* -- External procedures -- */

extern  void    cwd_proc();
extern  void    img_open_proc();
extern  void    std_pnum_proc();
extern  void    vlt_open_proc();
extern  int     display_proc();
extern  void    clear_canvas_proc();
extern  void    zoom_proc();
extern  void    unzoom_proc();
extern  void    quit_proc();
extern  void    xy_proc();
        /* netparam.h           Printed on 18-December-1989 */

/*---------------------------------------------------------------------------
          Header File for Neural Net Feature Extraction Algorithms
                 in RL Harvey's IRP Software Testbed
```

```
                      Created by KG Heinemann on 31-July-1989
-----------------------------------------------------------------------*/

/* Number of pixels spanned by one dimension of square input window */
#define INPUT_WINDOW_SIZE      7

#define N_HIDDEN_NEURONS      25      /* No. of units in hidden layer */
#define N_OUTPUTS              1      /* No. of edge detector outputs */

/* Calculate proper number of locations needed for temporary storage
   of direct contributions to activation from input signals */

#if (N_HIDDEN_NEURONS > N_OUTPUTS)
#define MAX_NEURONS N_HIDDEN_NEURONS
#else
#define MAX_NEURONS N_OUTPUTS
#endif

/* Specify "C" data type for representation of activation levels
           in neural network edge detection algorithm */
#include "activation.h"

/*----------------------------------------------------------------------*/

/* Define macro to perform multiplication of vectors by a matrix */

int irow,      /* Index for  rows   of matrix and output vector elements */
    icol;      /* Index for columns of matrix and input  vector elements */

int matrix_element_ptr; /* Index for accessing individual matrix elements */

/* Pointer for accessing specific elements of the output vector */
ACTIVATION_DATA_TYPE *output_vector_ptr;

             /* Vector-matrix product in direct orientation */
#define matrix_vector_product(nc, nr, matrix, input_vector, output_vector) \
  matrix_element_ptr=0; \
  for (irow=0; irow<nr; ++irow) \
    { \
      *(output_vector_ptr=output_vector+irow) = 0; \
      for(icol=0; icol<nc; ++icol) \
        *output_vector_ptr+= \
           *(input_vector+icol) * \
             (ACTIVATION_DATA_TYPE)*(matrix + matrix_element_ptr++); \
    }

/*----------------------------------------------------------------------*/

  /* Define procedure to compute activation of the hidden units as a macro */

        /* Sum of differences between subsequent activation levels */
ACTIVATION_DATA_TYPE act_delta;

  /* Iteration Counter for Procedure to Compute Hidden Unit Activations */
int iter_count;

int input_index;

#define compute_hidden_unit_activations(num_inp, num_hid, A_matrix, B_matrix) \
\
        /* compute direct contributions to hidden layer activations \
           from input signals and store them in designated array */ \
\
  matrix_vector_product \
    (num_inp, num_hid, B_matrix, input_neuron_signal, B_or_D_fi) \
\
    /* store these direct contributions as neuron activation levels \
         for first step of the iterative calculation procedure */ \
  for(input_index=0; input_index<num_hid; input_index++)     \
    hidden_neuron_signal[input_index] = B_or_D_fi[input_index];     \
\
  iter_count = 0;         /* Initialize iteration counter */           \
\
/* Initialize difference measure so as to guarantee at least one iteration */ \
  act_delta = pow(2.0, 32); \
\
```

```
/* Iterative calculation of activation levels for hidden units */     \
while (act_delta > 0 && iter_count < 10)                               \
  {                                                                    \
    for (input_index=0; input_index<num_hid; input_index++)  \
      {                                                                \
\
           /* Save current neuron activations for comparison           \
                    with results of next iteration            */       \
        previous_activation[input_index] =                             \
          hidden_neuron_signal[input_index];                           \
\
    /* Pass previous activation levels through the sigmoid rectification */ \
        sigrect[input_index]=step_sigmoid(previous_activation[input_index]);\
      }                                                                   \
\
/* Mediate interactions among hidden units by matrix-vector multiplication */\
    matrix_vector_product \
      (num_hid, num_hid, A_matrix, sigrect, hidden_neuron_signal)    \
\
    act_delta = 0.0;          /* Initialize the Difference Measure */ \
\
    for (input_index=0; input_index<num_hid; input_index++)  \
      {                                                               \
         /* Add in Direct Contributions from the Input Signals */     \
        hidden_neuron_signal[input_index] += B_or_D_fi[input_index];  \
\
    /* Compute Difference Measure and then Store New Activation Levels*/ \
        act_delta += fabs (hidden_neuron_signal [input_index] -          \
                           previous_activation  [input_index]);          \
      }                                                                  \
\
    ++iter_count;             /* Increment interation counter */         \
  }                                                                      \
/*--------------------------------------------------------------------*/

/* Sigmoid functions to convert neuron activations into transmitted signals */

#define step_sigmoid(X) ((X)>0 ? 1.0 : 0)
#define ramp_sigmoid(X) ((X)>0 ?  X  : 0)

/* Error code to indicate problems during V2 offset calculations */
#define V2_CALC_ERR 2

               /* --- Define Externals --- */

/* Array to Store Collected Edge Detector Results from Multiple Windows */
extern ACTIVATION_DATA_TYPE frwd_feature[];

/* Index to Indicate Next Unused Location in the "Edge Feature" Array
               and Cumulative Entry Counter for that Array */
extern int ftr_counter;

/* Pointer to memory region for compressed image in V2 module */
extern ACTIVATION_DATA_TYPE *V2_hidden_layer;

/* Strings for error messages in routines to read matrix coefficients */
extern char *A_str, *B_str, *C_str, *D_str;

/* Rectified signals transmitted by the input neurons */
extern ACTIVATION_DATA_TYPE input_neuron_signal[];

/* Activation levels for the hidden neurons */
extern ACTIVATION DATA_TYPE hidden_neuron_signal[];

/* Activation levels for the output neurons */
extern ACTIVATION_DATA_TYPE output_neuron_signal[];

/* Array to store component of neuron activation caused by input stimulus */
extern ACTIVATION_DATA_TYPE B_or_D_fi[];

/* Array to store previous activation levels for iterative computation */
extern ACTIVATION_DATA_TYPE previous_activation[];

/* Array to store rectified input signals */
extern ACTIVATION_DATA_TYPE sigrect[];
```

```
/* Number of image pixels to skip when moving from the end of one row
        in an input window to the beginning of the next one          */
extern int row_skip_increment;

/* Weighting factor for the LGN Sum signal in input to the ART 2 classifier */
extern float LGN_wt;

/* Weighting factor for the V2 Signals in input to the ART 2 classifier */
extern float V2_wt;
        /* activation.h         Printed on 18-December-1989 */

#define ACTIVATION_DATA_TYPE float
        /* LTM.h                Printed on 18-December-1989 */

        /* Header file to make Long Term Memory trace information
             available to programs outside the "ART2.c" file     */

/* Number of output categories (F2 nodes) for the ART2 classifier */
extern  int     nF2;

                /* Number of output category (F2) nodes
        which have been associated with particular input patterns */
extern  int     Nactv;

extern  float   **z;    /* Pointers to actual LTM values */

/* Structure for returning pointers to ART 2 result information */
struct  ART2_res_ptrs
{
  int   cat_node;
  int   num_pass;
  float R_value;
};
        /* cellview.c           Printed on 18-December-1989 */
/*
  Tool for viewing  512 X 512 test images for IRP
  Uses SUN-View system
  NOTE: this is just a cheap knockoff of JT's viewtool so I can just get
  the job done.  Better things are comming.

  Added test code to put boxes around sections of images. -- this will be
  useful when we have some fancy applications to run later.

  14-Feb-1989 KGH added code to compute and display image histogram

        05-06 October 1989 KGH added code to implement panel I/O
          for information pertaining to the ART 2 classifier.
*/

#define NUM_STR_LEN 11

                        /* -- Includes -- */

#include        <stdio.h>
#include        <math.h>
#include        <suntool/sunview.h>
#include        <suntool/canvas.h>
#include        <suntool/panel.h>
#include        <suntool/scrollbar.h>
#include        <local/STD.h>

#include        "image_io.h"
#include        "cellview.h"
#include        "netparam.h"
#include        "LTM.h"         /* ART 2 Long Term Memory Trace Information */

                /* -- External variables -- */

int     hist_width =HST_WIN_WIDTH,      /* histogram display image width  */
        hist_height=HST_PLOT_HEIGHT;    /* histogram display image height */

        /* Width of window for displaying edge detector spectrum */
int     edf_width=EDF_WIN_WIDTH;

u_char  *hst_image=NULL;        /* dynamically allocated hstgrm plot array */
```

```
        /* Dynamically Allocated Edge Detector Spectrum Array */
u_char  *edf_image=NULL;

/* Current Working Directory and File Name for Batch Sequence Information */
char    seq_cwd[FNL], seq_fname[FNL];

                /* Strings for ART 2 Control Panel Items */
char    LGN_mstr[10], V2_mstr[10], old_LTM_file[FNL], new_LTM_file[FNL];

                /* -- Sunview -- */

Frame           message_frame;
Canvas          hst_canvas;
Canvas          edf_canvas;
Canvas          edf_hdr_canvas;
Panel           message_panel, ART2_panel, img_proc_panel;
Panel_item      batch_cwd_item, batch_fil_item, msg_item, out_item;
Panel_item      ART2_hdr_item, LGN_mult_item, V2_mult_item,
                LTM_Input_item, LTM_output_item;
Pixwin          *hst_pw, *edf_pw, *edf_hdr_pw;
Pixfont         *dispfont;

  /* Use information in SunView include files to define
     a structure for accessing the base frame's color map */
struct colormapseg bas_cms;

  /* String to hold name of base frame color map segment */
char bas_cmsname[CMS_NAMESIZE];

/* Text Header for Histogram Display Canvas */
char *hst_header = "Image Histogram";

/* Text Header for Display of Edge Detector Results */
char *edf_header = "Edge Detector Results";

/* Horizontal and Vertical Offsets of Displayed Image within Image Canvas */
int i, img_x_offs, img_y_offs;

/* Weighting factor for the LGN Sum signal in input to the ART 2 classifier */
float LGN_wt;

/* Weighting factor for the V2 Signals in input to the ART 2 classifier */
float V2_wt;

              /* Files for storing ART 2 Long Term Memory Traces */
FILE *LTM_source_file=NULL, *LTM_output_file=NULL;

/* Structure to hold sequence control information for batch operations */
struct sequence *batch_seq=NULL;

/* Structure to hold pointers for ART 2 result information */
struct ART2_res_ptrs log_class_info;

                /* -- main(): set up the window environment -- */

main(argc,argv)
int     argc;
char    **argv;
{
  initialize   (argc, argv);
  setup_windows(argc, argv, "IRP Interactive Image Analysis Software Testbed");
  setup_img_menu();
  post_initialize();
  window_main_loop(base_frame);
  exit(0);
}

int batch_file_info()
{
  batch_cwd_item =
    panel_create_item(control_panel, PANEL_TEXT,
                      PANEL_LABEL_STRING,    "Batch Directory:",
                      PANEL_VALUE,           seq_cwd,
                      PANEL_VALUE_DISPLAY_LENGTH, FNL,
                      PANEL_NOTIFY_PROC,     batch_cwd_proc, 0);

  batch_fil_item =
```

```
    panel_create_item(control_panel, PANEL_TEXT,
                       PANEL_LABEL_STRING,  "Batch SEQ File:",
                       PANEL_VALUE,          seq_fname,
                       PANEL_VALUE_DISPLAY_LENGTH, FNL,
                       PANEL_NOTIFY_PROC,    batch_fil_proc, 0);
  return(2);
}

int aux_file_info()
{
  /* NULL ROUTINE - No other file information used in this application */

  return(0);    /* Tell calling program that no new lines have been added */
}

void aux_buttons()
{
  /* NULL ROU...E - No other control panel buttons  used in this application */
}

void aux_panels()
{
  void mk_ART2_panel();

  mk_ART2_panel();
}

aux_windows()
{
  /* Upper Y-coordinate of highest display canvas in the base frame */
  int top_y;

  /* Create canvas area for displaying the image histogram */
  hst_canvas =
    window_create(base_frame,    CANVAS,
                  WIN_RIGHT_OF,  img_canvas,
                  WIN_X,         size_x+scroll_bar_thickness+8,
                  CANVAS_WIDTH,  hist_width,
                  CANVAS_HEIGHT, HST_WIN_HEIGHT,
                  WIN_WIDTH,     hist_width,
                  WIN_HEIGHT,    HST_WIN_HEIGHT, 0);

  /* Create canvas area for displaying the spectrum of edge detector results */
  edf_canvas =
    window_create(base_frame,         CANVAS,
                  WIN_X,              size_x+scroll_bar_thickness+28,
                  WIN_WIDTH,          edf_width,
                  WIN_HEIGHT,         HST_WIN_HEIGHT,
                  0);
  window_set(edf_canvas,
             CANVAS_AUTO_SHRINK,        FALSE,
             CANVAS_WIDTH,              EDF_PLOT_WIDTH,
             CANVAS_HEIGHT,             HST_WIN_HEIGHT,
             WIN_HORIZONTAL_SCROLLBAR,  scrollbar_create(0),
             0);

  /* Create canvas area to display a text header for the edf canvas */
  edf_hdr_canvas =
    window_create(base_frame,         CANVAS,
                  WIN_X,              size_x+scroll_bar_thickness+200,

                  WIN_WIDTH,          212,
                  WIN_HEIGHT,         20,
                  0);

  /* Create control panel for selection of image processing algorithms.
     Do this step after laying out all the other canvases and computing
     final width of the enclosing frame, so that this particular panel
                  can strectch across that entire width                  */
  mk_img_proc_panel();

  /* Update those positional parameters of the display canvases which
       depend on the exact placement of the assorted control panels     */

  window_set (vlt_canvas, WIN_BELOW, img_proc_panel, 0);
  window_set (img_canvas, WIN_BELOW, vlt_canvas, 0);
```

```
  /* Set proper positions for canvases which display processing results */

  top_y = (int)window_get(img_canvas, WIN_Y);

  window_set (hst_canvas,     WIN_Y, top_y,                    0);
  window_set (edf_canvas,     WIN_Y, top_y+HST_WIN_HEIGHT+48, 0);
  window_set (edf_hdr_canvas, WIN_Y, top_y+HST_WIN_HEIGHT+23, 0);

  hst_pw     = canvas_pixwin(hst_canvas);
  edf_pw     = canvas_pixwin(edf_canvas);
  edf_hdr_pw = canvas_pixwin(edf_hdr_canvas);
}

initialize(argc,argv)
int  argc;
char **argv;
{
  u_char *reset_image_block();

  /* Store name of Current Working Directory in "cwd" */
  getcwd(cwd,FNL);

  /* ... and in the Current Working Directory for Batch Sequence Information */
  strcpy (seq_cwd, cwd);

  /* Initialize names of image file and video look-up table file */
  strcpy(img_fname,"");
  strcpy(vlt_fname,"grayscale");

  /* Initialize multipliers for the LGN Sum signal and the V2 signals
     -- and format strings for display in the ART 2 control panel      */
  LGN_wt = 0.001;
  sprintf (LGN_mstr, "%.3f", LGN_wt);
  V2_wt = 0.100;
  sprintf (V2_mstr,   "%.1f", V2_wt);

  /* Open auxiliary font for text display */
  dispfont = pf_open("/usr/lib/fonts/fixedwidthfonts/cour.b.16");
  if(dispfont==NULL)
    errmess("Initialize error opening auxiliary font file");

  /* Determine thickness of a default scroll bar */
  scroll_bar_thickness = (int) scrollbar_get(SCROLLBAR, SCROLL_THICKNESS);

  hst_image =
    reset_image_block(hst_image, hist_width, hist_height, "histogram");
  edf_image =
    reset_image_block(edf_image, EDF_PLOT_WIDTH, hist_height, "edf spectrum");
}

post_initialize()
{
  vlt_open();            /* Set up video lookup tables */

  /* Display appropriate heading text in histogram display canvas */
  pw_text(hst_pw, 64, 18, PIX_SRC|PIX_COLOR(2), dispfont, hst_header);

  /* Display appropriate heading text for edge detector results canvas*/
  pw_text(edf_hdr_pw, 1, 12, PIX_SRC|PIX_COLOR(2), dispfont, edf_header);

  reset_all_panels();   /* Display default control panel strings */

  /* Read in matrix coefficients for neural network edge detectors (V1) */
  get_edf_matrix_elements();

  /* Read in matrix coefficients for neural network offset detectors (V2) */
  get_V2_matrix_elements();

  /* Allocate memory for information used by the ART2 classifier */
  ART_start (TOT_SPECTRUM_SIZE);

  if(ok_img_file) display_proc();        /* Activate display and interaction */
}

reset()
{
  u_char *reset_image_block();
```

```
  image = reset_image_block(image, size_x, size_y, "input");
  hst_image =
    reset_image_block(hst_image, hist_width, hist_height, "histogram");
  edf_image =
    reset_image_block(edf_image, EDF_PLOT_WIDTH, hist_height, "edf spectrum");
  reset_all_panels();
}

                          /* ---------- */
                          /* Procedures */
                          /* ---------- */

/*-----------------------------------------------------------------------*/

void mk_ART2_panel()
{
  int pnl_x;

  /* Create new frame to hold the panel */
  ART2_panel =
    window_create(base_frame,       PANEL,
                  WIN_RIGHT_OF, control_panel, 0);

  /* Display appropriate heading text in ART2 control panel canvas */
  ART2_hdr_item  = panel_create_item(ART2_panel, PANEL_TEXT,
                                     PANEL_LABEL_STRING,
                                       "Controls for ART 2 Classifier",
                                     PANEL_LABEL_FONT, dispfont,
                                     PANEL_LABEL_X, ATTR_COL(15),
                                     PANEL_LABEL_Y, 10,
                                     PANEL_VALUE_DISPLAY_LENGTH, 0, 0);

  LGN_mult_item  = panel_create_item(ART2_panel, PANEL_TEXT,
                                     PANEL_LABEL_STRING,
                                       "Multiplier for LGN Sum:",
                                     PANEL_LABEL_Y, ATTR_ROW(2),
                                     PANEL_LABEL_X, ATTR_COL(0),
                                     PANEL_VALUE, LGN_mstr,
                                     PANEL_VALUE_Y, ATTR_ROW( 2),
                                     PANEL_VALUE_X, ATTR_COL(27),
                                     PANEL_VALUE_DISPLAY_LENGTH, NUM_STR_LEN,
                                     PANEL_NOTIFY_PROC, LGN_mult_proc, 0);

  V2_mult_item   = panel_create_item(ART2_panel, PANEL_TEXT,
                                     PANEL_LABEL_STRING,
                                       "Multiplier for V2 signals:",
                                     PANEL_VALUE, V2_mstr,
                                     PANEL_VALUE_DISPLAY_LENGTH, NUM_STR_LEN,
                                     PANEL_NOTIFY_PROC, V2_mult_proc, 0);

  LTM_input_item = panel_create_item(ART2_panel, PANEL_TEXT,
                                     PANEL_LABEL_STRING, "LTM input file:",
                                     PANEL_VALUE,        old_LTM_file,
                                     PANEL_VALUE_DISPLAY_LENGTH, FNL,
                                     PANEL_NOTIFY_PROC,  old_LTM_proc, 0);

  LTM_output_item = panel_create_item(ART2_panel, PANEL_TEXT,
                                      PANEL_LABEL_STRING, "LTM save  file:",
                                      PANEL_VALUE,        new_LTM_file,
                                      PANEL_VALUE_DISPLAY_LENGTH, FNL,
                                      PANEL_NOTIFY_PROC,  new_LTM_proc, 0);

  /* Set Active Window Item to Field for the "LTM Input File" */
  window_set(ART2_panel, PANEL_CARET_ITEM, LTM_input_item, 0);

  /* Create "button" items for interactive recall and storage of LTM values */

  panel_create_item(ART2_panel, PANEL_BUTTON,
                    PANEL_NOTIFY_PROC,  read_LTM,
                    PANEL_LABEL_IMAGE,
                    panel_button_image(control_panel,"Fetch LTM Values",17,0),
                    0);

  panel_create_item(ART2_panel, PANEL_BUTTON,
                    PANEL_NOTIFY_PROC,  write_LTM,
                    PANEL_LABEL_IMAGE,
```

```
                    panel_button_image(control_panel,"Store LTM Values",17,0),
                    PANEL_ITEM_Y, (ATTR_ROW( 6)-4),
                    PANEL_ITEM_X, (ATTR_COL(20)-2),
                    0);

/* Scale contents of ART 2 control panel to fit in available space */
window_fit(ART2_panel);

pnl_x = (int)window_get(ART2_panel, WIN_X);
pnl_x += 16;

  window_set(ART2_panel, WIN_X, pnl_x, 0);
}

void LGN_mult_proc()
{
  strncpy (LGN_mstr, (char *)panel_get_value(LGN_mult_item), NUM_STR_LEN);
  sscanf  (LGN_mstr, "%f", &LGN_wt);
}

void V2_mult_proc()
{
  strncpy (V2_mstr, (char *)panel_get_value(V2_mult_item), NUM_STR_LEN);
  sscanf  (V2_mstr, "%f", &V2_wt);
}

void old_LTM_proc()
{
  char *err_str;
  int num_char;

  strncpy (old_LTM_file, (char *)panel_get_value(LTM_input_item), FNL);

  /* Close any LTM input file which may have been opened previously */
  if (LTM_source_file != NULL)
    fclose(LTM_source_file);

  LTM_source_file = fopen(old_LTM_file, "r");
  if (LTM_source_file == NULL)
    {
      num_char = 49 + strlen(old_LTM_file);
      err_str = (char *)calloc(num_char, sizeof(char));
      strcpy(err_str, "Problem opening file \"");
      strcat(err_str, old_LTM_file);
      strcat(err_str, "\" as source for LTM traces.");
      message (err_str);
      free ((char *)err_str);
    }
}

void new_LTM_proc()
{
  char *err_str;
  int num_char;

  strncpy (new_LTM_file, (char *)panel_get_value(LTM_output_item), FNL);

  /* Close any LTM output file which may have been opened previously */
  if (LTM_output_file != NULL)
    fclose(LTM_output_file);

  LTM_output_file = fopen(new_LTM_file, "w");
  if (LTM_output_file == NULL)
    {
      num_char = 54 + strlen(new_LTM_file);
      err_str = (char *)calloc(num_char, sizeof(char));
      strcpy(err_str, "Problem opening file \"");
      strcat(err_str, new_LTM_file);
      strcat(err_str, "\" for storage of new LTM traces.");
      message (err_str);
      free ((char *)err_str);
    }
}

void read_LTM()
{
  char *err_str;
  int num_vals, num_writ, num_char;
```

```
  if (LTM_source_file == NULL)
    message("Source file for LTM trace values has not been opened.");
  else
    {
     /* Read in number of category (F2) nodes that were associated
                       with particular input patterns                    */
     num_writ = fread (&Nactv, sizeof(int), 1, LTM_source_file);
     if (num_writ != 1)
       {
         num_char = 54 + strlen(old_LTM_file);
         err_str = (char *)calloc(num_char, sizeof(char));
         strcpy
           (err_str, "Problem reading number of assigned nodes from file \"");
         strcat(err_str, old_LTM_file);
         strcat(err_str, "\".");
         message (err_str);
         free ((char *)err_str);
       }

     else

              /* Read in actual LTM memory trace values */
       {
         num_vals = 2 * TOT_SPECTRUM_SIZE * nF2;
         num_writ = fread (z[0], sizeof(float), num_vals, LTM_source_file);
         if (num_writ != num_vals)
           {
             num_char = 46 + strlen(old_LTM_file);
             err_str = (char *)calloc(num_char, sizeof(char));
             strcpy(err_str, "Problem reading LTM trace values from file \"");
             strcat(err_str, old_LTM_file);
             strcat(err_str, "\".");
             message (err_str);
             free ((char *)err_str);
           }
       }
    }

              /* Reset all information about the LTM output file
                        to prevent inadvertent reuse.          */
  fclose(LTM_source_file);
  LTM_source_file = NULL;
  strcpy(old_LTM_file, "");
  panel_set(LTM_input_item, PANEL_VALUE, old_LTM_file, 0);
}

void write_LTM()
{
  char *err_str;
  int num_vals, num_writ, num_char;

  if (LTM_output_file == NULL)

    message("File to receive LTM trace values has not been opened.");
  else
    {
     /* Save number of category (F2) nodes that have been associated
                       with particular input patterns                    */
     num_writ = fwrite (&Nactv, sizeof(int), 1, LTM_output_file);
     if (num_writ != 1)
       {
         num_char = 52 + strlen(new_LTM_file);
         err_str = (char *)calloc(num_char, sizeof(char));
         strcpy
           (err_str, "Problem writing number of assigned nodes to file \"");
         strcat(err_str, new_LTM_file);
         strcat(err_str, "\".");
         message (err_str);
         free ((char *)err_str);
       }

     else

              /* Save actual LTM memory trace values */
       {
```

```
            num_vals = 2 * TOT_SPECTRUM_SIZE * nF2;
            num_writ = fwrite (z[0], sizeof(float), num_vals, LTM_output_file);
            if (num_writ != num_vals)
              {
                num_char = 44 + strlen(new_LTM_file);
                err_str = (char *)calloc(num_char, sizeof(char));
                strcpy(err_str, "Problem writing LTM trace values to file \"");
                strcat(err_str, new_LTM_file);
                strcat(err_str, "\".");
                message (err_str);
                free ((char *)err_str);
              }
          }
      }

              /* Reset all information about the LTM output file
                          to prevent inadvertent reuse.              */
  fclose(LTM_output_file);
  LTM_output_file = NULL;
  strcpy(new_LTM_file, "");
  panel_set(LTM_output_item, PANEL_VALUE, new_LTM_file, 0);
}

vlt_open()   /* Activate video lookup tables for image display window */

/*    Modified by KG Heinemann on 06-MARCH-1989 and 07-MARCH-1989
   to include colormap information from the image VLT, the base frame,
   and all pre-existing windows in the VLT ramp display */
{
  int i, color_fetch_index;

  /* Set up video lookup table for the histogram plot display */
  set_hist_vlt();

  /* Set up video lookup table for the display of edge detector results */
  set_edf_vlt();

  /* Close any video lookup table file that was already opened */
  fclose(fp_vlt);

  fp_vlt = fopen(vlt_fname,"r");  /* Open new video lookup table file */

  /* Set video lookup table for actual image */
  set_colormap(img_pw, fp_vlt, vlt_fname, 0);

  /* Set video lookup table for VLT encoding display */

  /* Extract colormap values set by pre-existing windows and
     store them in corresponding locations of the colormap array
     (This is accomplished without upsetting the window manager
          by fetching the colormap entries one at a time) */

  /* Start colormap retrieval at the next element after
     the end of the base frame's colormap segment */
  color_fetch_index = bas_cms.cms_size;

  for(i=(bas_cms.cms_addr+bas_cms.cms_size); i<VLT_SIZE; ++i)
    {
      pw_getcolormap(bas_pw, color_fetch_index, 1, red+i, green+i, blue+i);
      ++color_fetch_index;
    }

  pw_setcmsname(vlt_pw, "ramp_vlt");
  pw_putcolormap(vlt_pw, 0, VLT_SIZE, red, green, blue);

  /* Transfer colormap information from pixrect to the pixwin
     which has been allocated for the VLT encoding display */
  draw_rainbow(vlt_pw);
}

int display_proc()
{
  int retval;

    /* Allocate memory to store image */
  image = reset_image_block(image, size_x, size_y, "input");
```

```c
    /* Release any memory assigned to the V2 image */
    if (V2_hidden_layer != NULL )
      {
        free((ACTIVATION_DATA_TYPE *)V2_hidden_layer);
        V2_hidden_layer = NULL;
      }
    retval = show_image(batch_flg);
    return (retval);
}

void clear_canvas_proc()
{
  pw_writebackground(img_pw, img_x_offs, img_y_offs,
                   IMG_CANVAS_X_SIZE, IMG_CANVAS_Y_SIZE, PIX_SRC);

  /* Clear any histogram displayed for the old image */
  pw_writebackground(hst_pw, 0, 24, hist_width, HST_PLOT_HEIGHT, PIX_SRC);

  /* Set flag to indicate that histogram information is now invalid */
  validhst_flag = 0;

  /* Clear any edge detector specturm displayed for the old image */
  pw_writebackground(edf_pw, 0, 0, EDF_PLOT_WIDTH, HST_WIN_HEIGHT, PIX_SRC);

        /* Set flags to indicate that edge detector spectrum (V1)
            and centering signal (V2) information is now invalid  */
  valid_V1_flag = valid_V2_flag = 0;

}

void quit_proc()
{
    window_set(base_frame, FRAME_NO_CONFIRM, TRUE, 0);
    window_destroy(base_frame);
}

#include <errno.h>

void batch_cwd_proc()
{
  strncpy (seq_cwd, (char *)panel_get_value(batch_cwd_item), FNL);
}

void batch_fil_proc()
{
  int stat, read_seq();
  void seqfil_reset();

        /*    Attempt to switch current working directory to
              directory path specified for the batch sequence file */

  switch( chdir(seq_cwd) )
    {
    case 0:    /* Successful Switch */

       strncpy (seq_fname, (char *)panel_get_value(batch_fil_item), FNL);

       if (batch_seq==NULL)
         batch_seq = (struct sequence *)calloc(1, sizeof (struct sequence));

       if (batch_seq==NULL)
         {
           message ("Could not allocate sequence structure.\n");
           seqfil_reset();
         }
       else
         {
           stat = read_seq(batch_seq, seq_fname);
           if (stat<0)
             {
               message ("Could not open sequence file.\n");
               seqfil_reset();
             }
         }
       break;
    case ENOTDIR:
       message("Non-directory component in path to batch sequence file!");
```

```
      break;
    default:
      message ("Cannot access directory specified for batch sequence file!");
      strcpy(seq_cwd, cwd);
          panel_set(batch_cwd_item, PANEL_VALUE, seq_cwd, 0);
          break;
        }
  }

  void seqfil_reset()
  {
    strcpy(seq_fname, "");
    panel_set(batch_fil_item, PANEL_VALUE, seq_fname, 0);
  }
/* image_util.c          Printe on 18-December-1989 */
/*
   Image I/O and Display Manipulation Routines for the Software Testbed
    Developed by KG Heinemann and P.N. DiCaprio to Test R.L. Harvey's
        Neural Network Architecture for General Object Recognition

       "vio.c" Modified by KG Heinemann on 18-MAY-1989 to facilitate
           use of M.M. Menon's "STD" file format for input images

  "imgbox_io.c" adapted from "vio.c" by KG Heinemann on 08-AUGUST-1989

        "vio.c" and "imgbox_io.c" merged into one set of routines
                on 27-September-1989 and 28-September-1989.
*/

#include        <stdio.h>
#include        <math.h>
#include        <string.h>
#include        <suntool/sunview.h>
#include        <suntool/canvas.h>
#include        <suntool/panel.h>
#include        <suntool/scrollbar.h>
#include        <local/STD.h>

#include        "image_io.h"

/* Look up table for displaying an 8 bit image with a compressed colormap */
int     img_display_value[VLT_SIZE];

int     npnl_rows;   /* Number of rows already specified in a given panel */

/*------------------------------------------------------------------------*/

/*                      Variables for Image File I/O                     */

char    cwd[FNL];                 /* Current working directory */
char    img_fname[FNL];           /* Image file name */

/* ASCII representation of pattern index number within the image input file */
char    imgnum_str[4];

Panel   control_panel;
Panel_item
  cwd_item, file_item, num_item, hdr_item, vlt_item, csr_item, zoom_item;

int     ok_img_file=0;

FILE *fp_img;            /* Stream pointer for ASCII input files */

/* Parameter blocks for manipulation of "STD" files */
int     std_ioblk[32], std_pblk[32];

/* Flag to indicate whether input image is coming from a "non-STD" file */
int nonstd_flag;

/* Flag to indicate whether an "STD" input image file has been opened */
u_char std_open;

char header[FNL];  /* Publically Available Portion of "STD" file header */
/*------------------------------------------------------------------------*/

/*          Variables for Dynamically Allocated Image Memory Blocks       */
```

```
/* Error Message String for the "reset_image_block" Subroutine */
char *rib_err_string =
  "reset_image_block: insufficient memory available for                    ";
char *image_str = " image.\n";

u_char  *image=NULL;          /* dynamically allocated image array */

/*------------------------------------------------------------------------*/

/*                       Image Display Parameters                          */

Frame   base_frame;   /* Structure to describe  top level window  in SunView */
Canvas  img_canvas;   /* Structure to describe image display area in SunView */
Pixwin  *bas_pw, *img_pw;
Menu    img_menu;
Cursor  img_cursor;

int     size_x=IMAGE_WIDTH,            /* input image width  */
        size_y=IMAGE_HEIGHT;           /* input image height */
int     zoom_x=1, zoom_y=1;            /* zoom magnification */

/* Horizontal and Vertical Offsets of Displayed Image within Image Canvas */
int i, img_x_offs, img_y_offs;

/* Thickness of a Default Scroll Bar for Proper Sizing of the Image Canvas */
int     scroll_bar_thickness;

/*------------------------------------------------------------------------*/

        /* Information Pertaining to Global Video Look-Up Table Values
                  and Handles for Color Bar Display Area            */

char    vlt_fname[FNL];         /* VLT file name */
FILE    *fp_vlt;                /* Stream pointer for VLT file name */
Canvas  vlt_canvas;
Pixwin  *vlt_pw;
u_char  red[VLT_SIZE], green[VLT_SIZE], blue[VLT_SIZE];

/*------------------------------------------------------------------------*/

int               box_flg = -1;        /* flag for defined image box */
char              box_str[FNL];
Panel_item        img_box_item;
struct BOX_STRUCT img_box;

/*------------------------------------------------------------------------*/

        /* Variables for Manipulating Error Message Strings */

char *err_str;
char *oper_prefix = "Problem while opening ";
char *oper_suffix = " input image file!!";

char *FilNOpen_str = "read_image: file not open!";
char *ASC_rderr_str = "read_image: Error reading data from ASCII image file!";
char *STD_rderr_str = "read_image: Error reading data from STD image file!";
char *wrong_num_str =
"Image number     is out of range; the input file contains only     patterns! ";

/*------------------------------------------------------------------------*/

setup_windows(argc, argv, frlabstr)
int     argc;
char    **argv;
char    *frlabstr;
{

  struct {u_char rval, gval, bval} fgnd_color;
  fgnd_color.rval=162; fgnd_color.gval=0; fgnd_color.bval=223;

  /* Create handle for the overall display */
  base_frame = window_create(NULL, FRAME, FRAME_LABEL, frlabstr,
                             FRAME_EMBOLDEN_LABEL, TRUE,
                             FRAME_FOREGROUND_COLOR, fgnd_color,
                             WIN_X, 4, WIN_Y, 0, FRAME_ARGS, argc, argv, 0);
```

```
/* Create panel for input image selection and display manipulation */
control_panel = window_create(base_frame, PANEL, 0);

              /* At start of control panel construction,
                  set number of preceding lines to zero          */
npnl_rows = 0;

/* Create lines for communication about the batch control file, if any */
npnl_rows += batch_file_info();

/* Create text lines to communicate display status information */

cwd_item =
  panel_create_item(control_panel, PANEL_TEXT,
                    PANEL_LABEL_STRING, "Image Directory:",
                    PANEL_VALUE,        cwd,
                    PANEL_VALUE_DISPLAY_LENGTH, FNL,
                    PANEL_NOTIFY_PROC,   cwd_proc, 0);
++npnl_rows;

file_item =
  panel_create_item(control_panel, PANEL_TEXT,
                    PANEL_LABEL_STRING,  "Image File Name:",
                    PANEL_VALUE,        img_fname,
                    PANEL_VALUE_DISPLAY_LENGTH, FNL,
                    PANEL_NOTIFY_PROC,   img_open_proc, 0);
++npnl_rows;

num_item = panel_create_item(control_panel, PANEL_TEXT,
                             PANEL_LABEL_STRING, "Image Number:",
                             PANEL_VALUE,        imgnum_str,
                             PANEL_VALUE_DISPLAY_LENGTH, FNL,
                             PANEL_NOTIFY_PROC,  std_pnum_proc, 0);
++npnl_rows;

hdr_item = panel_create_item(control_panel, PANEL_TEXT,
                             PANEL_LABEL_STRING, "File Header:",
                             PANEL_VALUE,        header,
                             PANEL_VALUE_DISPLAY_LENGTH, FNL, 0);
++npnl_rows;
vlt_item =
  panel_create_item(control_panel, PANEL_TEXT,
                    PANEL_LABEL_STRING,  " VLT  File Name:",
                    PANEL_VALUE,         vlt_fname,
                    PANEL_VALUE_DISPLAY_LENGTH, FNL,
                    PANEL_NOTIFY_PROC,    vlt_open_proc, 0);
++npnl_rows;

npnl_rows += aux_file_info();

csr_item = panel_create_item(control_panel, PANEL_TEXT,
                             PANEL_LABEL_STRING, "Cursor position:",
                             PANEL_VALUE_DISPLAY_LENGTH, FNL,
                             0);
++npnl_rows;

zoom_item = panel_create_item(control_panel, PANEL_TEXT,
                              PANEL_LABEL_STRING, "Current Zoom Factors:",
                              PANEL_VALUE_DISPLAY_LENGTH, FNL,
                              0);
++npnl_rows;

img_box_item = panel_create_item(control_panel, PANEL_TEXT,
                                 PANEL_LABEL_STRING,  "Image box:",
                                 PANEL_VALUE,         box_str,
                                 PANEL_VALUE_DISPLAY_LENGTH, FNL, 0);
++npnl_rows;

/* Set Active Window Item to the "Image File" field */
window_set(control_panel, PANEL_CARET_ITEM, file_item, 0);

/* Create "button" items to receive interactive user instructions */

panel_create_item(control_panel, PANEL_BUTTON,
                  PANEL_NOTIFY_PROC,  display_proc,
                  PANEL_LABEL_IMAGE,
```

```
                  panel_button_image(control_panel,"Display",9,0),
                  PANEL_ITEM_Y,          (ATTR_ROW(npnl_rows) - 10),
                  PANEL_ITEM_X,          ATTR_COL(0),
                  0);

panel_create_item(control_panel, PANEL_BUTTON,
                  PANEL_NOTIFY_PROC,  clear_canvas_proc,
                  PANEL_LABEL_IMAGE,
                  panel_button_image(control_panel,"Clear",7,0),
                  0);

panel_create_item(control_panel, PANEL_BUTTON,
                  PANEL_NOTIFY_PROC,  zoom_proc,
                  PANEL_LABEL_IMAGE,
                  panel_button_image(control_panel,"Zoom",6,0),
                  0);

panel_create_item(control_panel, PANEL_BUTTON,
                  PANEL_NOTIFY_PROC,  unzoom_proc,
                  PANEL_LABEL_IMAGE,
                  panel_button_image(control_panel,"UnZoom",8,0),
                  0);
panel_create_item(control_panel, PANEL_BUTTON,
                  PANEL_NOTIFY_PROC,  quit_proc,
                  PANEL_LABEL_IMAGE,
                  panel_button_image(control_panel,"Quit",6,0),
                  0);

aux_buttons();

mk_messwin();      /* Create window for displaying error messages */

/* Scale contents of control panel to fit in available space */
window_fit(control_panel);

aux_panels();

      /* Set Up SunView Canvas for Display of Input Image */

/* Create canvas area for displaying the video lookup table */
vlt_canvas =
  window_create(base_frame,            CANVAS,
              WIN_X,                      0,
              CANVAS_AUTO_SHRINK, FALSE,
              CANVAS_HEIGHT,      VLT_HEIGHT,
              WIN_WIDTH,          VLT_SIZE,
              WIN_HEIGHT,         VLT_HEIGHT,    0);

/* Create crosshair image cursor */
img_cursor = cursor_create(CURSOR_SHOW_CROSSHAIRS,  TRUE,
                         CURSOR_CROSSHAIR_LENGTH,  15 ,
                         CURSOR_CROSSHAIR_GAP,      5 ,  0);

/* Determine thickness of a default scroll bar */
scroll_bar_thickness = (int) scrollbar_get(SCROLLBAR, SCROLL_THICKNESS);

/* Creat canvas area for displaying the actual image */
img_canvas =
  window_create(base_frame, CANVAS,
              WIN_X,                                   0,
              CANVAS_AUTO_SHRINK,                   FALSE,
              CANVAS_WIDTH,                  IMG_CANVAS_X_SIZE,
              CANVAS_HEIGHT,                 IMG_CANVAS_Y_SIZE,
              WIN_WIDTH,             IMAGE_WIDTH  + scroll_bar_thickness,
              WIN_HEIGHT,            IMAGE_HEIGHT + scroll_bar_thickness,
              WIN_VERTICAL_SCROLLBAR,        scrollbar_create(0),
              WIN_HORIZONTAL_SCROLLBAR,      scrollbar_create(0),
              WIN_EVENT_PROC,                   xy_proc,
              WIN_CURSOR,                     img_cursor,
              0);

aux_windows();        /* Create any other windows used in this application */

/* Horizontal and vertical scaling for overall window */
window_fit(base_frame);
```

```
  bas_pw = (Pixwin *)window_get(base_frame, WIN_PIXWIN);
  vlt_pw = canvas_pixwin(vlt_canvas);
  img_pw = canvas_pixwin(img_canvas);
}

set_colormap(pw, fp, name, first_loc)
     /* Modified on 02-MAR-1989 by KGH so that the size and location of
            the colormap segment are specified by arguments */

Pixwin  *pw;
FILE    *fp;
char    *name;
int     first_loc;      /* Index of first colormap location to set */

/* Set up video look up table for image display */
{
  int i, r, g, b, color_val, color_dec;

  color_dec = (VLT_SIZE + IMG_VLT_SIZE - 1) / IMG_VLT_SIZE;

  if(fp==NULL)    /* No VLT file - default is gray scale */
    {
     color_val = VLT_SIZE - 1;
     for(i=first_loc; i<IMG_VLT_SIZE; ++i)
       {
         red[i] = green[i] = blue[i] = color_val;
         color_val-=color_dec;
       }
       pw_setcmsname (pw, name);
    }
  else
    /* Read color value triplets from file and store in arrays */
    {
     for(i=first_loc; i<IMG_VLT_SIZE; ++i)
       {
         fscanf(fp,"%d %d %d",&r,&g,&b);
         red[i]=r; green[i]=g; blue[i]=b;
       }
     rewind(fp);
    }

  /* Assign video look up table to the color map */
  pw_putcolormap(pw, first_loc, IMG_VLT_SIZE,
                 red   + first_loc,
                 green + first_loc,
                 blue  + first_loc);

  /* Set up look up table for compressing the image before display */

  color_val = (VLT_SIZE - 1) / color_dec;
  for(i=0; i<VLT_SIZE; ++i)
    img_display_value[i] = color_val - (i / color_dec);
}

draw_rainbow(pw)
Pixwin  *pw;
/* Write out sequence of vertical bars to activate actual VLT display */
{
  int i;
  for(i=0; i<VLT_SIZE; ++i)
    pw_rop(pw, i,0, 1, VLT_HEIGHT, PIX_SRC | PIX_COLOR(i), (Pixrect *)0, 0, 0);
}

reset_all_panels()
/* Refresh default entries on display of master control panel */
{
  panel_set(file_item, PANEL_VALUE, img_fname,  0);
  panel_set(num_item,  PANEL_VALUE, imgnum_str, 0);
  panel_set(hdr_item,  PANEL_VALUE, header,     0);
  panel_set(vlt_item,  PANEL_VALUE, vlt_fname,  0);
}

int img_open(batch_flg)

/* Flag to indicate whether calling program is operating in a batch mode */
u_char batch_flg;
```

```
{
  void imgfil_reset();

  int   str_index, stat, retval, emes_len;
  char  ftype[9], class_name[10];
  char  *suf_char_ptr, *std_hdbf;

  retval = 1;           /* Set default return value to indicate success */

  /* Extract file type suffix from name of image file */

  str_index=0;
  if ((suf_char_ptr = strchr(img_fname, '.')) != NULL)
    while(*suf_char_ptr != '\0')
      if(str_index<8)
        ftype[str_index++] = *(++suf_char_ptr);
      else
        {
          ftype[str_index] = '\0';
          break;
        }

  if (nonstd_flag=strcmp(ftype, "std"))
    {
      fp_img = fopen(img_fname, "r");
      if(fp_img==NULL)
        {
          /* Allocate memory and construct an actual error message string */
          emes_len = strlen(oper_prefix) + strlen(oper_suffix) + 5;
          err_str = (char *)calloc(emes_len, sizeof(char));
          strcpy (err_str, oper_prefix);
          strcat (err_str, "ASCII");
          strcat (err_str, oper_suffix);

 /* Display error message in pop-up window if operating in interactive mode */
          if (!batch_flg)
            {
              message(err_str);
              free((char *)err_str);
            }

          retval = 0;          /* Set return value to indicate a problem */
          imgfil_reset();
        }
      else
        {
          size_x = 512;
          size_y = 512;
        }
    }
  else
    {
      std_open = FALSE;
      std_hdbf = (char *)calloc(FNAMLEN, sizeof(char));

      stat = init_rd_std(std_ioblk, std_pblk, std_hdbf, img_fname);
      if (stat<0)
        {
          /* Allocate memory and construct an actual error message string */
          emes_len = strlen(oper_prefix) + strlen(oper_suffix) + 3;
          err_str = (char *)calloc(emes_len, sizeof(char));
          strcpy (err_str, oper_prefix);
          strcat (err_str, "STD");
          strcat (err_str, oper_suffix);

 /* Display error message in pop-up window if operating in interactive mode */
          if (!batch_flg)
            {
              message(err_str);
              free((char *)err_str);
            }

          retval = 0;          /* Set return value to indicate a problem */
          imgfil_reset();
        }
      else
```

```
        {
          std_open = TRUE;
          size_x = std_pblk[2];
          size_y = std_pblk[1];

          for(str_index=0; str_index<(FNL-1); ++str_index)
            header[str_index] = std_hdbf[str_index];
          header[FNL] = '\0';
        }
      free((char *)std_hdbf);
    }
  return(retval);
}

void imgfil_reset()
{
  strcpy(img_fname, "");
  panel_set(file_item, PANEL_VALUE, img_fname, 0);
}

/* ------------------------------------------------------------ */

        /* Routine to perform dynamic allocation of image arrays */

u_char *reset_image_block(img_ptr, x_dim, y_dim, type_string)

u_char *img_ptr;         /* Pointer to memory region designated for image */
int x_dim, y_dim;        /* Dimensions of specified image */
char *type_string;       /* Image type information for use in error message */

{
  int aux_index, err_index;

  /* Release any memory which has already been assigned for the image */
  if (img_ptr != NULL )
    free((char *)img_ptr);

  /* Allocate new memory block for image storage */
  img_ptr = (u_char *)calloc(x_dim*y_dim, sizeof(u_char));
  if (img_ptr==NULL )
    {
      err_index=53;
      for(aux_index=0; type_string[aux_index]!='\0'; aux_index++)
        rib_err_string[err_index++] = type_string[aux_index];
      for(aux_index=0; image_str[aux_index]!='\0'; aux_index++)
        rib_err_string[err_index++] = image_str[aux_index];
      rib_err_string[err_index] = '\0';
      errmess(rib_err_string);
    }
  return(img_ptr);
}

/* ------------------------------------------------------------ */

                /* Read in image data from file */

int read_image(batch_flg)

/* Flag to indicate whether calling program is operating in a batch mode */
u_char batch_flg;

{
  int  stat;
  char class_name[10];  /* STD Pattern Class */
  char reqnum_str[4], filnum_str[4];

  if (nonstd_flag)
    {
      if (fp_img)        /* Check whether image file is open */
        {
          /* Check for error in reading image */
          if (fread(image, 512*512, 1, fp_img)!=1) /* Error occurred */
            {
              /* Issue message if operating in interactive mode */
              if (!batch_flg) message(ASC_rderr_str);

              /* Otherwise set error message pointer to appropriate string
```

```
            and set return status value to indicate a "data read" error */
          else
            {
              err_str = ASC_rderr_str;
              stat = DATA_RD_ERROR;
            }

          ok_img_file = FALSE;
        }
      else {              /* Image data acquired successfully */
        size_x = 512;
        size_y = 512;
        ok_img_file = TRUE;
        stat = IMG_FILE_OK;
      }

    }
  else              /* Image file not open */
    {
      /* Issue message if operating in interactive mode */
      if (!batch_flg) message(FilNOpen_str);

      /* Otherwise set error message pointer to appropriate string
         and set return status value to indicate that file not open */
      else
        {
          err_str = FilNOpen_str;
          stat = FIL_NOT_OPN_ERR;
        }

      ok_img_file = FALSE;
    }
}
else
  {
    if (std_open)     /* Check whether "STD" image file is open */
      {

 /* Check whether "std" file contains the requested pattern number */
      if ( (std_ioblk[1] > std_pblk[12]) || std_ioblk[1]<1)

        {                             /* NO */

            /* Format error message string */
          sprintf(reqnum_str, "%3d", std_ioblk[1]);
          strncpy(wrong_num_str+13, reqnum_str, 3);
          sprintf(filnum_str, "%3d", std_pblk[12]);
          strncpy(wrong_num_str+63, filnum_str, 3);

    /* Display error message in pop-up if working interactively */
          if (!batch_flg) message(wrong_num_str);

    /* Otherwise set error message pointer to string for bad pattern no.
       and set return status value to indicate pattern number out of range */
          else
            {
              err_str = wrong_num_str;
              stat = BAD_STD_PAT_NUM;
            }

          ok_img_file = FALSE;
        }
      else
        {
          stat = read_std(std_ioblk, std_pblk, class_name, image);
          if (stat != IMG_FILE_OK)
            {
            /* Issue message if operating in interactive mode*/
              if (!batch_flg) message (STD_rderr_str);

            /* Otherwise set error message pointer to appropriate string */
              else err_str = STD_rderr_str;

              ok_img_file = FALSE;
            }
          else
```

```
                {
                  size_x = std_pblk[2];
                  size_y = std_pblk[1];
                  ok_img_file = TRUE;
                }
            }
        }
      else
        {
          /* Issue message if operating in interactive mode */
          if (!batch_flg) message(FilNOpen_str);

          /* Otherwise set error message pointer to appropriate string
             and set return status value to indicate that file not open */
          else
            {
              err_str = FilNOpen_str;
              stat = FIL_NOT_OPN_ERR;
            }

          ok_img_file = FALSE;
        }
    }
  return (stat);
}

int show_image(batch_flg)

/* Flag to indicate whether calling program is operating in a batch mode */
u_char batch_flg;
{
  int retval;
  int autozoom;
  char zoom_str[13];

  retval = read_image(batch_flg);  /* Attempt to read image data from file */
  if(retval == IMG_FILE_OK)      /* If image successfully acquired from file */
    {
      clear_canvas_proc();
      autozoom = min ((IMAGE_WIDTH/size_x), (IMAGE_HEIGHT/size_y));
      zoom_x = zoom_y = autozoom;
      put_image();                       /* Send it to the appropriate pixwin */
      sprintf(zoom_str, "X: %2d  Y: %2d", zoom_x, zoom_y);
      panel_set(zoom_item, PANEL_VALUE, zoom_str, 0);
    }
  reset_all_panels();   /* Display control panel defaults again */
  return(retval);
}

put_image()
{
  int img_indx;

  /* Dynamically allocated array for compressed display image */
  u_char *dsp_image=NULL;

  /* Allocate memory block to store compressed display image */
  dsp_image = (u_char *)calloc(size_x*size_y, sizeof(u_char));
  if(dsp_image==NULL )
    errmess("put_image: insufficient memory for compressed image.");
  /* Use pre-established look up table to compress the image for display */
  for(img_indx=0; img_indx<(size_x * size_y); ++img_indx)
    dsp_image[img_indx] = (u_char)img_display_value[image[img_indx]];

  /* Compute offsets to center image on visible portion of canvas */
  img_x_offs = max ( (IMAGE_WIDTH  - (zoom_x * size_x)) / 2, 0);
  img_y_offs = max ( (IMAGE_HEIGHT - (zoom_y * size_y)) / 2, 0);

  pw_put_image(img_pw, img_x_offs, img_y_offs, size_x, size_y, dsp_image);

  /* Release memory block which holds the compressed image */
  if(dsp_image != NULL ) free((char *)dsp_image);
}

pw_put_image(pw,dx,dy,ew,ns,image)
Pixwin          *pw;
```

```
int             dx,dy;
u_char          *image;
int             ns,ew;
{
  struct pixrect *mem_point(), *im_pix;
  int   i,j,k=0;

  pw_batch_on(pw);
  if (zoom_x == 1 && zoom_y == 1)
    {
      im_pix = mem_point(ew, ns, 8, image);
      pw_write(pw, dx, dy, ew, ns, PIX_SRC, im_pix, 0, 0);
    }

  else

    {
      for(j=0; j<ns; ++j)
        for(i=0; i<ew; ++i, ++k)
          {
            pw_rop(pw, dx+i*zoom_x, dy+j*zoom_y, zoom_x, zoom_y,
                   PIX_SRC | PIX_COLOR(image[k]), (Pixrect *)0, 0, 0);
          }
    }
    pw_batch_off(pw);

  /* set image box */
  img_box.x0 = dx;
  img_box.y0 = dy;
  img_box.x1 = ew;
  img_box.y1 = ns;
  sprintf(box_str, "x0 = %d, y0 = %d, x1 = %d, y1 = %d",
          img_box.x0, img_box.y0, (img_box.x1-1), (img_box.y1-1));
  panel_set(img_box_item, PANEL_VALUE, box_str, 0);
}

setup_img_menu()   /* Create menu for image zoom functions */
{
  img_menu = menu_create (MENU_STRINGS, "Zoom", "UnZoom", "Clear", 0, 0);
}

void zoom_proc()
{
    clear_canvas_proc();
    zoom_x *= 2;
    zoom_y *= 2;
    put_Image();

}
void unzoom_proc()
{
    clear_canvas_proc();
    zoom_x /= 2;
    zoom_y /= 2;
    if(zoom_x<1) zoom_x=1;
    if(zoom_y<1) zoom_y=1;
    put_image();
}

void img_open_proc()
{
  strncpy (img_fname,  (char *)panel_get_value(file_item), FNL);
  img_open(0);
  reset();
  clear_canvas_proc();
}

void std_pnum_proc()
{
  strncpy (imgnum_str, (char *)panel_get_value(num_item), 3);
  sscanf  (imgnum_str, "%d", std_iob[k+1]);
  clear_canvas_proc();
}

void vlt_open_proc()
{
```

```
    strncpy(vlt_fname,(char *)panel_get_value(vlt_item), FNL),
    vlt_open();
}

void xy_proc (cv, event)
Canvas  cv;
Event   *event;
{
  char  string[50];
  int   ix, iy;
  int   value;
  int   item_number;

  static int crosshair_toggle=TRUE;

  switch(event_id(event))
    {
      case MS_RIGHT:
                       /* --------- */
        item_number = (int)menu_show(img_menu,img_canvas,event,0);
        switch(item_number-1)
          {
            case 0:
              zoom_proc();
              break;
            case 1:
              unzoom_proc();
              break;
            case 2:
              clear_canvas_proc();
              break;
          }
        break;

      case MS_MIDDLE:
                       /* ---------- */
        crosshair_toggle =
          (int)cursor_get(img_cursor, CURSOR_SHOW_CROSSHAIRS);

        if(event_is_down(event))
          {
            if(crosshair_toggle==TRUE)
              crosshair_toggle=FALSE;
            else
              crosshair_toggle=TRUE;
            cursor_set(img_cursor,
                       CURSOR_SHOW_CROSSHAIRS, crosshair_toggle,
                       0);
            window_set(img_canvas, WIN_CURSOR, img_cursor, 0 );
          }
        break;

      case MS_LEFT:
                       /* -------- */
        if (event_is_down(event))
          {
            if (box_flg > -1) draw_box();

            img_box.x = (event_x(event) - img_x_offs) / zoom_x;
            img_box.y = (event_y(event) - img_y_offs) / zoom_y;

            change_box();

            box_flg = (box_flg == 0) ? 1 : 0;
          }
        break;

      default:
                       /* ------- */
        img_box.x = (event_x(event) - img_x_offs) / zoom_x;
        img_box.y = (event_y(event) - img_y_offs) / zoom_y;
        if (box_flg == 0)
          {
            draw_box();
            change_box();
          }
```

```
        value = pw_get(img_pw,
                       ((img_box.x*zoom_x) + img_x_offs),
                       ((img_box.y*zoom_y) + img_y_offs) );
        ix = img_box.x;
        iy = img_box.y;

        sprintf(string,"x=%4d y=%4d value=%3d", ix, iy, value);

        panel_set(csr_item, PANEL_VALUE, string, 0);
        break;
    }
}

change_box()
{
  img_box.x0 = img_box.x - ((img_box.size_x - 1) /2) - 1;
  img_box.y0 = img_box.y - ((img_box.size_y - 1) /2) - 1;
  img_box.x1 = img_box.x0 + img_box.size_x;
  img_box.y1 = img_box.y0 + img_box.size_y;

  draw_box();

  sprintf(box_str, "x0 = %d, y0 = %d, x1 = %d, y1 = %d",
          img_box.x0, img_box.y0, (img_box.x1-1), (img_box.y1-1));
  panel_set(img_box_item, PANEL_VALUE, box_str, 0);
}

draw_box()
{
  int   scr_x0, scr_y0, scr_x1, scr_y1;

  scr_x0 = (zoom_x * img_box.x0) + img_x_offs;
  scr_y0 = (zoom_y * img_box.y0) + img_y_offs;
  scr_x1 = (zoom_x * img_box.x1) + img_x_offs;
  scr_y1 = (zoom_y * img_box.y1) + img_y_offs;

  pw_vector(img_pw, scr_x0, scr_y0, scr_x1, scr_y0, PIX_SRC ^ PIX_DST, 255);
  pw_vector(img_pw, scr_x1, scr_y0, scr_x1, scr_y1, PIX_SRC ^ PIX_DST, 255);
  pw_vector(img_pw, scr_x0, scr_y1, scr_x1, scr_y1, PIX_SRC ^ PIX_DST, 255);
  pw_vector(img_pw, scr_x0, scr_y0, scr_x0, scr_y1, PIX_SRC ^ PIX_DST, 255);
}

#include <errno.h>
void cwd_proc()
{

  switch( chdir((char *)panel_get_value(cwd_item)) )
    {
    case 0:
      strncpy(cwd,(char *)panel_get_value(cwd_item), FNL);
      return;
    case ENOTDIR:
      errmess("cwd_proc: component of path not directory");
      break;
    default:
      panel_set(cwd_item,PANEL_VALUE,cwd,0);
      break;
    }
}
        /* verrtool.c            Printed on 18-December-1989 */
/*
  error message for image viewer viewtool
*/

        /* -- Includes -- */

#include <stdio.h>
#include <suntool/sunview.h>
#include <suntool/canvas.h>
#include <suntool/panel.h>

#include "viewtool.h"

                /* ------------- */
                /* Error Message */
                /* ------------- */
```

```
mk_messwin()
{
  /* Create new frame window to display error message */
  message_frame =
    window_create(base_frame,       FRAME,
                  FRAME_SHOW_LABEL, TRUE,      /* Show label in frame border */
                  FRAME_LABEL,      "Error:",
                  WIN_X,            20,
                  WIN_Y,            20,
                  WIN_SHOW,         FALSE,     0);

  /* Create a panel within the new window */
  message_panel =
    window_create(message_frame, PANEL,
                  PANEL_LAYOUT,  PANEL_HORIZONTAL, 0);

  /* Create a reply button for the user */
  panel_create_item(message_panel,     PANEL_BUTTON,
                    PANEL_NOTIFY_PROC, reset_mess_proc,
                    PANEL_LABEL_IMAGE,
                      panel_button_image(control_panel,"Reset",5,0),
                    0);

  /* Allocate screen space for message string and get its handle */
  msg_item = panel_create_item(message_panel, PANEL_MESSAGE, 0);
}

message(s)
char    *s;
{
  Frame mess_frame;

  panel_set(msg_item,PANEL_LABEL_STRING, s, 0);
  window_fit(message_panel);
  window_fit(message_frame);
  window_set(message_frame,WIN_SHOW,TRUE,0);
  window_set(base_frame,WIN_SHOW,FALSE,0);
  window_loop(message_frame);
}

void reset_mess_proc()
{
    window_set(base_frame,WIN_SHOW,TRUE,0);
    window_set(message_frame,WIN_SHOW,FALSE,0);
    window_return(0);
}

errmess(s)
char    *s;
{
    printf("%s",s);
    quit_proc();
    exit(0);
}
        /* filter.c              Printed on 18-December-1989 */
/*
  filter routines for viewtool
*/


        /* -- Includes -- */

#include        <stdio.h>
#include        <suntool/sunview.h>
#include        <suntool/canvas.h>
#include        <suntool/panel.h>
*include        <local/STD.h>

#include "image_io.h"
#include "cellview.h"
#include "netparam.h"

 /*     Header file to make Long Term Memory trace information
     and ART 2 result descriptors available to outside programs */
#include "LTM.h"
```

```
/*
   Subroutine "mk_img_proc_panel" modified by KG Heinemann
   on 17-February-1989 to add button for histogram generator

   Further modifications by KG Heinemann on 25-April-1989 to add
   button for RL Harvey's Neural Network Edge Detection Algorithms
*/

Panel_item EDF_item, thresh_item, roll_item;

/* Flag to indicate whether the program is operating in a batch mode */
u_char batch_flg=0;

FILE *log_chan=NULL, *fopen();

mk_img_proc_panel()
{
  int item_X;   /* Horizontal Coordinate of Specific Panel Items */
  int item_Y;   /*  Vertical  Coordinate of Specific Panel Items */

  /* First create panel to specify Image Processing Options;
     Set Default Width Equal to Width of the Control Panel */

  /* Create new frame to hold the panel */
  img_proc_panel =
    window_create(base_frame,       PANEL,
                  WIN_BELOW,  control_panel,
                  WIN_WIDTH,  IMG_CANVAS_X_SIZE,
                  WIN_X,             0,       0);

  /* Then install filter selection buttons */

  panel_create_item(img_proc_panel,   PANEL_BUTTON,
                    PANEL_NOTIFY_PROC, mean_filter_proc,
                    PANEL_LABEL_IMAGE,
                      panel_button_image(control_panel,"Mean filter",11,0),
                    0);
  panel_create_item(img_proc_panel, PANEL_BUTTON,
                    PANEL_NOTIFY_PROC,  median_filter_proc,
                    PANEL_LABEL_IMAGE,
                      panel_button_image(control_panel,"Median filter",13,0),
                    0);
  panel_create_item(img_proc_panel, PANEL_BUTTON,
                    PANEL_NOTIFY_PROC,  set_binary_filter_proc,
                    PANEL_LABEL_IMAGE,
                      panel_button_image(control_panel,"Threshold",9,0),
                    0);
  panel_create_item(img_proc_panel, PANEL_BUTTON,
                    PANEL_NOTIFY_PROC,  make_IRP_histogram,
                    PANEL_LABEL_IMAGE,
                      panel_button_image
                        (control_panel, "Generate Histogram", 18, 0),
                    0);
  panel_create_item(img_proc_panel, PANEL_BUTTON,
                    PANEL_NOTIFY_PROC, hst_equalize,
                    PANEL_LABEL_IMAGE,
                      panel_button_image
                        (control_panel, "Equalize Histogram", 18, 0),
                    0);
  EDF_item =
    panel_create_item(img_proc_panel, PANEL_BUTTON,
                      PANEL_NOTIFY_PROC, spiral_map,
                      PANEL_LABEL_IMAGE,
                         panel_button_image
                            (control_panel, "NN Edge Detectors", 17, 0),
                      0);
  panel_create_item(img_proc_panel, PANEL_BUTTON,
                    PANEL_NOTIFY_PROC, detect_offset,
                    PANEL_LABEL_IMAGE,
                      panel_button_image
                        (control_panel, "NN Offset Detectors", 19, 0),
                    0);
  panel_create_item(img_proc_panel, PANEL_BUTTON,
                    PANEL_NOTIFY_PROC, ITC1,
                    PANEL_LABEL_IMAGE,
```

```
              panel_button_image
                (control_panel, "ART2 Classifier", 15, 0),
            0);

  /* Create sliding scale lever for user input of threshold value */
  thresh_item =
    panel_create_item(img_proc_panel,     PANEL_SLIDER,
                      PANEL_LABEL_STRING, " Binary Threshold:",
                      PANEL_MIN_VALUE,         0,
                      PANEL_MAX_VALUE,    VLT_SIZE-1,
                      PANEL_VALUE,        binary_thresh,
                      PANEL_NOTIFY_PROC,  binary_filter_proc,
                      0);

  /* Create sliding scale lever for user to roll the VLT */

  /* Extract Vertical Coordinate of "thresh_item" */
  item_Y = (int)panel_get(thresh_item, PANEL_ITEM_Y);

  /* Compute Desired Vertical Coordinate for "roll_item" */
  item_Y += 20;
  roll_item =
    panel_create_item(img_proc_panel,     PANEL_SLIDER,
                      PANEL_LABEL_STRING, "     Roll VLT    :",
                      PANEL_MIN_VALUE,         0,
                      PANEL_MAX_VALUE,    VLT_SIZE-1,
                      PANEL_ITEM_X,            3,
                      PANEL_ITEM_Y,          item_Y,
                      PANEL_VALUE,             0,
                      PANEL_NOTIFY_PROC,  roll_vlt_proc,
                      0);

  /* Extract Horizontal Coordinate of the "NN Edge Detectors" Button */
  item_X = (int)panel_get(EDF_item, PANEL_ITEM_X) - 96;

  item_Y -= 10;

  panel_create_item(img_proc_panel, PANEL_BUTTON,
                    PANEL_NOTIFY_PROC, IRP_auto_proc,
                    PANEL_LABEL_IMAGE,
                      panel_button_image
                        (control_panel, "Full IRP Sequence", 19, 0),
                    PANEL_ITEM_Y, item_Y,
                    PANEL_ITEM_X, item_X, 0);

  panel_create_item(img_proc_panel, PANEL_BUTTON,
                    PANEL_NOTIFY_PROC, IRP_batch_proc,
                    PANEL_LABEL_IMAGE,
                      panel_button_image
                        (control_panel, "Run from Batch File", 21, 0),
                    PANEL_ITEM_Y, item_Y, 0);

  /* Scale contents of algorithm control panel to fit in available space */
  window_fit(img_proc_panel);
}

int binary_thresh=128;

void mean_filter_proc()
{
  int   i,j,k;
  u_char        *old_image;

  old_image = (u_char *)calloc(size_x*size_y,sizeof(u_char));
  if(old_image==NULL)
    errmess("mean_filter_proc: no room for old_image");

  for(k=0; k<size_x*size_y; ++k)
    old_image[k]=image[k];

  pw_put_image(img_pw,0,0,size_x,size_y,old_image);

  for(i=1; i<size_x-1; ++i)
    for(j=1; j<size_y-1; ++j)
      image[size_x*i+j] = 0.2*(old_image[size_x*i+j]+
```

```
                                          old_image[size_x*i+j+1]+
                                          old_image[size_x*i+j-1]+
                                          old_image[size_x*(i+1)+j]+
                                          old_image[size_x*(i-1)+j]);

  free((char *)old_image);

  put_image();
}

void median_filter_proc()
{
  int   i,j,k;
  u_char        *old_image;

  old_image = (u_char *)calloc(size_x*size_y,sizeof(u_char));
  if(old_image==NULL)
    errmess("mean_filter_proc: no room for old_image");

  for(k=0; k<size_x*size_y; ++k)
    old_image[k]=image[k];

  pw_put_image(img_pw,0,0,size_x,size_y,old_image);

  for(i=1; i<size_x-1; ++i)
    for(j=1; j<size_y-1; ++j)
      image[size_x*i+j] = median(5,
                                 (int)old_image[size_x*i+j],
                                 (int)old_image[size_x*i+j+1],
                                 (int)old_image[size_x*i+j-1],
                                 (int)old_image[size_x*(i+1)+j],
                                 (int)old_image[size_x*(i-1)+j]);

  free((char *)old_image);

  put_image();
}

void binary_filter_proc()
{
  int   k;
  u_char        *t_image;

  binary_thresh = (int)panel_get_value(thresh_item);

  t_image = (u_char *)calloc(size_x*size_y,sizeof(u_char));

  for(k=0; k<size_x*size_y; ++k)
    {
      if(image[k]>binary_thresh)
        t_image[k]=VLT_SIZE-1;
      else
        t_image[k]=0;
    }
  pw_put_image(img_pw,0,0,size_x,size_y,t_image);

  free((char *)t_image);
}

void set_binary_filter_proc()
{
  int   k;

  binary_thresh = (int)panel_get_value(thresh item);
  for(k=0; k<size_x*size_y; ++k)
    {
      if(image[k]>binary_thresh)
        image[k]=VLT_SIZE-1;
      else
        image[k]=0;
    }
  put_image();
}


void roll_vlt_proc()
```

```
{
  u_char        nred[VLT_SIZE],ngreen[VLT_SIZE],nblue[VLT_SIZE];
  int           i;
  int           roll_val;

  roll_val = (int)panel_get_value(roll_item);

  for(i=1; i<VLT_SIZE; ++i)
    {
      nred[i]=red[(i+roll_val)%VLT_SIZE];
      ngreen[i]=green[(i+roll_val)%VLT_SIZE];
      nblue[i]=blue[(i+roll_val)%VLT_SIZE];
    }

  pw_putcolormap(img_pw,0,VLT_SIZE,nred,ngreen,nblue);
}

#include "activation.h"

void ITC1 ()
{
  int loop_index;
  ACTIVATION_DATA_TYPE  LGN_sum();

  /* Bias offset to make all spectrum values non-negative */
  ACTIVATION_DATA_TYPE  bias_val;

  if (!valid_V1_flag)

    message ("You need to generate \"edge detector features\" (NN Edge Detectors
) before running the ART 2 classifier!!");

  else

    if (!valid_V2_flag)

      message ("You need to generate \"offset signals\" (NN Offset Detectors) be
fore running the ART2 classifier!!");

    else

      {
        /* Invoke routine to compute normalized sum and weight the result */
        frwd_feature[0] = LGN_wt * LGN_sum();

        bias_val = pow (2.0, 32);  /* Set bias offset to a very large value */

        /*    Find smallest value among the V1 and V2 outputs
           and subtract the result from each V1 and V2 component
           to produce a pattern where the smallest value is zero */
        for (loop_index=V2_SPECTRUM_OFFSET; loop_index<TOT_SPECTRUM_SIZE;
             ++loop_index)
          if (frwd_feature[loop_index] < bias_val)
            bias_val = frwd_feature[loop_index];

        for (loop_index=V2_SPECTRUM_OFFSET; loop_index<TOT_SPECTRUM_SIZE;
             ++loop_index)
          frwd_feature[loop_index] -= bias_val;

        /* Apply designated weighting factor to the V2 signals */
        for (loop_index=V2_SPECTRUM_OFFSET; loop_index<EDF_SPECTRUM_OFFSET;
             ++loop_index)
          frwd_feature[loop_index] *= V2_wt;

        run_ART(TOT_SPECTRUM_SIZE, frwd_feature, &log_class_info, log_chan);
      }
}

/* Routine to run full sequence of IRP algorithms without user intervention */
int IRP_auto_proc()
{
  int retval;
  if ((retval = display_proc()) == IMG_FILE_OK)
    {
      make_IRP_histogram();
      hst_equalize();
      make_IRP_histogram();
```

```
    spiral_map();
    detect_offset();
    if (!valid_V2_flag) retval = V2_CALC_ERR;
    else ITC1();
  }
  return (retval);
}

      /*     Routine to run full sequence of IRP_algorithms on
         a series of images specified in a "sequence" control file */

#include <errno.h>

void IRP_batch_proc()
{
  int   stat, init_seq_pat(), loop_index, last_delim_ptr, fn_str_len;
  char *fil_path, *cwd_sav_str, *log_path, *batch_err_str;

/* Check whether sequence control information has been acquired successfully */

  if (seq_fname[0] == '\0')            /* NO! */
    message("Sequence control file not specified properly.\n");

  else           /* Sequence control information OK */
    {
     /* Translate sequence control information into a series of image requests
                     and check for errors */
     stat = init_seq_pat(batch_seq);
     if (stat<0) message ("Error interpreting sequence information.\n");

     else      /* Successful translation of sequence control information */
       {

       /* Construct name of file to receive log of processing results */

       /* Allocate memory to hold log file path name */
       log_path = (char *)calloc(2*FNL, sizeof(char));

       /* Set "directory" component of the log file path name
          to store results information in the same place as
               the batch sequence information */
       strcpy(log_path, seq_cwd);
       strcat(log_path,   "/"  );        /* Add final slash delimiter */

             /*   Parse name of batch sequence source file
                into "file name" and "file type" components  */

       /*   Determine whether a file type is specified by searching
          the batch sequence file string for its last period character.
          If the period character is found, append all the preceding
          characters (the file name portion) onto the log file path
          name.  Otherwise treat the entire sequence file string as a
             file name and append that onto the log file path name.   */

       if ((last_delim_ptr = strrchr(seq_fname, '.')) != NULL)

/* Compute relative position of the last period character by subtracting
           the absolute address of the batch sequence file string       */
         fn_str_len = last_delim_ptr - (int)seq_fname;

       else fn_str_len = strlen(seq_fname);

       strncat(log_path, seq_fname, fn_str_len);  /* Copy file name */

       /* Add period delimiter and "log" file type suffix */
       strcat (log_path, ".log");

       log_chan = fopen(log_path, "w");      /* Open the actual log file */
       if (log_chan == NULL)
         {
           fn_str_len = 56 + strlen(log_path);
           batch_err_str = (char *)calloc(fn_str_len, sizeof(char));
           strcpy(batch_err_str, "Problem opening file \"");
           strcat(batch_err_str, log_path);
           strcat(batch_err_str, "\" for storage of batch result log.");
           message (batch_err_str);
           free ((char *)batch_err_str);
```

```
        }
      else
        {
          /* Save current path name for the image working directory  */
          cwd_sav_str = (char *)calloc(FNL, sizeof(char));
          strcpy(cwd_sav_str, cwd);

          /* Allocate memory to image file path name */
          fil_path = (char *)calloc(FNAMLEN, sizeof(char));

              /* Set flag to indicate that the program
                     is operating in a batch mode */
          batch_flg = 1;
              /* Loop over the specified number of images */
        for (loop_index=0; loop_index<batch_seq->num_entries;
              ++loop_index)
           {

      /* Clear image display canvas to avoid confusion between
             visible scene and current pattern specification     */
             clear_canvas_proc();

   /* Write sequence entry number to the batch results log file */
             fprintf(log_chan, "%d - ", (loop_index+1));

        /* Extract image file path name and pattern number
                from the sequence control information       */
             get_seq_info(batch_seq, loop_index, fil_path, std_ioblk+1);

/* Parse image file path name into "directory" and "file name" components */

   /*    Determine whether a directory is specified by searching
      the image file path name for its last forward slash character.
      If the forward slash character is found, copy the directory
     specification into the image "current working directory" string.
      Otherwise, leave the "cwd" string unchanged and use the same
           directory that was specified for the last image.          */

             if ((last_delim_ptr = strrchr(fil_path, '/')) != NULL)
               {

   /* Compute relative position of last forward slash character
      by subtracting the absolute address of the file path name   */
                 fn_str_len = last_delim_ptr - (int)fil_path;

                 strncpy (cwd, fil_path, fn_str_len);        /* Copy */

   /* Increment "last_delim_ptr" so that it points to beginning
       of the file name component of the image file path name     */
                 ++last_delim_ptr;
               }

             else  /* No explicit directory specification */

   /* In order to facilitate proper handling of the image file name,
          set "last_delim_ptr" so that it points to beginning
                   of the image file path name.                   */
               last_delim_ptr = (int)fil_path;

   /* Change "current working directory" to current specifications,
       check for success or failure, and take appropriate action.   */
             switch(chdir(cwd))
               {

   /*              Successful change of the "cwd" -
          verify existence and format of the image file */
               case 0:
                 panel_set(cwd_item, PANEL_VALUE, cwd, 0);

                 /* Write current image file directory
                      to the batch results log file     */
                 fprintf(log_chan, "%s", cwd);
   /* Extract file name component from image file path name */
       strcpy(img_fname, (char *)last_delim_ptr);
```

```
/* Write current image file name to the batch results log file */
        fprintf(log_chan, "/%s", img_fname);

    /* Verify that image file exists and has correct format */
        stat = img_open(1);
        if (stat>0)                /* Image file is OK */
          {
            /* Show file name on control panel */
            panel_set(file_item, PANEL_VALUE, img_fname, 0);

    /* Format pattern number for display on control panel  */
            sprintf(imgnum_str, "%3d", std_ioblk[1]);
            panel_set(num_item, PANEL_VALUE, imgnum_str, 0);

            /* Write current "std" pattern number
                 to the batch results log file    */
            fprintf(log_chan, " image no. %d", std_ioblk[1]);

        /* Execute image processing algorithm suite */
            stat = IRP_auto_proc();
            if (stat == IMG_FILE_OK)
              {
                fprintf(log_chan,
                        "\n     Pattern mapped to node %d ",
                        log_class_info.cat_node);
                fprintf(log_chan. "and learned in %d passes;",
                        log_class_info.num_pass);
                fprintf(log_chan, " R = %6.4f.",
                        log_class_info.R_value);
              }
            else
              fprintf(log_chan, "\n     %s", err_str);
          }

        else      /* Problem accessing current image file */
          {
            fprintf(log_chan, "\n     %s", err_str);
            free ((char *)err_str);
          }

        break;
      case ENOTDIR:
        fprintf(log_chan,
                " Some component of path %s is not a directory.",
                cwd);
        break;
      default:
        fprintf(log_chan,
                " Unable to access directory %s.", cwd);
        break;
      }
    /* Advance to next line in the batch results log file */
    fprintf(log_chan, "\n");

    /* Flush all batch result log information into file */
    fflush(log_chan);

          }       /*   End of loop over images    */

        /* Release memory used to hold image file path name */
        free((char *)fil_path);

    /* Restore image working directory path name that was active
       before processing files from the sequence control file */
        strcpy(cwd, cwd_sav_str);
        free((char *)cwd_sav_str);

        switch(chdir(cwd))
          {
          case 0:
            panel_set(cwd_item, PANEL_VALUE, cwd, 0);
            break;
          default:
            batch_err_str = (char *)calloc(48+strlen(cwd), sizeof(char));
            strcpy(batch_err_str,
                   "Problem restoring original working directory \"");
```

```
                strcat(batch_err_str, cwd);
                strcat(batch_err_str, "\".");
                message (batch_err_str);
                free ((char *)batch_err_str);
                break;
              }

          }
        fclose(log_chan);   /* Close batch results log file */
        log_chan = NULL;    /* Indicate batch results log file unspecified */
      }
    }
}

        /* median.c              Printed on 18-December-1989 */

#include <stdio.h>
#include <varargs.h>
int
median(va_alist)
va_dcl
{
    va_list     ap;
    int         i,n,med;
    int         *pix;
    int         compar();

    va_start(ap);

    n = va_arg(ap,int);
    pix = (int *)calloc(n,sizeof(int));
    if(pix==NULL)
        errmess("median: cant allocate pix[]");
    for(i=0; i<n; ++i)
        pix[i] = va_arg(ap,int);

    va_end(ap);

    qsort( (char *)pix,n,sizeof(int),compar);

    if(n%2==0)
        med = (pix[n/2]+pix[n/2+1])/2;
    else
        med = pix[n/2];

    return(med);
}

compar(px,py)
int     *px,*py;
{
    return(*px - *py);
}
        /* IRP_histogram.c       Printed on 18-December 1989 */

#include <stdio.h>

#include <suntool/sunview.h>
#include <suntool/canvas.h>
#include <suntool/panel.h>

#include "image_io.h"
#include "cellview.h"

/* Define external image histogram array */
int IRP_hist_data[VLT_SIZE];

int hstmax;     /* Maximum count in the intensity histogram */
int hmax_loc;   /* Intensity value corresponding to maximum count */

        /* Flag to Indicate Whether Histogram Array Contents
                are Valid for the Current Image            */
u_char validhst_flag = 0;

set_hist_vlt()
```

```
/* Set up video look up table for display of histogram plot */
{

  int i;

  /* Get ID name of base frame's color map segment */
  pw_getcmsname(bas_pw, bas_cmsname);

  /* Get description of base frame's color map segment using its ID name */
  pw_getcmsdata(bas_pw, &bas_cms, &i);

  /* Extract base frame color map entries and store them in color map arrays
       at positions corresponding to the segment's absolute location
                     in the global color map table */
  pw_getcolormap(bas_pw, 0, bas_cms.cms_size,
                    red   + bas_cms.cms_addr,
                    green + bas_cms.cms_addr,
                    blue  + bas_cms.cms_addr);

          /* Expand Base Frame's Color Map by Two Entries
                in Order to Accomodate More Colors */

          /* Slide existing background color specification
             to beginning of the enlarged colormap segment */

  i = bas_cms.cms_addr - bas_cms.cms_size;
  red   [i] = red   [bas_cms.cms_addr];
  green [i] = green [bas_cms.cms_addr];
  blue  [i] = blue  [bas_cms.cms_addr];
  red[bas_cms.cms_addr] = green[bas_cms.cms_addr] = blue[bas_cms.cms_addr] = 0;

  /* Destroy previous base frame colormap segment information */
  pw_setcmsname (bas_pw, bas_cmsname);
  pw_putcolormap(bas_pw, 0, 0, red, green, blue);

        /* Reload Enlarged Base Frame Color Map Segment */
  pw_putcolormap(bas_pw, 0, 2*bas_cms.cms_size,  red+i, green+i, blue+i);
  /* Acquire new descriptors for modified base frame color map segment */
  pw_getcmsdata(bas_pw, &bas_cms, &i);

  /* Assign base frame color map segment to the histogram display canvas */
  pw_setcmsname(hst_pw, bas_cmsname);

          /* Reload original base frame color map values
             into the histogram display canvas segment */
  pw_putcolormap(hst_pw, 0, bas_cms.cms_size,
                    red   + bas_cms.cms_addr,
                    green + bas_cms.cms_addr,
                    blue  + bas_cms.cms_addr);
}

void make_IRP_histogram()
{
  int i, j, hst_img_base_ptr, hst_img_offset, new_pix, last_y, nfill,
      fill_start, fill_end;
  float scale_fac;

/* Generate and Plot new Histogram Only if Current Information is Not Valid */
  if (!validhst_flag)
    {
      /* Clear array for storing image histogram data */
      for(i=0; i<VLT_SIZE; ++i)
        IRP_hist_data[i]=0;

      /* Compile histogram of image */
      for(i=0; i<(size_x*size_y); ++i)
        IRP_hist_data[image[i]]++;

      /* Set Flag to Indicate that Histogram Information is Now Valid */
      validhst_flag = 1;

      /* Find maximum histogram count */
      hstmax = 0;
      for(i=0; i<VLT_SIZE; i++)
        if(IRP_hist_data[i]>hstmax)
          {
```

```
         hstmax=IRP_hist_data[i];
         hmax_loc = i;
        }

    scale_fac = (float)HST_HEIGHT / (float)hstmax;

    /* Clear histogram plot image */

    for(i=0; i<N_HST_DISPLAY_PIXELS; i++)
      hst_image[i]=0;

    /* Generate new histogram plot image */

    hst_img_base_ptr = PLOT_BORDER_WIDTH*(hist_height+1);
    last_y =0;
    for (i=0; i<VLT_SIZE; i++)
      {
        /* Compute current display image position and fill it in */
        hst_img_offset =
          HST_HEIGHT - (int)(scale_fac * (float)IRP_hist_data[i]);
          hst_image[(new_pix=hst_img_base_ptr+hst_img_offset)]=3;

        /* Fill in current column from current y-value to the preceeding one */
          nfill = (int)(scale_fac * (float)(last_y - IRP_hist_data[i]));
          if(nfill)
            {
              fill_start = min(new_pix, (new_pix - nfill));
              fill_end   = max(new_pix, (new_pix - nfill));
              for(j=fill_start; j<fill_end; j++)
                hst_image[j]=3;
            }

          last_y = IRP_hist_data[i];
          hst_img_base_ptr+=hist_height;
        }

      hst_img_offset=0;
      pw_batch_on(hst_pw);
      for(i=0; i<hist_width; i++)
        {
          for (hst_img_base_ptr=24; hst_img_base_ptr<HST_WIN_HEIGHT;
               ++hst_img_base_ptr)
            {
              pw_rop(hst_pw, i, hst_img_base_ptr, 1, 1,
                     PIX_SRC | PIX_COLOR(hst_image[hst_img_offset]),
                     (Pixrect *)0, 0, 0);
              ++hst_img_offset;
            }
        }
      pw_batch_off(hst_pw);
    }
}

void hst_equalize()
{
      /* Routine to Enhance Image Contrast by Altering Pixel Values
           to Produce a Linear Stretching of the Global Histogram
   so that it Fills the Entire Dynamic Range of Intensity Values (0 - 255) */

      /* Coded by KG Heinemann between 14-July-1989 and 19-July-1989 */

  int clip_thresh, cum_sum, lowerlim, upperlim, win_row, win_col,
        first_row, first_col, last_row, last_col, icol, irow, index;
  float scale_fac, denom;

  float *new_image=NULL;

  /* Determine whether a valid histogram is available by checking the value of
     "validhst_flag"; if not, issue an error message and exit from routine */
  if (validhst_flag)
    {

      /* Define lower limit of the intensity interval to be stretched
         by finding the closest point left of the histogram peak where
              the histogram count falls to 1% of the peak value          */
```

```
    clip_thresh = (int)(0.01 * (float)hstmax);
    for (index=hmax_loc; (index>-1) && (IRP_hist_data[index]>clip_thresh);
         index--)
      lowerlim = index;

              stretching to the "modified" intensity values */

        for (index=0; index<(size_x*size_y); index++)
          if      (new_image[index]<lowerlim) image[index] =0;
          else if (new_image[index]>upperlim) image[index] =(VLT_SIZE-1);
          else          image[index] =
            (int)((scale_fac * (new_image[index] - (float)lowerlim)) + 0.5);

        free ((float *)new_image);    /* Release temporary image memory */
        new_image = NULL;
      }

    /* Clear away the old image and display the equalized one */
    clear_canvas_proc();
    put_image();      /* Send it to the appropriate pixwin */
  }
  else
    message("Histogram for current image has not been created.");
}

       /* IRP_edge_detector.c  Printed on 18-December-1989 */

/* Code to implement neural network oriented edge detectors (V1) for IRP */

#include <stdio.h>
#include <math.h>

#include <suntool/sunview.h>
#include <suntool/canvas.h>
#include <suntool/panel.h>

#include "image_io.h"
#include "cellview.h"
#include "netparam.h"

/*------------------------------------------------------------------------*/
/*  Code to set up video look up table for display of edge detector results  */

set_edf_vlt()

/*

   Created on 25-April-1989 by KG Heinemann

   This subroutine uses the same colormap segment that was assigned
   to the base frame and the histogram display canvas in subroutine
   "set_hist_vlt". It assumes that actions in that part of the code
   already have been performed, so it will not work properly if that
   subroutine has not been called previously.
*/
{
  /* Assign base frame color map segment to the canvas which
     has been designated for display of edge detector results */

  pw_setcmsname(edf_pw, bas_cmsname);

          /* Reload original base frame color map values
             into the histogram display canvas segment */
  pw_putcolormap(edf_pw, 0, bas_cms.cms_size,
                  red   + bas_cms.cms_addr,
                  green + bas_cms.cms_addr,
                  blue  + bas_cms.cms_addr);
}
/*------------------------------------------------------------------------*/


        /* Flag to Indicate Whether Edge Detector Spectrum
             (V1) Values are Valid for the Current Image    */
u_char valid_V1_flag = 0;

   /*----------------------------------------------------------------------*/
   /*                                                                      */
   /*    Connection weights for detection of horizontal and vertical edges    */
```

```
/*                                                                    */
/*--------------------------------------------------------------------*/

/* Strengths for connections between the hidden units */
float horzvert_A_wts [N_HIDDEN_NEURONS * N_HIDDEN_NEURONS];

/* Strengths for connections between input units and hidden units */
float
  horzvert_B_wts [INPUT_WINDOW_SIZE * INPUT_WINDOW_SIZE * N_HIDDEN_NEURONS];

/* Strengths for connections between hidden units and output units */
float horzvert_C_wts [N_HIDDEN_NEURONS * N_OUTPUTS];

/* Strengths for connections between input units and output units */
float horzvert_D_wts [INPUT_WINDOW_SIZE * INPUT_WINDOW_SIZE * N_OUTPUTS];

            /*----------------------------------------------------*/
            /*                                                    */
            /*   Connection weights for detection of diagonal edges  */
            /*                                                    */
            /*----------------------------------------------------*/

/* Strengths for connections between the hidden units */
float diagonal_A_wts [N_HIDDEN_NEURONS * N_HIDDEN_NEURONS];

/* Strengths for connections between input units and hidden units */
float
  diagonal_B_wts [INPUT_WINDOW_SIZE * INPUT_WINDOW_SIZE * N_HIDDEN_NEURONS];

/* Strengths for connections between hidden units and output units */
float diagonal_C_wts [N_HIDDEN_NEURONS * N_OUTPUTS];

/* Strengths for connections between input units and output units */
float diagonal_D_wts [INPUT_WINDOW_SIZE * INPUT_WINDOW_SIZE * N_OUTPUTS];


/* Rectified signals transmitted by the input neurons */
ACTIVATION_DATA_TYPE
  input_neuron_signal[INPUT_WINDOW_SIZE * INPUT_WINDOW_SIZE];

/* Activation levels for the hidden neurons */
ACTIVATION_DATA_TYPE hidden_neuron_signal[N_HIDDEN_NEURONS];

/* Activation levels for the output neurons */
ACTIVATION_DATA_TYPE output_neuron_signal[N_OUTPUTS];

/* Array to store component of neuron activation caused by input stimulus */
ACTIVATION_DATA_TYPE B_or_D_fi[MAX_NEURONS];

/* Array to store previous activation levels for iterative computation */
ACTIVATION_DATA_TYPE previous_activation[MAX_NEURONS];

/* Array to store rectified input signals */
ACTIVATION_DATA_TYPE sigrect[MAX_NEURONS];

/* Array to Store Collected Input Signals for the ART2 classifier */
ACTIVATION_DATA_TYPE frwd_feature[TOT_SPECTRUM_SIZE];

/* Temporary Storage for Use While Re-Ordering the Input Window Array */
ACTIVATION_DATA_TYPE scratch_pixel;

/* Number of image pixels to skip when moving from the end of one row
        in the input window to the beginning of the next one         */
int row_skip_increment;

        /* Offset from start of input window to begin calculation
           of input signals for the orthogonal orientations */
int offset_for_orthogonal_orientations;

/* Index to Indicate Next Unused Location in the "Edge Feature" Array
            and Cumulative Entry Counter for that Array */
int ftr_counter;

/*--------------------------------------------------------------------*/
/*                                                                    */
/*  Utility routine to read in pre-established connection strength valuess  */
/*                     from file on disk                              */
```

```
/*                                                                          */
/*--------------------------------------------------------------------------*/

/*              Created by KG Heinemann on 08-May-1989                      */

char *edf_matrix_err_str =
  "\nError reading coefficients for                          ",
     *emestr_suffix = "matrix!\n\n",
     *upright_str  = "upright",
     *diagonal_str = "diagonal",
     *space_str = " ",
     *A_str="A", *B_str="B", *C_str="C", *D_str="D";

void get_edf_matrix_elements()

{
  FILE *matrix_data_file, *fopen();
  int num_read, err_index, aux_index, type_index;

  /* Attempt to open matrix coefficient data file */
  matrix_data_file = fopen("gray_edf_matrices.bin", "r");
  if(matrix_data_file==NULL)
    errmess("\nError opening edge detector matrix coefficient file!\n\n");

/* Prepare error message string for the horizontal and vertical orientations */
  err_index=31;
  for(aux_index=0; upright_str[aux_index]!='\0'; aux_index++)
    edf_matrix_err_str[err_index++] = upright_str[aux_index];
  edf_matrix_err_str[err_index++] = space_str[0];
  type_index = err_index;
  for(aux_index=0; aux_index<2; aux_index++)
    edf_matrix_err_str[err_index++] = space_str[0];
  for(aux_index=0; emestr_suffix[aux_index]!='\0'; aux_index++)
    edf_matrix_err_str[err_index++] = emestr_suffix[aux_index];
  edf_matrix_err_str[err_index] = '\0';

  num_read = fread(horzvert_A_wts, sizeof(float),
                   N_HIDDEN_NEURONS * N_HIDDEN_NEURONS, matrix_data_file);
  if(num_read != N_HIDDEN_NEURONS * N_HIDDEN_NEURONS)
    {
      edf_matrix_err_str[type_index] = A_str[0];
      errmess(edf_matrix_err_str);
    }

  num_read = fread(horzvert_B_wts, sizeof(float),
                   INPUT_WINDOW_SIZE * INPUT_WINDOW_SIZE * N_HIDDEN_NEURONS,
                   matrix_data_file);
  if(num_read != INPUT_WINDOW_SIZE * INPUT_WINDOW_SIZE * N_HIDDEN_NEURONS)
    {
      edf_matrix_err_str[type_index] = B_str[0];
      errmess(edf_matrix_err_str);
    }

  num_read = fread(horzvert_C_wts, sizeof(float),
                   N_HIDDEN_NEURONS * N_OUTPUTS, matrix_data_file);
  if(num_read != N_HIDDEN_NEURONS * N_OUTPUTS)
    {
      edf_matrix_err_str[type_index] = C_str[0];
      errmess(edf_matrix_err_str);
    }

  num_read = fread(horzvert_D_wts, sizeof(float),
                   INPUT_WINDOW_SIZE * INPUT_WINDOW_SIZE * N_OUTPUTS,
                   matrix_data_file);
  if(num_read != INPUT_WINDOW_SIZE * INPUT_WINDOW_SIZE * N_OUTPUTS)
    {
      edf_matrix_err_str[type_index] = D_str[0];
      errmess(edf_matrix_err_str);
    }

      /* Prepare error message string for the diagonal orientations */
  err_index=31;
  for(aux_index=0; diagonal_str[aux_index]!='\0'; aux_index++)
    edf_matrix_err_str[err_index++] = diagonal_str[aux_index];
  edf_matrix_err_str[err_index++] = space_str[0];
  type_index = err_index;
```

```
for(aux_index=0; aux_index<2; aux_index++)
  edf_matrix_err_str[err_index++] = space_str[0];
for(aux_index=0; emestr_suffix[aux_index]!='\0'; aux_index++)
  edf_matrix_err_str[err_index++] = emestr_suffix[aux_index];
edf_matrix_err_str[err_index] = '\0';

num_read = fread(diagonal_A_wts, sizeof(float),
                 N_HIDDEN_NEURONS * N_HIDDEN_NEURONS, matrix_data_file);
if(num_read != N_HIDDEN_NEURONS * N_HIDDEN_NEURONS)
  {
    edf_matrix_err_str[type_index] = A_str[0];
    errmess(edf_matrix_err_str);
  }

num_read = fread(diagonal_B_wts, sizeof(float),
                 INPUT_WINDOW_SIZE * INPUT_WINDOW_SIZE * N_HIDDEN_NEURONS,
                 matrix_data_file);
if(num_read != INPUT_WINDOW_SIZE * INPUT_WINDOW_SIZE * N_HIDDEN_NEURONS)
  {
    edf_matrix_err_str[type_index] = B_str[0];
    errmess(edf_matrix_err_str);
  }

num_read = fread(diagonal_C_wts, sizeof(float),
                 N_HIDDEN_NEURONS * N_OUTPUTS, matrix_data_file);
if(num_read != N_HIDDEN_NEURONS * N_OUTPUTS)
  {
    edf_matrix_err_str[type_index] = C_str[0];
    errmess(edf_matrix_err_str);
  }

num_read = fread(diagonal_D_wts, sizeof(float),
                 INPUT_WINDOW_SIZE * INPUT_WINDOW_SIZE * N_OUTPUTS,
                 matrix_data_file);
if(num_read != INPUT_WINDOW_SIZE * INPUT_WINDOW_SIZE * N_OUTPUTS)
  {
    edf_matrix_err_str[type_index] = D_str[0];
    errmess(edf_matrix_err_str);
  }
fclose(matrix_data_file);
}


/*-----------------------------------------------------------------------*/
/*                                                                       */
/* Function to run neural_network edge detectors and store resulting signals */
/*                                                                       */
/*       Modified by KG Heinemann between 29-June and 05-July-1989       */
/*     To implement revisions needed for use with gray scale imagery:    */
/*                                                                       */
/*     The previous neural network structure and calculation procedure   */
/*     are retained, but the individual detectors have been made sensi-  */
/*     tive to the actual DIRECTION OF THE INTENSITY GRADIENT, and not   */
/*      just the "unsigned" orientation.  As a result of this change,    */
/*     each filter generates a strong response only when the edge has    */
/*     a particular orientation AND ONE SPECIFIC SIDE IS BRIGHTER THAN   */
/*     THE OTHER.  For example, a horizontal edge will produce a large   */
/*       signal when the upper region is brighter than the lower one,    */
/*     but NOT in the reverse situation.  However, the original design   */
/*     called for algorithms which would detect edges at the specified   */
/*     orientation without regard to the "direction" of the intensity    */
/*       change.  The desired behavior is recovered by applying two      */
/*     complementary filters for each orientation: one which responds    */
/*     strongly when intensity increases across the edge, and another    */
/*     that is tuned to that same edge with decreasing intensity.  The   */
/*    stronger of these two signals then serves to represent the actual  */
/*    edge strength.  The complementary filters differ from one another  */
/*     only by a 180 degree rotation, because this operation is equiv-   */
/*     alent to reversing the gradient direction.  Hence, if one filter  */
/*    is specified by a given set of connection matrices, we can obtain  */
/*     the complementary filter by rotating those matrices through 180   */
/*     degrees.  In the present implementation, we accomplish the same   */
/*     effect by rotating the input window through 180 degrees.  This    */
/*     operation is accomplished quite easily by simply reversing the    */
/*             order of pixels in the input vector.                      */
/*                                                                       */
/*-----------------------------------------------------------------------*/
```

```
void detect_edges (ix, iy)

/* Image coordinates for upper left corner of input window */
int ix, iy;

{

  int win_row, win_col, aux_index;
  u_char *first_img_pixel, *current_img_pixel;

  /* DEBUG */
  printf("Detect edges called at column %d, row %d.\n", ix, iy);

        /*----------------------------------------------------------*/
        /*                                                          */
        /*  Edge Detection Calculations for the Direct Orientations */
        /*                                                          */
        /*----------------------------------------------------------*/

                        /* Initialization */

  /* Calculate signals transmitted from input neurons for direct orientations
     by normalizing the raw image pixels and applying the sigmoid function   */

        /* Compute actual address of first input pixel
               and initialize pixel pointing index     */
  current_img_pixel = first_img_pixel = image + ((iy*size_x) + ix);

  /* Initialize index for accessing the array of input neuron signals */
  input_index = 0;

  for(win_row=0; win_row<INPUT_WINDOW_SIZE; win_row++)
    {
      for(win_col=0; win_col<INPUT_WINDOW_SIZE; win_col++)

        /* Use simple normalization to emulate rectification
                by the saturated ramp sigmoid function        */
        input_neuron_signal[input_index++] =
          (float)*current_img_pixel++ / (float)(VLT_SIZE-1);

      /* Skip to beginning of input window's next row */
      current_img_pixel+=row_skip_increment;
    }

        /*----------------------------------------------------------*/
        /*  Horizontal/Vertical Edge Detection with Original Filter */
        /*----------------------------------------------------------*/

  compute_hidden_unit_activations
    (INPUT_WINDOW_SIZE * INPUT_WINDOW_SIZE, N_HIDDEN_NEURONS,
     horzvert_A_wts, horzvert_B_wts)

        /* Compute Direct Contributions to Output Layer Activations
           from Input Signals and Store them in Designated Array */

  matrix_vector_product(INPUT_WINDOW_SIZE * INPUT_WINDOW_SIZE, N_OUTPUTS,
                        horzvert_D_wts, input_neuron_signal, B_or_D_fi)

    /* Pass hidden unit activations through the sigmoid rectification */
  for(input_index=0; input_index<N_HIDDEN_NEURONS; input_index++)
    sigrect[input_index] = step_sigmoid(hidden_neuron_signal[input_index]);

  /* Compute Contributions to Output Layer Activations from Hidden Units */
  matrix_vector_product(N_HIDDEN_NEURONS, N_OUTPUTS, horzvert_C_wts,
                        sigrect, output_neuron_signal)

           /* Compute Final Output Activations by Combining
              Contributions from the Input and Hidden Layers
              and Store Results in Edge Detection Feature Array */
  for(input_index=0; input_index<N_OUTPUTS; input_index++)
    {
      output_neuron_signal[input_index] += B_or_D_fi[input_index];
      frwd_feature[ftr_counter++] = output_neuron_signal[input_index];
    }

        /*----------------------------------------------------------*/
```

```
/*      Diagonal Edge Detection with Original Filter      */
/*--------------------------------------------------------*/

compute_hidden_unit_activations
  (INPUT_WINDOW_SIZE * INPUT_WINDOW_SIZE, N_HIDDEN_NEURONS,
   diagonal_A_wts, diagonal_B_wts)

      /* Compute Direct Contributions to Output Layer Activations
         from Input Signals and Store them in Designated Array */

matrix_vector_product(INPUT_WINDOW_SIZE * INPUT_WINDOW_SIZE, N_OUTPUTS,
                      diagonal_D_wts, input_neuron_signal, B_or_D_fi)

  /* Pass hidden unit activations through the sigmoid rectification */
for(input_index=0; input_index<N_HIDDEN_NEURONS; input_index++)
  sigrect[input_index] = step_sigmoid(hidden_neuron_signal[input_index]);

/* Compute Contributions to Output Layer Activations from Hidden Units */
matrix_vector_product(N_HIDDEN_NEURONS, N_OUTPUTS, diagonal_C_wts,
                      sigrect, output_neuron_signal)

          /* Compute Final Output Activations by Combining
             Contributions from the Input and Hidden Layers
            and Store Results in Edge Detection Feature Array */
for(input_index=0; input_index<N_OUTPUTS; input_index++)
  {
    output_neuron_signal[input_index] +=  B_or_D_fi[input_index];
    frwd_feature[ftr_counter++] = output_neuron_signal[input_index];
  }

      /*----------------------------------------------------------*/
      /* Reverse Order of Input Pixels for the Complementary Filters */
      /*----------------------------------------------------------*/

for(input_index=0, aux_index=(INPUT_WINDOW_SIZE*INPUT_WINDOW_SIZE)-1;
    input_index < ((INPUT_WINDOW_SIZE * INPUT_WINDOW_SIZE)+1)/2;
    input_index++, aux_index--)
  {
        scratch_pixel              = input_neuron_signal [input_index];
    input_neuron_signal [input_index] = input_neuron_signal [ aux_index ];
    input_neuron_signal [ aux_index ] =          scratch_pixel;
  }

      /*  Set pointer for Edge Detector Feature Spectrum Back to
          First Location for the Present Set of Direct Orientations */
ftr_counter -= (2 * N_OUTPUTS);

    /*----------------------------------------------------------*/
    /* Horizontal/Vertical Edge Detection with Complementary Filter */
    /*----------------------------------------------------------*/

compute_hidden_unit_activations
  (INPUT_WINDOW_SIZE * INPUT_WINDOW_SIZE, N_HIDDEN_NEURONS,
   horzvert_A_wts, horzvert_B_wts)

      /* Compute Direct Contributions to Output Layer Activations
         from Input Signals and Store them in Designated Array */

matrix_vector_product(INPUT_WINDOW_SIZE * INPUT_WINDOW_SIZE, N_OUTPUTS,
                      horzvert_D_wts, input_neuron_signal, B_or_D_fi)
  /* Pass hidden unit activations through the sigmoid rectification */
 for(input_index=0; input_index<N_HIDDEN_NEURONS; input_index++)
   sigrect[input_index] = step_sigmoid(hidden_neuron_signal[input_index]);

 /* Compute Contributions to Output Layer Activations from Hidden Units */
 matrix_vector_product(N_HIDDEN_NEURONS, N_OUTPUTS, horzvert_C_wts,
                       sigrect, output_neuron_signal)

          /* Compute Final Output Activations by Combining
             Contributions from the Input and Hidden Layers
            and Store Results in Edge Detection Feature Array */
 for(input_index=0; input_index<N_OUTPUTS; input_index++)
   {
     output_neuron_signal[input_index] +=  B_or_D_fi[input_index];
     frwd_feature[ftr_counter] =
       max (frwd_feature [ftr_counter], output_neuron_signal[input_index]);
     ++ftr_counter;
```

```
}

    /*-----------------------------------------------------------*/
    /*     Diagonal Edge Detection with Complementary Filter    */
    /*-----------------------------------------------------------*/

compute_hidden_unit_activations
  (INPUT_WINDOW_SIZE * INPUT_WINDOW_SIZE, N_HIDDEN_NEURONS,
   diagonal_A_wts, diagonal_B_wts)

     /* Compute Direct Contributions to Output Layer Activations
        from Input Signals and Store them in Designated Array */

matrix_vector_product(INPUT_WINDOW_SIZE * INPUT_WINDOW_SIZE, N_OUTPUTS,
                      diagonal_D_wts, input_neuron_signal, B_or_D_fi)

  /* Pass hidden unit activations through the sigmoid rectification */
for(input_index=0; input_index<N_HIDDEN_NEURONS; input_index++)
  sigrect[input_index] = step_sigmoid(hidden_neuron_signal[input_index]);

/* Compute Contributions to Output Layer Activations from Hidden Units */
matrix_vector_product(N_HIDDEN_NEURONS, N_OUTPUTS, diagonal_C_wts,
                      sigrect, output_neuron_signal)

         /* Compute Final Output Activations by Combining
            Contributions from the Input and Hidden Layers
           and Store Results in Edge Detection Feature Array */
for(input_index=0; input_index<N_OUTPUTS; input_index++)
  {
    output_neuron_signal[input_index] +=  B_or_D_fi[input_index];
    frwd_feature[ftr_counter] =
      max (frwd_feature[ftr_counter], output_neuron_signal[input_index]);
    ++ftr_counter;
  }

    /*-----------------------------------------------------------------*/
    /*                                                                 */
    /*  Edge Detection Calculations for the Orthogonal Orientations   */
    /*                                                                 */
    /*-----------------------------------------------------------------*/

                    /* Initialization */

/* Calculate signals transmitted from input neurons for orthogonal orientations
     by normalizing the raw image pixels and applying the sigmoid function   */

 /* Move address for first pixel to end of the input window's first column
               and re-initialize pixel pointing index */
    current_img_pixel =
      (first_img_pixel += offset_for_orthogonal_orientations);

  /* Initialize index for accessing the array of input neuron signals */
  input_index = 0;

  for(win_col=0; win_col<INPUT_WINDOW_SIZE; win_col++)
    {
      /* Skip to end of input window's next column */
      current_img_pixel = first_img_pixel + win_col;

      for(win_row=0; win_row<INPUT_WINDOW_SIZE; win_row++)
        {

          /* Use simple normalization to emulate rectification
                by the saturated ramp sigmoid function        */
          input_neuron_signal[input_index++] =
            (float)*current_img_pixel / (float)(VLT_SIZE-1);

          /* Move back to previous pixel in the same column */
          current_img_pixel -= size_x;
        }
    }

      /*----------------------------------------------------------*/
      /*  Horizontal/Vertical Edge Detection with Original Filter */
      /*----------------------------------------------------------*/
```

```
compute_hidden_unit_activations
  (INPUT_WINDOW_SIZE * INPUT_WINDOW_SIZE, N_HIDDEN_NEURONS,
   horzvert_A_wts, horzvert_B_wts)

       /* Compute Direct Contributions to Output Layer Activations
          from Input Signals and Store them in Designated Array */

matrix_vector_product(INPUT_WINDOW_SIZE * INPUT_WINDOW_SIZE, N_OUTPUTS,
                      horzvert_D_wts, input_neuron_signal, B_or_D_fi)

  /* Pass hidden unit activations through the sigmoid rectification */
for(input_index=0; input_index<N_HIDDEN_NEURONS; input_index++)
  sigrect[input_index] = step_sigmoid(hidden_neuron_signal[input_index]);

/* Compute Contributions to Output Layer Activations from Hidden Units */
matrix_vector_product(N_HIDDEN_NEURONS, N_OUTPUTS, horzvert_C_wts,
                      sigrect, output_neuron_signal)

           /* Compute Final Output Activations by Combining
              Contributions from the Input and Hidden Layers
             and Store Results in Edge Detection Feature Array */
for(input_index=0; input_index<N_OUTPUTS; input_index++)
  {
    output_neuron_signal[input_index] +=  B_or_D_fi[input_index];
    frwd_feature[ftr_counter++] = output_neuron_signal[input_index];
  }


      /*-------------------------------------------------------*/
      /*       Diagonal Edge Detection with Original Filter      */
      /*-------------------------------------------------------*/

compute_hidden_unit_activations
  (INPUT_WINDOW_SIZE * INPUT_WINDOW_SIZE, N_HIDDEN_NEURONS,
   diagonal_A_wts, diagonal_B_wts)

       /* Compute Direct Contributions to Output Layer Activations
          from Input Signals and Store them in Designated Array */

matrix_vector_product(INPUT_WINDOW_SIZE * INPUT_WINDOW_SIZE, N_OUTPUTS,
                      diagonal_D_wts, input_neuron_signal, B_or_D_fi)

  /* Pass hidden unit activations through the sigmoid rectification */
for(input_index=0; input_index<N_HIDDEN_NEURONS; input_index++)
  sigrect[input_index] = step_sigmoid(hidden_neuron_signal[input_index]);

/* Compute Contributions to Output Layer Activations from Hidden Units */
matrix_vector_product(N_HIDDEN_NEURONS, N_OUTPUTS, diagonal_C_wts,
                      sigrect, output_neuron_signal)

           /* Compute Final Output Activations by Combining
              Contributions from the Input and Hidden Layers
             and Store Results in Edge Detection Feature Array */
for(input_index=0; input_index<N_OUTPUTS; input_index++)
  {
    output_neuron_signal[input_index] +=  B_or_D_fi[input_index];
    frwd_feature[ftr_counter++] = output_neuron_signal[input_index];
  }

      /*-----------------------------------------------------------*/
      /* Reverse Order of Input Pixels for the Complementary Filters */
      /*-----------------------------------------------------------*/

for(input_index=0, aux_index=(INPUT_WINDOW_SIZE*INPUT_WINDOW_SIZE)-1;
    input_index < ((INPUT_WINDOW_SIZE * INPUT_WINDOW_SIZE)+1)/2;
    input_index++, aux_index--)
  {
            scratch_pixel             = input_neuron_signal [input_index];
    input_neuron_signal [input_index] = input_neuron_signal [ aux_index ];
    input_neuron_signal [ aux_index ] =        scratch_pixel;
  }

      /*  Set pointer for Edge Detector Feature Spectrum Back to
          First Location for the Present Set of Direct Orientations */
ftr_counter -= (2 * N_OUTPUTS);
```

```
        /*-------------------------------------------------------------*/
        /* Horizontal/Vertical Edge Detection with Complementary Filter */
        /*-------------------------------------------------------------*/

    compute_hidden_unit_activations
      (INPUT_WINDOW_SIZE * INPUT_WINDOW_SIZE, N_HIDDEN_NEURONS,
       horzvert_A_wts, horzvert_B_wts)

           /* Compute Direct Contributions to Output Layer Activations
           from Input Signals and Store them in Designated Array */

  matrix_vector_product(INPUT_WINDOW_SIZE * INPUT_WINDOW_SIZE, N_OUTPUTS,
                        horzvert_D_wts, input_neuron_signal, B_or_D_fi)

    /* Pass hidden unit activations through the sigmoid rectification */
  for(input_index=0; input_index<N_HIDDEN_NEURONS; input_index++)
    sigrect[input_index] = step_sigmoid(hidden_neuron_signal[input_index]);

  /* Compute Contributions to Output Layer Activations from Hidden Units */
  matrix_vector_product(N_HIDDEN_NEURONS, N_OUTPUTS, horzvert_C_wts,
                        sigrect, output_neuron_signal)

            /* Compute Final Output Activations by Combining
               Contributions from the Input and Hidden Layers
              and Store Results in Edge Detection Feature Array */
  for(input_index=0; input_index<N_OUTPUTS; input_index++)
    {
      output_neuron_signal[input_index] += B_or_D_fi[input_index];
      frwd_feature[ftr_counter] =
        max (frwd_feature[ftr_counter], output_neuron_signal[input_index]);
      ++ftr_counter;
    }

        /*-------------------------------------------------------*/
        /*     Diagonal Edge Detection with Complementary Filter   */
        /*-------------------------------------------------------*/

  compute_hidden_unit_activations
    (INPUT_WINDOW_SIZE * INPUT_WINDOW_SIZE, N_HIDDEN_NEURONS,
     diagonal_A_wts, diagonal_B_wts)

         /* Compute Direct Contributions to Output Layer Activations
            from Input Signals and Store them in Designated Array */

  matrix_vector_product(INPUT_WINDOW_SIZE * INPUT_WINDOW_SIZE, N_OUTPUTS,
                        diagonal_D_wts, input_neuron_signal, B_or_D_fi)

    /* Pass hidden unit activations through the sigmoid rectification */
  for(input_index=0; input_index<N_HIDDEN_NEURONS; input_index++)
    sigrect[input_index] = step_sigmoid(hidden_neuron_signal[input_index]);

  /* Compute Contributions to Output Layer Activations from Hidden Units */
  matrix_vector_product(N_HIDDEN_NEURONS, N_OUTPUTS, diagonal_C_wts,
                        sigrect, output_neuron_signal)

            /* Compute Final Output Activations by Combining
               Contributions from the Input and Hidden Layers
              and Store Results in Edge Detection Feature Array */
  for(input_index=0; input_index<N_OUTPUTS; input_index++)
    {
      output_neuron_signal[input_index] += B_or_D_fi[input_index];
      frwd_feature[ftr_counter] =
        max (frwd_feature[ftr_counter], output_neuron_signal[input_index]);
      ++ftr_counter;
    }
}

void display_edf_results()
{
  int i, j, ibin, edf_img_base_ptr, edf_img_offset, new_pix,
      nfill, fill_start, fill_end, nbins, bin_length, bindex;
  float scale_fac, edfmax, edfmin, slope_for_bin, plot_y, last_y;

  /* Compute bin length for scaling plot along the abscissa */
  nbins = ftr_counter - EDF_SPECTRUM_OFFSET - 1;
  bin_length = max ((EDF_DISPLAY_WIDTH / nbins), 1);
```

```
/* Find maximum and minimum edge detector output responses */
edfmax = 0;
edfmin = pow (2.0, 32);
for(i=EDF_SPECTRUM_OFFSET; i<ftr_counter; i++)
  {
    if(frwd_feature[i]>edfmax)
      edfmax=frwd_feature[i];
    if(frwd_feature[i]<edfmin)
      edfmin=frwd_feature[i];
  }

if(edfmax != edfmin)
  scale_fac = (float)HST_HEIGHT / (edfmax - edfmin);
else
  scale_fac = 0.0;

/* Clear edge detector results image */

for(i=0; i<N_EDF_PLOT_PIXELS; i++)
  edf_image[i]=0;

             /* Generate new edge detector results image */

edf_img_base_ptr = PLOT_BORDER_WIDTH * hist_height;
last_y =0.0;

/* Calculate and fill in plot points within the designated bins */
for (ibin=0; ibin<nbins; ibin++)      /* Loop over designated bins */
  {
    i = ibin + EDF_SPECTRUM_OFFSET;

    /* Compute slope for linear interpolation within bin */
    slope_for_bin =
      (float)(frwd_feature[i+1] - frwd_feature[i]) / (float)bin_length;

    /* Loop over points in the current bin */
    for(bindex=0; bindex<bin_length; bindex++)
      {

    /* Compute current display position and fill it in */

        /* y = Ax + B */
        plot_y =
          (slope_for_bin * (float)bindex) + (frwd_feature[i] - edfmin);
        edf_img_offset =
          HST_HEIGHT - (int)(scale_fac * plot_y);
        edf_image[(new_pix=edf_img_base_ptr+edf_img_offset)]=3;

  /* Fill in current column from current y-value to the preceeding one */
        nfill = (int)(scale_fac * (last_y - plot_y));
        if(nfill)
          {
  /* Define upper limit of the intensity interval to be stretched
        by finding the point where the cumulative histogram count
             first exceeds 99.25% of the total image pixels          */

  clip_thresh = (int)(0.0075 * (float)(size_x * size_y));
  for (upperlim=(VLT_SIZE-1), cum_sum=0;
        (upperlim>-1) && (cum_sum<clip_thresh);
        upperlim--)
    cum_sum += IRP_hist_data[upperlim];
  ++upperlim;

  /* Compute scale factor for linear stretching of intensity values */
  scale_fac = (float)VLT_SIZE / (float)(upperlim - lowerlim + 1);

  if (scale_fac>1.0)
    {

    /* Allocate temporary memory block for storing modified image */
      new_image = (float *)calloc(size_x * size_y, sizeof(float));

      /* Compute sum of intensity values in a 3 x 3 window
           centered on the pixel which is to be modified,
      clipping regions window which fall outside image borders */
```

```
for (win_row=first_row=0; win_row<size_y; win_row++)
  {
    last_row = min (win_row+2, size_y);
    for (win_col=first_col=0; win_col<size_x; win_col++)
      {
        last_col = min (win_col+2, size_x);
        cum_sum = 0.0;
        denom = 0.0;

        for (irow=first_row; irow<last_row; irow++)
          {
            index = (irow * size_x) + first_col;
            for (icol=first_col; icol<last_col; icol++)
              {
                cum_sum += image[index++];
                denom += 1.0;
              }
          }

    /* Array index of pixel which is to be modified */
        index = (win_row * size_x) + win_col;

  /* Compute mean intensity for the 3 x 3 window and combine
     results with the original intensity value in a 1:3 ratio  */

        new_image [index] = (float)cum_sum / denom;
        new_image [index] += (float)(3 * image[index]);
        new_image [index] = new_image[index] / 4.0;

        first_col = win_col;
      }
    first_row = win_row;
  }

/* Calculate values for new image by applying histogram based

            fill_start = min(new_pix, (new_pix - nfill));
            fill_end   = max(new_pix, (new_pix - nfill));
            for(j=fill_start; j<fill_end; j++)
              edf_image[j]=3;
          }

        last_y = plot_y;
        edf_img_base_ptr+=hist_height;
      }
  }

/* Check whether designated bins occupy all available plot columns;
   If not, compute an additional point to represent end of last bin */
if((nbins*bin_length)<EDF_PLOT_WIDTH)
  {
    plot_y = frwd_feature[ftr_counter-1] - edfmin;
    edf_img_offset =  HST_HEIGHT - (int)(scale_fac * plot_y);
    edf_image[(new_pix=edf_img_base_ptr+edf_img_offset)]=3;
    nfill = (int)(scale_fac * (last_y - plot_y));
    if(nfill)
      {
        fill_start = min(new_pix, (new_pix - nfill));
        fill_end   = max(new_pix, (new_pix - nfill));
        for(j=fill_start; j<fill_end; j++)
          edf_image[j]=3;
      }
  }

edf_img_offset=0;
pw_batch_on(edf_pw);
for(i=0; i<EDF_PLOT_WIDTH; i++)
  {
    for (edf_img_base_ptr=24; edf_img_base_ptr<HST_WIN_HEIGHT;
         ++edf_img_base_ptr)
      {
        pw_rop(edf_pw, i, edf_img_base_ptr, 1, 1,
               PIX_SRC | PIX_COLOR(edf_image[edf_img_offset]),
               (Pixrect *)0, 0, 0);
        ++edf_img_offset;
      }
```

```
  }
 pw_batch_off(edf_pw);
}

void spiral_map()

/*  Modified by KG Heinemann on 03 - 04 October 1989 to add mechanism for
   communicating validity of edge detector results to other "cellview" modules
                    (the "valid_V1_flag")                                  */

{
 int
                /* Image Coordinate Corresponding to
                      First Column of Input Windows
                for a Given Cycle of the Scan Sequence*/
    first_x,
                /* Image Coordinate Corresponding to
                       First Row of Input Windows
                for a Given Cycle of the Scan Sequence*/
    first_y,
                /* Image Coordinate Corresponding to
                      Last Column of Input Windows
                for a Given Cycle of the Scan Sequence*/
    last_x,
                /* Image Coordinate Corresponding to
                       Last Row of Input Windows
                for a Given Cycle of the Scan Sequence*/
    last_y,
                /* Horizontal and Vertical Image Coordinates
                   Corresponding to Active Position in Scan */
    ix_index, iy_index;

  FILE *specdata_file, *fopen();

        /* Generate and Plot new Edge Detector Spectrum
           Only if the Current Information is Not Valid */

  if (!valid_V1_flag)
    {
      /* Initialize count of individual edge detector features */
      ftr_counter=EDF_SPECTRUM_OFFSET;

      /* Initialize parameters for transferring input data from
         the actual image to an input window array            */
      row_skip_increment = max(0, (size_x - INPUT_WINDOW_SIZE));
      offset_for_orthogonal_orientations = size_x * (INPUT_WINDOW_SIZE-1);

      /* Set Limits for Initial Cycle of the Scan Sequence */
      first_x = first_y = 0;

      last_x = INPUT_WINDOW_SIZE * ((size_x / INPUT_WINDOW_SIZE) - 1);
      last_y = INPUT_WINDOW_SIZE * ((size_y / INPUT_WINDOW_SIZE) - 1);

      /* Loop over separate cycles of the spiral scan pattern */
      while (first_x <= last_x && first_y <= last_y)
        {
          for (ix_index=first_x; ix_index<=last_x;
                ix_index += INPUT_WINDOW_SIZE)
            detect_edges (ix_index, first_y);

          first_y += INPUT_WINDOW_SIZE;
          for (iy_index=first_y; iy_index<=last_y;
                iy_index += INPUT_WINDOW_SIZE)
            detect_edges (last_x, iy_index);

          last_x -= INPUT_WINDOW_SIZE;
          for (ix_index=last_x; ix_index>first_x;
                ix_index -= INPUT_WINDOW_SIZE)
            detect_edges (ix_index, last_y);

          for (iy_index=last_y; iy_index>=first_y;
                iy_index -= INPUT_WINDOW_SIZE)
            detect_edges (first_x, iy_index);

          first_x += INPUT_WINDOW_SIZE;
          last_y  -= INPUT_WINDOW_SIZE;
        }
```

```
      /* DEBUG */
      printf("\nSpiral map has generated %d points for the spectrum.\n",
             (ftr_counter-EDF_SPECTRUM_OFFSET));

     /* Set Flag to Indicate that Edge Detector Spectrum is Now Valid */
     valid_V1_flag = 1;

     /* DEBUG */
/*
     specdata_file = fopen("spectrum.dat", "w");
     if(specdata_file==NULL)
       errmess("Error opening spectrum data file!");
     else
       {
         printf
           ("Writing edge feature spectrum data to file \"spectrum.dat\".");
         for(ix_index=EDF_SPECTRUM_OFFSET; ix_index<ftr_counter; ++ix_index)
           fprintf(specdata_file, "%9.3f\n", frwd_feature[ix_index]);
       }
     fclose(specdata_file);
*/
     display_edf_results();
   }
}

     /* IRP_visar2.c         Printed on 18-December-1989 */

/*
                Code to implement neural network algorithm for
          assessing positional offsets within a field of view (V2)
                               for IRP
*/

   /* Originally coded by KG Heinemann from 16-June-1989 to 07-August-1989 */

   /*   Modified by KG Heinemann on 03 - 04 October 1989 to add mechanism
      for communicating validity of V2 results to other "cellview" modules
                      (the "valid_V2_flag")                                */

#include <stdio.h>
#include <string.h>
#include <math.h>

#include <suntool/sunview.h>
#include <suntool/canvas.h>
#include <suntool/panel.h>

#include "image_io.h"
#include "cellview.h"
#include "netparam.h"

/* Second Dimension of Input Window for Reduce Network in V2 */
#define V2AUX_WINDOW_SIZE   3

#if (V2AUX_WINDOW_SIZE > INPUT_WINDOW_SIZE)
#define RSKP_INC 0
#else
#define RSKP_INC (INPUT_WINDOW_SIZE-V2AUX_WINDOW_SIZE)
#endif

        /* Flag to Indicate Whether Centering Signal (V2)
              Values are Valid for the Current Image        */
u_char valid_V2_flag;

/* Pointer to memory region for compressed image */
ACTIVATION_DATA_TYPE *V2_hidden_layer=NULL;

/* Image compression factors (linear dimensions of the averaging window) */
int x_compression_factor, y_compression_factor;

char too_small_img_str[92];

char *horz_str  = "Horizontal";
char *vert_str  = "Vertical";
char *lstr1     = " size of the ";
```

```
char *inpt_str  = "input";
char *lstr2     = " image (";
char *lstr3     = ") is too small for the ";
char *offs_str  = "offset detector's";
char *lstr4     = " input window.";

char *insufmem_str = "V2_average: insufficient memory available for V2 image.";

/* Strengths for connections between the hidden units */
float V2_A_wts [N_HIDDEN_NEURONS * N_HIDDEN_NEURONS];

/* Strengths for connections between input units and hidden units */
float V2_B_wts [INPUT_WINDOW_SIZE * V2AUX_WINDOW_SIZE * N_HIDDEN_NEURONS];

/* Strengths for connections between hidden units and output units */
float V2_C_wts [N_HIDDEN_NEURONS * N_OUTPUTS];

/* Strengths for connections between input units and output units */
float V2_D_wts [INPUT_WINDOW_SIZE * V2AUX_WINDOW_SIZE * N_OUTPUTS];


/*------------------------------------------------------------------------*/
/*                                                                        */
/* Utility routine to read in pre-established V2 connection strength values */
/*                        from file on disk                               */
/*                                                                        */
/*------------------------------------------------------------------------*/

/*          Adapted from the "get_edf_matrix_elements" routine
               by KG Heinemann on 31-July - 01-August 1989              */

char *V2_matrix_err_str =
  "\nError reading coefficients for V2's   matrix!\n\n";

void get_V2_matrix_elements()

{
  FILE *matrix_data_file, *fopen();
  int num_read, err_index, aux_index, type_index=37;

  /* Attempt to open matrix coefficient data file */
  matrix_data_file = fopen("V2_matrices.bin", "r");
  if(matrix_data_file==NULL)
    errmess("\nError opening V2's matrix coefficient file!\n\n");

  num_read = fread (V2_A_wts, sizeof(float),
                    N_HIDDEN_NEURONS * N_HIDDEN_NEURONS, matrix_data_file);
  if(num_read != N_HIDDEN_NEURONS * N_HIDDEN_NEURONS)
    {
      V2_matrix_err_str[type_index] = A_str[0];
      errmess(V2_matrix_err_str);
    }

  num_read = fread(V2_B_wts, sizeof(float),
                   INPUT_WINDOW_SIZE * V2AUX_WINDOW_SIZE * N_HIDDEN_NEURONS,
                   matrix_data_file);
  if(num_read != INPUT_WINDOW_SIZE * V2AUX_WINDOW_SIZE * N_HIDDEN_NEURONS)
    {
      V2_matrix_err_str[type_index] = B_str[0];
      errmess(V2_matrix_err_str);
    }

  num_read = fread
    (V2_C_wts, sizeof(float), N_HIDDEN_NEURONS * N_OUTPUTS, matrix_data_file);
  if(num_read != N_HIDDEN_NEURONS * N_OUTPUTS)
    {
      V2_matrix_err_str[type_index] = C_str[0];
      errmess(V2_matrix_err_str);
    }

  num_read = fread(V2_D_wts, sizeof(float),
                   INPUT_WINDOW_SIZE * V2AUX_WINDOW_SIZE * N_OUTPUTS,
                   matrix_data_file);
  if(num_read != INPUT_WINDOW_SIZE * V2AUX_WINDOW_SIZE * N_OUTPUTS)
    {
      V2_matrix_err_str[type_index] = D_str[0];
      errmess(V2_matrix_err_str);
    }
```

```
  fclose(matrix_data_file);
}

/* ---------------------------------------------------------------------- */

void V2_average()
{
  int scan_row, scan_col, irow, icol, V2_ptr;  /* Indices */

  int pixsum;   /* Sum of integer pixel values within a given window */

        /* Divisor to compute window average from "pixsum"
           and normalize intensities at the same time */
  ACTIVATION_DATA_TYPE normal_factor;

  /* Pixel position corresponding to beginning of current row in loop */
  int row_begn;

  /* Number of image pixels to skip when the averaging window moves
       between subsequent row positions of its scanning pattern        */
  int srb_skip_increment;

  /* Number of image pixels to skip when moving from the end of one row
        in the averaging window to the beginning of the next one       */
  int row_skip_increment;

  /* Compute dimensions of the averaging window (image compression factors)
     and use the results to determine whether the input window is too small
                      for the offset detector */
  x_compression_factor = size_x / INPUT_WINDOW_SIZE;
  y_compression_factor = size_y / INPUT_WINDOW_SIZE;

  if (x_compression_factor>0 && y_compression_factor>0)
    {
     if (V2_hidden_layer == NULL)  /* Allocate memory for compressed image */
       {
        V2_hidden_layer = (ACTIVATION_DATA_TYPE *)calloc
          (INPUT_WINDOW_SIZE * INPUT_WINDOW_SIZE,
           sizeof(ACTIVATION_DATA_TYPE));
        if (V2_hidden_layer == NULL)
          if (!batch_flg) message(insufmem_str);
          else err_str = insufmem_str;
       }

     /* Compute compressed image only if storage has been allocated */
     if (V2_hidden_layer != NULL)
       {

        /* Set divisor for averaging to product of the window size
              and the normalizing factor for conversion between
                     integer and real pixel values                  */
        normal_factor = (ACTIVATION_DATA_TYPE)
          ((VLT_SIZE-1) * x_compression_factor * y_compression_factor);

        /* Compute pixel increment for moving between rows within a window */
        row_skip_increment = size_x - x_compression_factor;

        /* Compute pixel increment for moving the averaging window
           between subsequent row positions of its scanning patter */
        srb_skip_increment = size_x * y_compression_factor;

        /* Loops to scan the averaging process over the entire image */

        V2_ptr=0;
        for (scan_row=0, row_begn=0; scan_row<size_y;
             scan_row+=y_compression_factor, row_begn+=srb_skip_increment)
          for(scan_col=0; scan_col<size_x; scan_col+=x_compression_factor)
            {
              input_index = row_begn + scan_col;
              pixsum = 0;

              for (irow=0; irow<y_compression_factor; irow++)
                {
                  for (icol=0; icol<x_compression_factor; icol++)
                    pixsum += image[input_index++];
```

```
              input_index += row_skip_increment;
            }
          V2_hidden_layer[V2_ptr++] = (float)pixsum / normal_factor;
        }
      }
    }
}

/* Routine to generate positional offset signals from the compressed image */

void detect_offset()
{
  int scan_row, scan_col, V2_ptr, V2_base_ptr;

  if (!valid_V2_flag)
    {
      V2_average();              /* Generate the compressed image */

      /* Skip remaining computations if memory allocation error
           occurred while generating the compressed image      */
      if (V2_hidden_layer != NULL)
        {

          if (x_compression_factor < 1)
            {
              too_small_img_str[0] = '\0';
              strcat  (too_small_img_str, horz_str,   10   );
              strcat  (too_small_img_str, lstr1,      13   );
              strcat  (too_small_img_str, inpt_str,   10   );
              strcat  (too_small_img_str, lstr2,       8   );
              sprintf (too_small_img_str+41, "%2d", size_x );
              strcat  (too_small_img_str, lstr3,      24   );
              strcat  (too_small_img_str, offs_str,   16   );
              strcat  (too_small_img_str, lstr4,      14   );
              if (!batch_flg) message (too_small_img_str);
              else err_str = too_small_img_str;
            }
          else
            {
              if (y_compression_factor < 1)
                {
                  too_small_img_str[0] = '\0';
                  strcat  (too_small_img_str, vert_str,    8   );
                  strcat  (too_small_img_str, lstr1;      13   );
                  strcat  (too_small_img_str, inpt_str,   10   );
                  strcat  (too_small_img_str, lstr2,       8   );
                  sprintf (too_small_img_str+39, "%2d", size_y );
                  strcat  (too_small_img_str, lstr3,      24   );
                  strcat  (too_small_img_str, offs_str,   16   );
                  strcat  (too_small_img_str, lstr4,      14   );
                  if (!batch_flg) message (too_small_img_str);
                  else err_str = too_small_img_str;
                }

              else

                {
                  ftr_counter = V2_SPECTRUM_OFFSET;

        /*------- ---------------------------------------------*/
        /*                                                      */
        /*  Offset Signal Calculations for the Northerly Direction */
        /*                                                      */
        /*-----------------------------------------------------*/

            /* Initialization - Pack Data from Compressed Image
                  into the 7 x 3 Neural Network Input Array      */

                  input_index=0;
                  for (scan_col=INPUT_WINDOW_SIZE; scan_col>0; --scan_col)
                    {
                      V2_ptr = scan_col - 1;
                      for (scan_row=0; scan_row<V2AUX_WINDOW_SIZE; ++scan_row)
                        {
                          input_neuron_signal[input_index++] =
                            V2_hidden_layer[V2_ptr];
                          V2_ptr += INPUT_WINDOW_SIZE;
                        }
```

```
}

/* Actual Calculation for Raw Sub-Image */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE,
   N_OUTPUTS, V2_D_wts, input_neuron_signal, B_or_D_fi)

/* Pass hidden unit activations through the sigmoid rectification */
for(input_index=0; input_index<N_HIDDEN_NEURONS;
      input_index++)
    sigrect[input_index] =
      step_sigmoid(hidden_neuron_signal[input_index]);

/* Compute Contributions to Output Layer Activations from Hidden Units */
matrix_vector_product(N_HIDDEN_NEURONS, N_OUTPUTS, V2_C_wts,
                      sigrect, output_neuron_signal)

/* Compute Final Output Activations by Combining
   Contributions from the Input and Hidden Layers
   and Store Results in Edge Detection Feature Array */
for(input_index=0; input_index<N_OUTPUTS; input_index++)
  {
    output_neuron_signal[input_index] +=
      B_or_D_fi[input_index];
    frwd_feature[ftr_counter] =
      output_neuron_signal[input_index];
  }

/* Compute Complement of the Input Sub-Image */
for (input_index=0;
     input_index < (INPUT_WINDOW_SIZE * V2AUX_WINDOW_SIZE);
     ++input_index)
  input_neuron_signal[input_index] =
    1.0 - input_neuron_signal[input_index];

/* Repeat Offset Signal Calculation Using
   the Complemented Sub-Image as Input   */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE, N_OUTPUTS,
   V2_D_wts, input_neuron_signal, B_or_D_fi)

/* Pass hidden unit activations through the sigmoid rectification */
for(input_index=0; input_index<N_HIDDEN_NEURONS;
    input_index++)
  sigrect[input_index] =
    step_sigmoid(hidden_neuron_signal[input_index]);

/* Compute Contributions to Output Layer Activations from Hidden Units */
matrix_vector_product(N_HIDDEN_NEURONS, N_OUTPUTS, V2_C_wts,
                      sigrect, output_neuron_signal)

/* Compute Final Output Activations by Combining
   Contributions from the Input and Hidden Layers
   and Store Results in Edge Detection Feature Array */
for(input_index=0; input_index<N_OUTPUTS; input_index++)
  {
    output_neuron_signal[input_index] +=
      B_or_D_fi[input_index];
    frwd_feature[ftr_counter] =
      max (frwd_feature[ftr_counter],
           output_neuron_signal[input_index]);
```

```
for (input_index=0;
     input_index < (INPUT_WINDOW_SIZE * V2AUX_WINDOW_SIZE);
     ++input_index)
  input_neuron_signal[input_index] =
    1.0 - input_neuron_signal[input_index];

/* Repeat Offset Signal Calculation Using
   the Complemented Sub-Image as Input   */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE, N_OUTPUTS,
   V2_D_wts, input_neuron_signal, B_or_D_fi)

/* Pass hidden unit activations through the sigmoid rectification */
for(input_index=0; input_index<N_HIDDEN_NEURONS;
    input_index++)
  sigrect[input_index] =
    step_sigmoid(hidden_neuron_signal[input_index]);

/* Compute Contributions to Output Layer Activations from Hidden Units */
matrix_vector_product(N_HIDDEN_NEURONS, N_OUTPUTS, V2_C_wts,
                      sigrect, output_neuron_signal)

/* Compute Final Output Activations by Combining
   Contributions from the Input and Hidden Layers
  and Store Results in Edge Detection Feature Array */
for(input_index=0; input_index<N_OUTPUTS; input_index++)
  {
    output_neuron_signal[input_index] +=
      B_or_D_fi[input_index];
    frwd_feature[ftr_counter] =
      max (frwd_feature[ftr_counter],
           output_neuron_signal[input_index]);
    ++ftr_counter;
  }

/*-------------------------------------------------------*/
/*                                                       */
/*  Offset Signal Calculations for the Easterly Direction */
/*                                                       */
/*-------------------------------------------------------*/

/* Initialization - Pack Data from Compressed Image
     into the 7 x 3 Neural Network Input Array     */

input_index=0;
V2_ptr = (INPUT_WINDOW_SIZE * INPUT_WINDOW_SIZE) - 1;
for (scan_row=0; scan_row<INPUT_WINDOW_SIZE; ++scan_row)
  {
    for (scan_col=0; scan_col<V2AUX_WINDOW_SIZE; ++scan_col)
      input_neuron_signal[input_index++] =
        V2_hidden_layer[V2_ptr--];
    V2_ptr -= RSKP_INC;

  }

/* Actual Calculation for Raw Sub-Image */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE, N_OUTPUTS,
   V2_D_wts, input_neuron_signal, B_or_D_fi)
```

```
/* Pass hidden unit activations through the sigmoid rectification */
        for(input_index=0; input_index<N_HIDDEN_NEURONS;
            input_index++)
          sigrect[input_index] =
            step_sigmoid(hidden_neuron_signal[input_index]);

/* Compute Contributions to Output Layer Activations from Hidden Units */
        matrix_vector_product(N_HIDDEN_NEURONS, N_OUTPUTS, V2_C_wts,
                              sigrect, output_neuron_signal)

    /* Compute Final Output Activations by Combining
       Contributions from the Input and Hidden Layers
      and Store Results in Edge Detection Feature Array */
        for(input_index=0; input_index<N_OUTPUTS; input_index++)
          {
            output_neuron_signal[input_index] +=
              B_or_D_fi[input_index];
            frwd_feature[ftr_counter] =
              output_neuron_signal[input_index];
          }

       /* Compute Complement of the Input Sub-Image */
        for (input_index=0;
             input_index < (INPUT_WINDOW_SIZE * V2AUX_WINDOW_SIZE);
             ++input_index)
          input_neuron_signal[input_index] =
            1.0 - input_neuron_signal[input_index];

       /* Repeat Offset Signal Calculation Using
          the Complemented Sub-Image as Input   */

        compute_hidden_unit_activations
          (INPUT_WINDOW_SIZE * V2AUX_WINDOW_SIZE, N_HIDDEN_NEURONS,
           V2_A_wts, V2_B_wts)

  /* Compute Direct Contributions to Output Layer Activations
     from Input Signals and Store them in Designated Array */

        matrix_vector_product
          (INPUT_WINDOW_SIZE * V2AUX_WINDOW_SIZE, N_OUTPUTS,
           V2_D_wts, input_neuron_signal, B_or_D_fi)

/* Pass hidden unit activations through the sigmoid rectification */
        for(input_index=0; input_index<N_HIDDEN_NEURONS;
            input_index++)

          sigrect[input_index] =
            step_sigmoid(hidden_neuron_signal[input_index]);

/* Compute Contributions to Output Layer Activations from Hidden Units */
        matrix_vector_product(N_HIDDEN_NEURONS, N_OUTPUTS, V2_C_wts,
                              sigrect, output_neuron_signal)

    /* Compute Final Output Activations by Combining
       Contributions from the Input and Hidden Layers
      and Store Results in Edge Detection Feature Array */
        for(input_index=0; input_index<N_OUTPUTS; input_index++)
          {
            output_neuron_signal[input_index] +=
              B_or_D_fi[input_index];
            frwd_feature[ftr_counter] =
              max (frwd_feature[ftr_counter],
                   output_neuron_signal[input_index]);
            ++ftr_counter;
          }

  /*-------------------------------------------------------*/
  /*                                                       */
  /*  Offset Signal Calculations for the Westerly Direction */
  /*                                                       */
  /*-------------------------------------------------------*/

    /* Initialization - Pack Data from Compressed Image
         into the 7 x 3 Neural Network Input Array      */
```

```
input_index = V2_ptr = 0;
for (scan_row=0; scan_row<INPUT_WINDOW_SIZE; ++scan_row)
  {
    for (scan_col=0; scan_col<V2AUX_WINDOW_SIZE; ++scan_col)
      input_neuron_signal[input_index++] =
        V2_hidden_layer[V2_ptr++];
    V2_ptr += RSKP_INC;
  }

/* Actual Calculation for Raw Sub-Image */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE, N_OUTPUTS,
   V2_D_wts, input_neuron_signal, B_or_D_fi)

/* Pass hidden unit activations through the sigmoid rectification */
for(input_index=0; input_index<N_HIDDEN_NEURONS;
    input_index++)
  sigrect[input_index] =
    step_sigmoid(hidden_neuron_signal[input_index]);

/* Compute Contributions to Output Layer Activations from Hidden Units */
matrix_vector_product(N_HIDDEN_NEURONS, N_OUTPUTS, V2_C_wts,
                      sigrect, output_neuron_signal)

/* Compute Final Output Activations by Combining
   Contributions from the Input and Hidden Layers
  and Store Results in Edge Detection Feature Array */
for(input_index=0; input_index<N_OUTPUTS; input_index++)
  {
    output_neuron_signal[input_index] +=
      B_or_D_fi[input_index];
    frwd_feature[ftr_counter] =
      output_neuron_signal[input_index];
  }

/* Compute Complement of the Input Sub-Image */
for (input_index=0;
     input_index < (INPUT_WINDOW_SIZE * V2AUX_WINDOW_SIZE);
     ++input_index)
  input_neuron_signal[input_index] =
    1.0 - input_neuron_signal[input_index];

/* Repeat Offset Signal Calculation Using
   the Complemented Sub-Image as Input   */

compute_hidden_unit_activations
  (INPUT_WINDOW_SIZE * V2AUX_WINDOW_SIZE, N_HIDDEN_NEURONS,
   V2_A_wts, V2_B_wts)

/* Compute Direct Contributions to Output Layer Activations
   from Input Signals and Store them in Designated Array */

matrix_vector_product
  (INPUT_WINDOW_SIZE * V2AUX_WINDOW_SIZE, N_OUTPUTS,
   V2_D_wts, input_neuron_signal, B_or_D_fi)

/* Pass hidden unit activations through the sigmoid rectification */
for(input_index=0; input_index<N_HIDDEN_NEURONS;
    input_index++)
  sigrect[input_index] =
    step_sigmoid(hidden_neuron_signal[input_index]);

/* Compute Contributions to Output Layer Activations from Hidden Units */
matrix_vector_product(N_HIDDEN_NEURONS, N_OUTPUTS, V2_C_wts,
                      sigrect, output_neuron_signal)

/* Compute Final Output Activations by Combining
   Contributions from the Input and Hidden Layers
```

```
            and Store Results in Edge Detection Feature Array */
               for(input_index=0; input_index<N_OUTPUTS; input_index++)
                 {
                   output_neuron_signal[input_index] +=
                     B_or_D_fi[input_index];
                   frwd_feature[ftr_counter] =
                     max (frwd_feature[ftr_counter],
                          output_neuron_signal[input_index]);
                   ++ftr_counter;
                 }

      /* Set Flag to Indicate that Offset Detection Signals Are Now Valid */
               valid_V2_flag = 1;
             }
         }

      }
    }
 }
       /* ART2.c                  Printed on 18-December-1989 */

#include <stdio.h>
#include <math.h>

#define MXITR      3
#define MXVAL    255
#define NONE      -1
#define NDCHG     -2
#define RESET     -3


/* Specify "C" data type for representation of activation levels
             in neural network edge detection algorithm          */
#include "activation.h"

 /*     Header file to make Long Term Memory trace information
      and ART 2 result descriptors available to outside programs */
#include "LTM.h"

#define max(a,b) (((a)>(b))?(a):(b))
#define min(a,b) (((a)<(b))?(a):(b))
#define fth(a)   (((a)>theta)?(a):0.0)
#define sqr(a)   ((a)*(a))

#define calloc2D(ny,nx,type) \
  (type **)kalloc2D(ny,nx,sizeof(type),sizeof(type *))

#define calloc1D(nx,type) (type *)calloc(nx,sizeof(type))

/* Number of output categories (F2 nodes) for the ART2 classifier */
int     nF2;

int     MXPAS;
float   MXERR,  step;

float   a, b, c, d, rho, theta, alpha;  /* ART2 control parameters */

float   **ztd, **zbu,
        *p, *q, *r, *u, *v, *w, *x, *y, **z;

float   P, R, V, W;

int     *Npatlst;

int     Nactv, Jactv, Jpntr, *Jnext;

int     ARTreset, ndchg;

/* Error messages for "Ordinary Differential Equation Integration" Routines */

char *odeerr_1 = "ART2: Step size too small in ODEINT.";
char *odeerr_2 = "ART2: Too many steps in routine ODEINT.";
char *odeerr_3 = "ART2: Step size too small in routine RKQC.";

/*-----------------------------------------------------------------------*/

void ART_start (nF1)

        /* Allocate memory for ART2 computation information
```

```
                 and read in parameters from file on disk  */

int     nF1;            /* Number of nodes in an input pattern */

{
  FILE *ART2_parameter_file, *fopen();

  void  ode_alloc();
  char  *calloc();
  char  **kalloc2D();
  int   i, j;
  float const;
  char dumchar;

  /* Attempt to open data file containing operational parameters for ART2 */
  ART2_parameter_file = fopen("ART2.par", "r");
  if(ART2_parameter_file==NULL)
    errmess("\nUnable to open ART 2 parameter file.\n\n");
  fscanf(ART2_parameter_file, "%d%*[^\n]*%c", &nF2);
  fscanf(ART2_parameter_file, "%f%*[^\n]*%c", &a);
  fscanf(ART2_parameter_file, "%f%*[^\n]*%c", &b);
  fscanf(ART2_parameter_file, "%f%*[^\n]*%c", &c);
  fscanf(ART2_parameter_file, "%f%*[^\n]*%c", &d);
  fscanf(ART2_parameter_file, "%f%*[^\n]*%c", &rho);
  fscanf(ART2_parameter_file, "%f%*[^\n]*%c", &theta);
  fscanf(ART2_parameter_file, "%f%*[^\n]*%c", &alpha);
  fscanf(ART2_parameter_file, "%f%*[^\n]*%c", &step);
  fscanf(ART2_parameter_file, "%f%*[^\n]*%c", &MXERR);
  fscanf(ART2_parameter_file, "%d%*[^\n]*%c", &MXPAS);

  ode_alloc (2*nF1);

   z    = calloc2D (nF2, 2*nF1, float);
  ztd   = calloc1D (nF2,        float *);
  zbu   = calloc1D (nF2,        float *);
   p    = calloc1D (nF1,        float);
   q    = calloc1D (nF1,        float);
   r    = calloc1D (nF1,        float);
   u    = calloc1D (nF1,        float);
   v    = calloc1D (nF1,        float);
   w    = calloc1D (nF1,        float);
   x    = calloc1D (nF1,        float);
   y    = calloc1D (nF2,        float);
  Jnext = calloc1D (nF2,         int );

  Npatlst = calloc1D (nF2,       int );

  Nactv=0;

  const = alpha / ( (1.0-d) * sqrt ((float)nF1) );
  for (j=0; j<nF2; j++)
    {
      ztd[j]=(&z[j][0]);
      zbu[j]=(&z[j][nF1]);
      for(i=0;i<nF1;i++)
        {
          ztd[j][i]=0.0;
          zbu[j][i]=const;
        }
    }
}

void run_ART(nF1, inpat, res_info, err_chan)

int     nF1;                    /* Number of nodes in an input pattern */

ACTIVATION_DATA_TYPE inpat[];   /* Array of input pattern values */

/* Locations designated to store ART 2 results for the calling program. */
struct ART2_res_ptrs    *res_info;

FILE *err_chan;                 /* Stream to receive ART 2 error messages */

/* Main routine for applying ART2 classifier to an extracted edge spectrum */

{
```

```
  /* Use "stderr" to log ART 2 errors, if no particular stream specified */
  if (err_chan == NULL) err_chan = stderr;

  Jactv = Jpntr = NONE;    /* Set flag to indicate no active category nodes */

  /* Compute initial response of feature representation (F1) nodes */
  f1relax(nF1, inpat, res_info);
  busignl(nF1);

  do
    {
      f2chooz();
      f1relax(nF1, inpat, res_info);
    } while (ARTreset==RESET);

  /* Store selected category (F2) node for use by the calling program */
  res_info->cat_node = Jactv;

  learn(nF1, inpat, res_info, err_chan);
}

f1relax(nF1, inpat, res_info)

        /* Compute response of F1 (feature representation) nodes
           to signals from input pattern and top down signals
            from an active category representation (F2) node    */

int nF1;                          /* Total number of input pattern values */
ACTIVATION_DATA_TYPE inpat[];     /* Array of input pattern values */

/* Locations designated to store ART 2 results for the calling program. */
struct ART2_res_ptrs    *res_info;

{
  int   act_cat;
  float g;

  act_cat = (Jactv != NONE) ? Jactv : 0;

  /* Nullify contribution from F2 if no category nodes are active */
  g=(Jactv!=NONE)?1.0:0.0;

  stmlax(nF1, inpat, g, ztd[act_cat]);

 /* Store value of the "match quality" metric for use by the calling program */
  res_info->R_value = R;
}

stmlax(nF1, inpat, zmult, zz)

int nF1;                          /* Total number of input pattern values */
ACTIVATION_DATA_TYPE inpat[];     /* Array of input pattern values */
float zmult, *zz;

{
  int pat_indx, itr;
  float NORM();

  for (pat_indx=0; pat_indx<nF1; ++pat_indx)
    p[pat_indx] = q[pat_indx] = r[pat_indx] = u[pat_indx] = v[pat_indx] =
                  w[pat_indx] = x[pat_indx] = 0.0;

  itr=0;        ARTreset=0;
  while (itr<MXITR && ARTreset!=RESET)
    {
      itr++;

      for (pat_indx=0; pat_indx<nF1; ++pat_indx)
        w[pat_indx] = inpat[pat_indx] + a * u[pat_indx];
      W = NORM(nF1, w);

      for (pat_indx=0; pat_indx<nF1; ++pat_indx)
        x[pat_indx] = w[pat_indx] / W;

      for (pat_indx=0; pat_indx<nF1; ++pat_indx)
        v[pat_indx] = fth(x[pat_indx]) + b * fth(q[pat_indx]);
      V=NORM(nF1, v);
```

```
      for (pat_indx=0; pat_indx<nF1; ++pat_indx)
        u[pat_indx] = v[pat_indx] / V;

      /* Add in top down signal from an F2 node */

      for (pat_indx=0; pat_indx<nF1; ++pat_indx)
        p[pat_indx] = u[pat_indx] + d * zmult * zz[pat_indx];
      P=NORM(nF1, p);

      for (pat_indx=0; pat_indx<nF1; ++pat_indx)
        r[pat_indx] = (u[pat_indx] + c * p[pat_indx]) / (1.0 + c*P);
      R=NORM(nF1, r);

      for (pat_indx=0; pat_indx<nF1; ++pat_indx) q[pat_indx] = p[pat_indx]/P;

      ARTreset=(R<rho)?RESET:0;
    }
}

f2chooz()

/* Code to select next category representation node for vigilance testing */

{
  ++Jpntr;
  Jpntr=min (Jpntr, nF2-1);
  Jactv=Jnext[Jpntr];
}

busignl(nF1)

int     nF1;    /* Number of nodes in an input pattern */

{
  int   aux_indx, cat_indx, N2, JJ;
  float YY;

  /* Consider all previously assigned nodes plus the next free one */
  N2 = min (nF2, max (Nactv+1, 1));

  /* Compute responses of category representation (F2) nodes to
     bottom up signals from the feature representation (F1) nodes */
  for (cat_indx=0; cat_indx<N2; ++cat_indx)
    {
      Jnext [cat_indx] = cat_indx;
      for(aux_indx=0, y[cat_indx]=0.0; aux_indx<nF1; aux_indx++)
        y[cat_indx] += p[aux_indx] * zbu[cat_indx][aux_indx];
    }

  /* Sort eligible F2 nodes by decreasing activation and store
     the sort results in the "Jnext" singly linked list */
  for (cat_indx=1; cat_indx<N2; ++cat_indx)
    {
      YY =   y  [cat_indx];
      JJ = Jnext[cat_indx];
      for (aux_indx=cat_indx-1; aux_indx>=0 && y[Jnext[aux_indx]]<YY;
           --aux_indx)
        Jnext[aux_indx+1]=Jnext[aux_indx];
      Jnext[aux_indx+1]=JJ;
    }

  ndchg=(Jnext[0]!=Jactv)?NDCHG:0;
}

learn(nF1, inpat, res_info, err_chan)

int     nF1;                    /* Number of nodes in an input pattern */

ACTIVATION_DATA_TYPE inpat[];   /* Array of input pattern values */

/* Locations designated to store ART 2 results for the calling program. */
struct ART2_res_ptrs    *res_info;

FILE *err_chan;                 /* Stream to receive ART 2 error messages */
```

```
{
  int            pas,nok,nbad,j;
  float          ans,err,strt,fnsh,tol,
                 h=1.0e-02,hmin=1.0e-04,
                 *new,*zz;
  char           *calloc();
  void           ode();

  zz=z[Jactv];
  tol=10.*MXERR;
  new=calloc1D(2*nF1,float);
  if (Npatlst[Jactv]==0) Nactv++;
  Npatlst[Jactv]++;
  fprintf(stdout,"\nLEARNING CURRENT PATTERN ON NODE %d ",Jactv);

  for (j=0;j<2*nF1;j++) new[j]=zz[j];

  strt=0.0;

  pas= -1;     err=1.e10;   ARTreset=0;
  while (pas<MXPAS && err>MXERR && ARTreset!=RESET)
    {
      pas++;       err=0.0;

      fnsh=strt+step;

      ode(new, 2*nF1, strt, fnsh, tol, h, hmin, &nok, &nbad, inpat, err_chan);

      for (j=0;j<2*nF1;j++)
        {
          ans = fabs(new[j]-zz[j]);
          if (ans>err) err=ans;
          zz[j]=new[j];
        }

      busignl(nF1);
    }
  fprintf(stdout, " - pattern learned after %d passes.\n", pas);

  /* Store actual number of learning passes for use by the calling program */
  res_info->num_pass = pas;

  if (ARTreset==RESET) fprintf(err_chan,"\nF2 RESET : R=%4f\n",R);
  if (ndchg==NDCHG) fprintf(err_chan,"\nF2 CHANGE: %d->%d\n",Jactv,Jnext[0]);
}

/*--------------------------------------------------------------------------*/

/* Routines to perform explicit solution of differential equations for F2 */

#define MAXSTP 10000
#define TINY 1.0e-30

float *yscal, *yy,   *dydx;
float *dysav, *ysav, *ytemp;
float *dym,   *dyt,  *yt;

void ode_alloc(nvar)
int nvar;
{
  yy    = calloc1D (nvar,float);
  dydx  = calloc1D (nvar,float);
  yscal = calloc1D (nvar,float);
  ysav  = calloc1D (nvar,float);
  dysav = calloc1D (nvar,float);
  ytemp = calloc1D (nvar,float);
  dym   = calloc1D (nvar,float);
  dyt   = calloc1D (nvar,float);
  yt    = calloc1D (nvar,float);
}


                    ++ftr_counter;
                  }
```

```
/*-------------------------------------------------------*/
/*                                                       */
/*  Offset Signal Calculations for the Southerly Direction */
/*                                                       */
/*-------------------------------------------------------*/

    /* Initialization - Pack Data from Compressed Image
         into the 7 x 3 Neural Network Input Array      */

        input_index=0;
        V2_base_ptr = (INPUT_WINDOW_SIZE-1) * INPUT_WINDOW_SIZE;
        for (scan_col=0; scan_col<INPUT_WINDOW_SIZE; ++scan_col)
          {
            V2_ptr = V2_base_ptr + scan_col;
            for (scan_row=0; scan_row<V2AUX_WINDOW_SIZE; ++scan_row)
              {
                input_neuron_signal[input_index++] =
                  V2_hidden_layer[V2_ptr];
                V2_ptr -= INPUT_WINDOW_SIZE;
              }
          }

        /* Actual Calculation for Raw Sub-Image */

        compute_hidden_unit_activations
          (INPUT_WINDOW_SIZE * V2AUX_WINDOW_SIZE, N_HIDDEN_NEURONS,
           V2_A_wts, V2_B_wts)

  /* Compute Direct Contributions to Output Layer Activations
     from Input Signals and Store them in Designated Array */

        matrix_vector_product
          (INPUT_WINDOW_SIZE * V2AUX_WINDOW_SIZE, N_OUTPUTS,
           V2_D_wts, input_neuron_signal, B_or_D_fi)

 /* Pass hidden unit activations through the sigmoid rectification */
        for(input_index=0; input_index<N_HIDDEN_NEURONS;
            input_index++)
          sigrect[input_index] =
            step_sigmoid(hidden_neuron_signal[input_index]);

/* Compute Contributions to Output Layer Activations from Hidden Units */
        matrix_vector_product(N_HIDDEN_NEURONS, N_OUTPUTS, V2_C_wts,
                              sigrect, output_neuron_signal)

     /* Compute Final Output Activations by Combining
        Contributions from the Input and Hidden Layers
       and Store Results in Edge Detection Feature Array */
        for(input_index=0; input_index<N_OUTPUTS; input_index++)
          {
            output_neuron_signal[input_index] +=
              B_or_D_fi[input_index];
            frwd_feature[ftr_counter] =
              output_neuron_signal[input_index];
          }

       /* Compute Complement of the Input Sub-Image */
void ode_free()
{
  free ( (char *)yy    );
  free ( (char *)dydx  );
  free ( (char *)yscal);
  free ( (char *)ytemp);
  free ( (char *)dysav);
  free ( (char *)ysav );
  free ( (char *)yt    );
  free ( (char *)dyt   );
  free ( (char *)dym   );
}

void ode(ystart, nvar, x1, x2, eps, h1, hmin, nok, nbad, inpat, err_chan)

float ystart[], x1, x2, eps, h1, hmin;
int nvar, *nok, *nbad;
ACTIVATION_DATA_TYPE inpat[];   /* Array of input pattern values */
FILE *err_chan;                 /* Stream to receive ART 2 error messages */
```

```
{
  int nstp,i;
  float xx,hnext,hdid,h;
  void rkqc(),derivs();

  xx=x1;
  h=(x2 > x1) ? fabs(h1) : -fabs(h1);
  *nok = (*nbad) =  0;
  for (i=0;i<nvar;i++) yy[i]=ystart[i];
  for (nstp=0;nstp<MAXSTP;nstp++) {
    stmlax((nvar/2), inpat, 1.0, yy);
    derivs(nvar, yy, dydx);
    for (i=0;i<nvar;i++)
      yscal[i]=fabs(yy[i])+fabs(dydx[i]*h)+TINY;
    if ((xx+h-x2)*(xx+h-x1) > 0.0) h=x2-xx;
    rkqc(nvar,&xx,h,eps,&hdid,&hnext,err_chan);
    if (hdid == h) ++(*nok); else ++(*nbad);
    if ((xx-x2)*(x2-x1) >= 0.0) {
      for (i=0;i<nvar;i++) ystart[i]=yy[i];
      return;
    }
    if (fabs(hnext)<=hmin)
      if (err_chan == stderr) message(odeerr_1);
      else fprintf(err_chan, "\n     %s", odeerr_1);
    h=hnext;
  }
  if (err_chan == stderr) message(odeerr_2);
  else fprintf(err_chan, "\n     %s", odeerr_2);
}

#undef MAXSTP
#undef TINY

#define PGROW -0.20
#define PSHRNK -0.25
#define FCOR 0.06666666         /* 1/15 */
#define SAFETY 0.9
#define ERRCON 6.0e-4

void rkqc(n, x, htry, eps, hdid, hnext, err_chan)
float *x,htry,eps,*hdid,*hnext;
int n;
FILE *err_chan;                 /* Stream to receive ART 2 error messages */
{
  int i;
  float xsav,hh,h,temp,errmax;
  void derivs(),rk4();

  xsav=(*x);
  for (i=0;i<n;i++) {
    ysav[i]=yy[i];
    dysav[i]=dydx[i];
  }

  h=htry;
  for (;;) {
    hh=0.5*h;
    rk4(ysav,dysav,n,hh,ytemp);
    *x=xsav+hh;
    derivs(n, ytemp, dydx);
    rk4(ytemp,dydx,n,hh,yy);
    *x=xsav+h;
    if (*x == xsav)
      if (err_chan == stderr) message(odeerr_3);
      else fprintf(err_chan, "\n     %s", odeerr_3);
    rk4(ysav,dysav,n,h,ytemp);
    errmax=0.0;
    for (i=0;i<n;i++) {
      ytemp[i]=yy[i]-ytemp[i];
      temp=fabs(ytemp[i]/yscal[i]);
      if (errmax>temp) errmax=temp;
    }
    errmax /= eps;
    if (errmax <= 1.0) {
```

```
      *hdid=h;
      *hnext=(errmax > ERRCON ?
        SAFETY*h*exp(PGROW*log(errmax)) : 4.0*h);
      break;
    }
    h=SAFETY*h*exp(PSHRNK*log(errmax));
  }
  for (i=0;i<n;i++) yy[i] += ytemp[i]*FCOR;
}

#undef PGROW
#undef PSHRNK
#undef FCOR
#undef SAFETY
#undef ERRCON

void rk4(y,dydx,n,h,yout)
float y[],dydx[],h,yout[];
int n;
{
  int i;
  float hh,h6;
  void derivs();
  hh=h*0.5;
  h6=h/6.0;
  for (i=0;i<n;i++) yt[i]=y[i]+hh*dydx[i];
  derivs(n, yt, dyt);
  for (i=0;i<n;i++) yt[i]=y[i]+hh*dyt[i];
  derivs(n, yt, dym);
  for (i=0;i<n;i++) {
    yt[i]=y[i]+h*dym[i];
    dym[i] += dyt[i];
  }
  derivs(n, yt, dyt);
  for (i=0;i<n;i++)
    yout[i]=y[i]+h6*(dydx[i]+dyt[i]+2.0*dym[i]);
}

char **kalloc2D (NY, NX, SIZE, SIZESTAR)

int              NY, NX, SIZE, SIZESTAR;
{
  char   **K;
  char   *calloc();
  int    J;

  K    = (char **)calloc (  NY, SIZESTAR);
  K[0] = (char *) calloc (NX*NY,  SIZE  );
  for (J=1; J<NY; J++)
    K[J] = K[0] + SIZE*NX*J;

  return(K);
}

void derivs(nz, zz, dz)

/* Number of points where derivative calculation is to be performed */
int     nz;

float   *zz, *dz;
{
  int            i;

  for (i=0; i<nz; i++) dz[i]=d*(p[i%(nz/2)]-zz[i]);
}

float NORM(nelem, vec)

int     nelem;  /* Number of elements in vector to be normalized */
float   *vec;

{
  int            i;
  float          norm;

  for (i=0, norm=0.0; i<nelem; i++) norm+=sqr(vec[i]);
```

```
  return(sqrt(norm));
}

        /* IRP_LGN.c            Printed on 18-December-1989 */

/*
             Code to compute coarse, global image features (LGN)
                to be used in object classification for IRP
*/

          /* Originally coded by KG Heinemann on 08-August-1989 */
                /* Coding resumed on 04 October 1989 */

#include        <stdio.h>
#include        <math.h>

#include        <suntool/sunview.h>
#include        <suntool/canvas.h>
#include        <suntool/panel.h>

#include "image_io.h"
#include "activation.h"

ACTIVATION_DATA_TYPE LGN_sum()
{
  int                     loop_index;
  long                    cumulint;
  ACTIVATION_DATA_TYPE    norm_sum;

  for(loop_index=0, cumulint=0; loop_index<(size_x*size_y); ++loop_index)
    cumulint += image[loop_index];

  norm_sum =
    (ACTIVATION_DATA_TYPE)cumulint / (ACTIVATION_DATA_TYPE)(VLT_SIZE - 1);

  return(norm_sum);
}
```

We claim:

1. Apparatus for recognizing, as one of at least two possible patterns, a pattern within an image based on visual characteristics of the pattern, said image being represented by signals whose values correspond to said visual characteristics, comprising a location channel which determines the location of the pattern within the image based on the signal values, and a classification channel which categorizes the pattern based on the signal values and generates an indication of the pattern's object identity from among a set of possible identities, said classification channel comprising addition means for summing said signal values to generate an indication of the overall size of said pattern, orientation means for sensing edges of said pattern and generating indications of orientations of said edges, and an unsupervised classifier which processes a classification spectrum comprised of said size indication and said orientation indications are based on said processing, automatically selects and associates characteristics from the spectrum to define categories, said location channel and said classification channel operating simultaneously in parallel and cooperatively to recognize said pattern as said one of said patterns.

2. The apparatus of claim 1 wherein said location channel comprises a coarse locator which makes a coarse determination of the existence and location of the pattern within the image, and a fine locator, responsive to the coarse, which makes a fine determination of the location of the pattern within the image.

3. The apparatus of claim 2 wherein said coarse locator comprises a neural network which processes said image with interconnecting traces whose weights are chosen based on general shape of interest.

4. The apparatus of claim 3 wherein said coarse locator operates with respect to a field of view within said image and a feedback path from said classification channel to said location channel controls the position of the field of view within the image.

5. The apparatus of claim 2 wherein said fine locator includes circuitry for responding to feedback from said classification channel in order to adjust the position of a field of view within said image in order to determine the fine location of a pattern within the image.

6. The apparatus of claim 4 wherein said coarse locator provides a feedforward signal to said fine locator to control the fine position of said field of view.

7. The apparatus of claim 1 wherein said classification channel further comprises calibration means for calibrating said signal values so that said values are evenly distributed across a predefined range of values before being processed by said addition means and said orientation means, and a supervised classifier which associates categories defined by said unsupervised classifier with user-specified object identities.

8. The apparatus of claim 1 wherein said orientation means is adapted to generate measures of the strengths of edges in predetermined orientations within portions of said image.

9. The apparatus of claim 1 wherein said orientation means is adapted to generate indications of orientations of edges at the periphery of a portion of said image.

10. The apparatus of claim 8 wherein said predetermined orientations include vertical, horizontal, and 45°.

11. The apparatus of claim 9 wherein said orientation means is adapted to generate measures of the existence of said edges at the top, bottom, and each side of the image.

12. The apparatus of claim 1 wherein said indications which correspond to coarser features appear in the lower end of said spectrum and measures which correspond to finer features appear in the upper end of said spectrum.

13. The apparatus of claim 7 wherein said classification channel includes a feedback path for providing said classification spectrum information to said location channel.

14. Apparatus for recognizing a pattern within an image based on visual characteristics of said pattern, said pattern having edges, said image being represented by signals whose values correspond to said visual characteristics, comprising an orientation analyzer adapted to analyze the orientations of edges of the pattern within subwindows of said image, a strength analyzer adapted to analyze the strengths of edges of the pattern near the periphery of a portion of said image, a classifier for processing the outputs of said orientation and strength analyzers as part of a spectrum, and a mapper for causing outputs of subwindows of said image to be treated in said spectrum in an order such that outputs of subwindows nearer to the center of the image are treated as appearing higher on the spectrum than outputs of subwindows near the periphery of the image.

15. The apparatus of claim 14 wherein said orientation analyzer comprises detectors for detecting the strengths of orientation of edges in four different possible orientations.

16. The apparatus of claim 15 wherein said four different possible orientations comprises 0, 45, 90, and 135 degrees, respectively.

17. The apparatus of claim 15 wherein each said analyzer comprises neural networks.

18. The apparatus of claim 15 wherein said strength analyzer comprises an averaging module for averaging elements of a subwindow to derive an averaged subwindow and four neural networks for processing said averaged subwindow to determine the strength of edges at the north, south, east, and west peripheries of said subwindow.

19. Apparatus for recognizing, as one of at least two possible patterns, a pattern within an image based on visual characteristics of the pattern, said image being represented by signals whose values correspond to said visual characteristics, comprising a location channel which determines the location of the pattern within the image based on the signal values, and a classification channel which categorizes the pattern based on the signal values and generates an indication of the pattern's object identity from among a set of possible identities, said classification channel comprising addition means for summing said signal values to generate an indication of the overall size of said pattern, orientation means for sensing edges of said pattern and generating indications of orientations of said edges, and an unsupervised classifier which processes a classification spectrum comprised of said size indication and said orientation indications are based on said processing, automatically selects and associates characteristics from the spectrum to define categories, and a feedback path from said classification channel to said location channel to cause said location channel to adapt to classification results generated by said classification channel, said location channel and said classification channel operating simultaneously in parallel and cooperatively to recognize said pattern as said one of said patterns.

20. Apparatus for recognizing, as one of at least two health conditions, the health condition of a biological cell within an image based on visual characteristics of the cell, said image being represented by signals whose values correspond to said visual characteristics, comprising a location channel which determines the location of the cell within the image based on the signal values, and a classification channel which categorizes the cell based on the signal values and generates an indication of the cell's object health conditions from among a set of possible health conditions, said classification channel comprising addition means for summing said signal values to generate an indication of the overall size of said cell, orientation means for sensing edges of said cell and generating indications of orientations of said edges, and an unsupervised classifier which processes a classification spectrum comprised of said size indication and said orientation indications and based on said processing, automatically selects and associates characteristics from the spectrum to define health condition categories, said location channel and said classification channel operating simultaneously in parallel and cooperatively to recognize the health condition of said cell as said one of said health conditions.

21. The apparatus of claim 20 wherein said classification channel further comprises storage for said classification spectrum information about the visual characteristics of said cell for use in categorizing said health condition of said cell.

22. The apparatus of claim 20 wherein said location channel comprises a coarse locator which makes a coarse determination of the existence and location of the cell within the image, and a fine locator, responsive to the coarse, which makes a fine determination of the location of the cell within the image.

23. The apparatus of claim 22 wherein said coarse locator comprises a neural network which processes said image with interconnecting traces whose weights are chosen based on cell shapes of interest.

24. The apparatus of claim 23 wherein said coarse locator operates with respect to a field of view within said image and a feedback path from said classification channel to said location channel controls the position of the field of view within the image.

25. The apparatus of claim 24 wherein said coarse locator provides a feedforward signal to said fine locator to control the fine position of said field of view.

26. The apparatus of claim 22 wherein said fine locator includes circuitry for responding to feedback from said classification channel in order to adjust the position of a field of view within said image in order to determine the fine location of the cell within the image.

27. The apparatus of claim 20 wherein said classification channel further comprises calibration means for calibrating said signal values so that said values are evenly distributed across a predefined range of values before being processed by said addition means and said orientation means, and a supervised classifier which associates health condition categories defined by said unsupervised classifier with user-specified health conditions.

28. The apparatus of claim 27 wherein, said classification channel includes a feedback path for providing said classification spectrum information to said location channel.

29. The apparatus of claim 20 wherein said orientation means is adapted to generate indications of orientations of edges at the periphery of a portion of said image.

30. Apparatus for recognizing the health condition of a biological cell within an image based on visual characteristics of said cell, said cell having visible edges, said image being represented by signals whose values correspond to said visual characteristics, comprising an orientation analyzer adapted to analyze the orientations of edges of the cell within subwindows of said image, a strength analyzer adapted to analyze the strengths of edges of the cell near the periphery of a portion of said image, a classifier for processing the outputs of said orientation and strength analyzers as part of a spectrum, and a mapper for causing outputs of subwindows of said image to be treated in said spectrum in an order such that outputs of subwindows nearer to the center of the image are treated as appearing higher on the spectrum than outputs of subwindows near the periphery of the image.

31. The apparatus of claim 30 wherein said orientation analyzer comprises detectors for detecting the strengths of orientation of edges in four different possible orientations.

32. The apparatus of claim 31 wherein each said analyzer comprises neural networks.

33. The apparatus of claim 31 wherein said strength analyzer comprises an averaging module for averaging elements of a subwindow to derive an averaged subwindow and four neural networks for processing said averaged subwindow to determine the strength of edges at the north, south, east, and west peripheries of said subwindow.

34. Apparatus for recognizing, as one of at least two health conditions, the health condition of a biological cell within an image based on visual characteristics of the cell, said image being represented by signals whose values correspond to said visual characteristics, comprising a location channel which determines the location of the cell within the image based on the signal values, a classification channel which categorizes the cell based on the signal values and generates an indication of the cell's health condition from among a set of possible health conditions, said classification channel comprising addition means for summing said signal values to generate an indication of the overall size of said cell, orientation means for sensing edges of said cell and generating indications of orientations of said edges, and an unsupervised classifier which processes a classification spectrum comprised of said size indication and said orientation indications and based on said processing, automatically selects and associates characteristics from the spectrum to define health condition categories, and a feedback path from said classification channel to said location channel to cause said location channel to adapt to classification results generated by said classification channel, said location channel and said classification channel operating simultaneously in parallel and cooperatively to recognize the health condition of said cell as said one of said health conditions.

* * * * *

UNITED STATES PATENT AND TRADEMARK OFFICE

CERTIFICATE OF CORRECTION

PATENT NO. : 5,313,532

DATED : May 17, 1994

INVENTOR(S) : Robert L. Harvey, Paul N. DiCaprio, and Karl G. Heinemann

It is certified that error appears in the above-indentified patent and that said Letters Patent is hereby corrected as shown below:

Col. 1, line 25, replace "Whether" with --whether--.

Col. 2, line 61, replace "Possible" with --possible--.

Col. 6, line 18, replace "A, 3, C, and D" with --A, B, C, and D--.

Col.6, line 19, replace "within-the" with --within the--.

Col. 6, line 66, replace "approaches-to" with --approaches to--.

Col. 8, line 38, replace "Self-organization" with --Self-Organization--.

Col. 8, line 40, replace "optics" with --Optics--.

Col. 11, line 10, replace "delta2" with --delta 2--.

Col. 12, line 13, replace "hive" with --have--.

UNITED STATES PATENT AND TRADEMARK OFFICE
CERTIFICATE OF CORRECTION

PATENT NO. : 5,313,532

DATED : May 17, 1994

INVENTOR(S) : Robert L. Harvey, Paul N. DiCaprio, and Karl G. Heinemann

It is certified that error appears in the above-indentified patent and that said Letters Patent is hereby corrected as shown below:

Col. 12, line 18, replace "Possibly" with --possibly--.

Col. 13, line 21, replace "analyses" with --analyzes--.

Col. 13, ine 32, replace "analyse" with --analyze--.

Col. 152, line 43, replace "shape" with --shapes--.

Col. 154, line 37, replace "conditions" with --condition--.

Col. 155, line 29, after "wherein" delete ",".

Signed and Sealed this

Twenty-eighth Day of May, 1996

Attest:

BRUCE LEHMAN

*Attesting Officer* *Commissioner of Patents and Trademarks*